United States Patent [19]
Tanikawa et al.

[11] Patent Number: 5,817,828
[45] Date of Patent: Oct. 6, 1998

[54] PYRAZOLE DERIVATIVES

[75] Inventors: Keizo Tanikawa; Yoshimasa Kamikawaji; Keisuke Odoi; Tsutomu Higashiyama; Masayuki Sato, all of Chiba-ken; Yukinori Masuda, Saitama-ken, all of Japan

[73] Assignee: Nissan Chemical Industries, Ltd., Tokyo, Japan

[21] Appl. No.: 999,493

[22] Filed: Dec. 29, 1997

Related U.S. Application Data

[62] Division of Ser. No. 525,555, Sep. 29, 1995, Pat. No. 5,721,264.

[30] Foreign Application Priority Data

Apr. 7, 1993 [JP] Japan ............................... HEI 5-80922
Jan. 10, 1994 [JP] Japan ................................. HEI 6-917

[51] Int. Cl.$^6$ ....................... A61K 31/415; C07D 403/12
[52] U.S. Cl. ............................................ 548/253; 514/381
[58] Field of Search ............................... 548/253; 514/381

[56] References Cited

U.S. PATENT DOCUMENTS

| | | |
|---|---|---|
| 4,207,324 | 6/1980 | Matsumura et al. . |
| 4,340,598 | 7/1982 | Furukawa et al. . |
| 4,576,958 | 3/1986 | Wexler . |
| 4,582,847 | 4/1986 | Furukawa et al. . |
| 4,880,804 | 11/1989 | Carini et al. . |
| 5,326,776 | 7/1994 | Winn et al. . |

FOREIGN PATENT DOCUMENTS

| | | |
|---|---|---|
| 28 834 | 5/1981 | European Pat. Off. . |
| 245 637 | 11/1987 | European Pat. Off. . |
| 253 310 | 1/1988 | European Pat. Off. . |
| 291 969 | 11/1988 | European Pat. Off. . |
| 475 206 | 3/1992 | European Pat. Off. . |
| WO 93/17681 | 9/1993 | WIPO . |
| WO 93/17682 | 9/1993 | WIPO . |

OTHER PUBLICATIONS

Clin. And Exper. Hyper.–Theory and Practice, A4(1–2), "Inhibitors of the Renin–Angiotension System as new Antilhypertensive agents" Michael J. Antonaccio, pp. 27–46 (1982).

The Journal of Pharmacology and Experimantal Therapeutics, vol. 247, No. 1, "Nonpeptide Angiotensin II Receptor Antagonist. I. Pharmacological Characterization of 2–n–Butyl–4–chloro–1–(2–chlorobenzyl(imidazole—5–acetic acid, sodium salt (s–8307)", Pancras C. Wong et al., pp. 1–7 (1988).

J. Med. Chem., vol. 36, No. 21, "A Potent Oraly Active Balanced Affinity Angiotensin II AT1 Antagonist and AT2 Binding Inhibitor", Stephen E. De Laszlo et al., pp. 3207–3210, (1993).

European Jouranl of Pharmacology, vol. 157, "Non–peptide angiotensin II receptor antagonists", Andrew T. Chiu et al., pp. 13–21, (1988).

*Primary Examiner*—Robert W. Ramsuer
*Attorney, Agent, or Firm*—Oliff & Berridge, PLC

[57] ABSTRACT

Pyrazole compounds of formula [1] and their tautomers and salts:

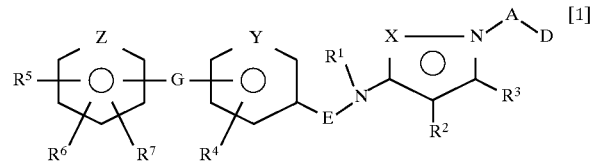

(wherein $R^1$ is an alkyl group, etc.; $R^2$ is a carboxyl group, etc.; $R^3$ is a halogen atom, an alkyl group, a phenyl group, etc.; $R^4$, $R^5$ and $R^6$ each are a hydrogen atom, a halogen atom, etc.; $R^7$ is a carboxyl group, a 5-tetrazolyl group, etc.; X is a nitrogen atom, etc.; Y and Z each are CH, a nitrogen atom, etc.; A and E each are a methylene group, etc.; D is a phenyl group, etc.; G is a covalent bond, etc.).

The compounds of the invention have an antagonistic effect against angiotensin II and are useful for prevention and remedy of hypertension, congestive cardiac insufficiency, chronic renal insufficiency, aldosteronism, hyper-intraocular pressure, etc.

8 Claims, No Drawings

PYRAZOLE DERIVATIVES

This is a Division of application Ser. No. 08/525,555 filed Sep. 29, 1995 now U.S. Pat. No. 5,721,264 (U.S. National Stage of PCT/JP94/00587 filed Apr. 7, 1994). The entire disclosure of the prior application(s) is hereby incorporated by reference herein in its entirety.

TECHNICAL FIELD

The present invention relates to novel pyrazole compounds and their tautomers and salts, which are useful as antagonists against angiotensin II in remedy for various cardiovascular disorders, especially in remedy for hypertension, cardiac insufficiency and venous insufficiency, as well as in remedy for glaucoma, diabetic retinopathy and various central nervous system disorders, such as anxiety neurosis, melancholia, hypomnesia, Alzheimer's disease or chronic renal insufficiency.

BACKGROUND ART

Renin-angiotensin system plays an important part in general blood pressure regulation, and it substantially participates in the manifestation of hypertension and congestive cardiac insufficiency. Angiotensin II is an octapeptide hormone and is essentially formed in blood when angiotensin I which is a decapeptide hormone is cut by angiotensinase (angiotensin-converting enzyme; ACE). The ACE exists locally in the vascular endothelia of lung, kidney and other various organs. Angiotensin II which is a strong arterial angiotonic agent in renin-angiotensin system acts on a specific receptor in the surfaces of cell membranes. Therefore, one method for controlling renin-angiotensin system is to utilize the antagonistic effect against the angiotensin II receptor. It is known that some peptide analogues of angiotensin II antagonistically block the receptor to thereby retard the effect of the hormone. However, since these peptide analogues have a partial agonistic activity and are poorly absorbed by peroral administration, their use in experimental and clinical purposes has heretofore been limited [see M. Antonaccio, Clin. Exp. Hypertens., A4, 27–46 (1982)].

Recently, some non-peptide compounds have been reported as antagonists against angiotensin II [see U.S. Pat. No. 4,207,324, No. 4,340,598, No. 4,576,958, No. 4,582,847 and No. 4,880,804; European Patent Application Laid-Opens No. 028,834, No. 245,637, No. 253,310, No. 291,969 and No. 475,206; WO 93/17681 and WO 93/17682, etc.; A. T. Chiu, et al., Eur. J. Pharm. Exp. Therap., 157, 13–21 (1988); P. C. Wong, et al., J. Pharm. Exp. Therap., 247, 1–7 (1988); S. E. Laszlo, et al., J. Med. Chem., 1993, 36, 3207–3210, etc.].

However, none of the above-mentioned U.S. patent specification, European Patent Application Laid-Open publications, PCT International Laid-Open Patent Applications and the reports has disclosed the pyrazole compounds and their tautomers and salts of the present invention.

The present invention relates to novel pyrazole compounds and their tautomers and salts which are useful as antagonists against angiotensin II in remedy for various disorders such as hypertension, congestive cardiac insufficiency, chronic renal insufficiency, aldosteronism, hyper-intraocular pressure, etc.

DISCLOSURE OF INVENTION

The present inventors intensively investigated and researched and, as a result, have unexpectedly found that the pyrazole compounds and their tautomers and salts of the present invention, which are different from all the compounds disclosed in the above-defined publications and literatures, are useful as antagonists against angiotensin II capable of binding to not only $AT_1$ receptors but also $AT_2$ receptors, that they are extremely useful as antihypertensives and that they may be active ingredients in medicines for preventing and treating the above-mentioned disorders such as congestive cardiac insufficiency, chronic renal insufficiency, aldosteronism, hyper-intraocular pressure, etc. On the basis of these findings, the present inventors have completed the present invention.

Specifically, the present invention relates to pyrazole compounds of the following general formula [1] and their tautomers and salts:

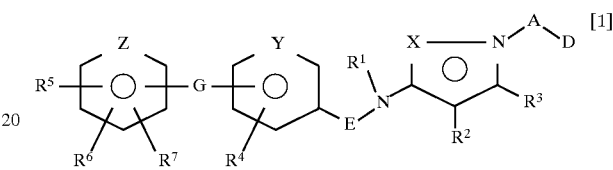

[wherein $R^1$ represents a hydrogen atom, a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^8R^{8'}$ (in which $R^8$ and $R^{8'}$ each independently represent a hydrogen atom, a $C_1$–$C_{10}$ alkyl group or a $C_6$–$C_{10}$ aromatic group), $SR^9$ (in which $R^9$ has the same meaning as $R^8$), a $C_6$–$C_{10}$ aromatic group and a heterocyclic group}, a $C_2$–$C_{10}$ alkenyl group {said alkenyl group is unsubstituted or substituted by one or more substituents selected from a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, a $C_2$–$C_{10}$ alkynyl group {said alkynyl group is unsubstituted or substituted by one or more substituents selected from a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, a $C_3$–$C_{10}$ cycloalkyl group {(said cycloalkyl group is unsubstituted or substituted by one or more substituents selected from a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, a $C_3$–$C_{10}$ cycloalkenyl group {said cycloalkenyl group is unsubstituted or substituted by one or more substituents selected from a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, a $C_6$–$C_{10}$ aromatic group {said aromatic group is unsubstituted or substituted by one or more substituents selected from a $C_1$–$C_{10}$ alkyl group, a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, a heterocyclic group {said heterocyclic group is unsubstituted or substituted by one or more substituents tuents selected from a $C_1$–$C_{10}$ alkyl group, a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, a $C_1$–$C_{10}$ acyl group {said acyl group is unsubstituted or substituted by one or more substituents selected from a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, a $C_1$–$C_{10}$ alkylcarbamoyl group {said alkylcarbamoyl group is unsubstituted or substituted by one or more substituents selected from a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, a $C_1$–$C_{10}$ alkoxycarbonyl group {said alkoxycarbonyl group is unsubstituted or substituted by one or more substituents selected from a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group}, or a $C_6$–$C_{10}$ aryloxycarbonyl group {said aryloxycarbonyl group is unsubstituted or substituted by one or more substituents selected from a $C_1$–$C_{10}$ alkyl group, a halogen atom, a hydroxyl group, a $C_1$–$C_{10}$ alkoxy group, $NR^8R^{8'}$ (in which $R^8$ and $R^{8'}$ each independently have the same meanings as defined above), $SR^9$ (in which $R^9$ has the same meaning as defined above), a $C_6$–$C_{10}$ aromatic group and a heterocyclic group};

$R^2$ represents a halogen atom, a nitro group, a cyano group, a formyl group, a sulfonic acid group, a sulfonamide group, $PO_2H_2$, $PO_3H_2$, a 5-tetrazolyl group, a 5-tetrazolylmethyl group, a 5-tetrazolylethyl group, a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently represent a hydrogen atom, a $C_1$–$C_{10}$ alkyl group or a $C_6$–$C_{10}$ aromatic group), $SR^{11}$ (in which $R^{11}$ has the same meaning as $R^{10}$), a $C_6$–$C_{10}$ aromatic group and a heterocyclic group)}, a $C_2$–$C_{10}$ alkenyl group {said alkenyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a $C_2$–$C_{10}$ alkynyl group {said alkynyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a $C_3$–$C_{10}$ cycloalkyl group {said cycloalkyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a $C_3$–$C_{10}$ cycloalkenyl group {said cycloalkenyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a $C_6$–$C_{10}$ aromatic group {said aromatic group is unsubstituted or substituted by one or more substituents selected from a $C_1$–$C_{10}$ alkyl group, a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a heterocyclic group {said heterocyclic group is unsubstituted or substituted by one or more substituents selected from a $C_1$–$C_{10}$ alkyl group, a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a $C_1$–$C_{10}$ acyl group {said acyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a $C_1$–$C_{10}$ alkylcarbamoyl group {said alkylcarbamoyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a $C_1$–$C_{10}$ alkoxycarbonyl group {said alkoxycarbonyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, a $C_6$–$C_{10}$ aryloxycarbonyl group {said aryloxycarbonyl group is unsubstituted or substituted by one or more substituents selected from a $C_1$–$C_{10}$ alkyl group, a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, $(CH_2)m^1COX^1R^{12}$ [in which $m^1$ represents 0, 1 or 2; $R^{12}$ represents a hydrogen atom or a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}; $X^1$ represents an oxygen atom, a sulfur atom or $NR^{13}$ (in which $R^{13}$ has the same meaning as $R^{10}$)], $(CH_2)n^1X^2R^{14}$ [in which $n^1$ represents 0, 1 or 2; $R^{14}$ represents a hydrogen atom, a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}, or a $C_1$–$C_{10}$ acyl group {said acyl group is unsubstituted or substituted by one or more substituents selected from a halogen atom, a hydroxyl group, a $C_1$–$C_{10}$ alkoxy group, $NR^{10}R^{10'}$ (in which $R^{10}$ and $R^{10'}$ each independently have the same meanings as defined above), $SR^{11}$ (in which $R^{11}$ has the same meaning as defined above), a $C_6$–$C_{10}$ aromatic group and a heterocyclic group}; $X^2$ represents an oxygen atom, $S(O)n^2$ (in which $n^2$ represents 0, 1, 2 or 3), or $NR^{16}$ {in which $R^{15}$ has the same meaning as $R^{12}$ or represents $SO_2R^{16}$ (in which $R^{16}$ represents a $C_1$–$C_{10}$ alkyl group which is unsubstituted or substituted by halogen atom(s)}], or an oxadiazole group of:

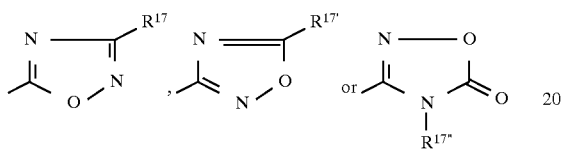

(wherein $R^{17}$, $R^{17'}$ and $R^{17-}$ each have the same meanings as $R^{10}$); $R^3$ represents a halogen atom, a hydroxyl group, a nitro group, a cyano group, a formyl group, a guanidino group, an amidino group, a sulfonic acid group, a sulfonamide group, $PO_2H_2$, $PO_3H_2$, a 5-tetrazolyl group, a 5-tetrazolylmethyl group, a 5-tetrazolylethyl group, a $C_1$–$C_{10}$ alkyl group {said alkyl group is unsubstituted or substituted by one or more substituents ents selected from a halogen atom, a hydroxyl group, a $C_1$–$C_{10}$ alkoxy group, $NR^{18}R^{18'}$ (in which $R^{18}$ and $R^{18'}$ each independently represent a hydrogen atom, a $C_1$–$C_{10}$ alkyl group or a $C_6$–$C_{10}$ aromatic group), $SR^{19}$ (in which $R^{19}$ has the same meaning as $R^{18}$), a $C_6$–$C_{10}$ aromatic group and a heterocyclic group}, a $C_2$–$C_{10}$ alkenyl group {said alkenyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_2$–$C_{10}$ alkynyl group {said alkynyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as mentioned above), $SR^{19}$ (in which $R^{19}$ has the same meaning as mentioned above), a $C_6$–$C_{10}$ aromatic group and a heterocyclic group}, a $C_3$–$C_{10}$ cycloalkyl group {said cycloalkyl group is unsubstituted or substituted by one or more substituents selected from a halogen atom, a hydroxyl group, a $C_1$–$C_{10}$ alkoxy group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_3$–$C_{10}$ cycloalkenyl group {said cycloalkenyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_6$–$C_{10}$ aromatic group [said aromatic group is unsubstituted or mono-substituted to penta-substituted by one or more substituents selected from a halogen atom, a hydroxyl group, a nitro group, a cyano group, a formyl group, a guanidino group, an amidino group, a sulfonic acid group, a sulfonamide group, $PO_2H_2$, $PO_3H_2$, a 5-tetrazolyl group, a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_2$–$C_{10}$ alkenyl group {said alkenyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_3$–$C_{10}$ cycloalkyl group {said cycloalkyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, $(CH_2)m^2COX^3R^{20}$ [in which $m^2$ represents 0, 1 or 2; $R^{20}$ represents a hydrogen atom or a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}; $X^3$ represents an oxygen atom, a sulfur atom or $NR^{21}$ (in which $R^{21}$ has the same meaning as $R^{18}$)], $(CH_2)n^3X^4R^{22}$ [in which $n^3$ represents 0, 1 or 2; $R^{22}$ represents a hydrogen atom, a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, or a $C_1$–$C_{10}$ acyl group {said acyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}; $X^4$ represents an oxygen atom, $S(O)n^4$ (in which $n^4$ represents 0, 1, 2 or 3), or $NR^{23}$ {in which $R^{23}$ has the same meaning as $R^{20}$ or represents $SO_2R^{24}$ (in which $R^{24}$ represents a $C_1$–$C_{10}$ alkyl group which is unsubstituted or substituted by halogen atom(s))}], a $C_6$–$C_{10}$ aromatic group, a heterocyclic group and an oxadiazole group represented by $R^2$], a heterocyclic group {said heterocyclic group is unsubstituted or substituted by one or more substituents selected from a $C_1$–$C_{10}$ alkyl group, a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_1$–$C_{10}$ acyl group {said acyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_1$–$C_{10}$ alkylcarbamoyl group {said alkylcarbamoyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_1$–$C_{10}$ alkoxycarbonyl group {said alkoxycarbonyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, a $C_6$–$C_{10}$ aryloxycarbonyl group {said aryloxycarbonyl group is unsubstituted or substituted by one or more substituents selected from a $C_1$–$C_{10}$ alkyl group, a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, $(CH_2)m^3COX^5R^{26}$ {in which $m^3$ represents 0, 1 or 2; $R^{25}$ has the same meaning as $R^1$; $X^5$ represents a covalent bond, an oxygen atom, a sulfur atom or $NR^{26}$ (in which $R^{26}$ has the same meaning as $R^{18}$)}, $(CH_2)n^5X^6R^{27}$ [in which $n^5$ represents 0, 1 or 2; $R^{27}$ has the same meaning as $R^1$, or it represents a nitro group, a cyano group, a formyl group, a guanidino group, an amidino group, a sulfonic acid group, a sulfonamide group, $PO_2H_2$, $PO_3H_2$, a 5-tetrazolyl group, or represents an oxadiazole group represented by $R^2$; $X^6$ represents a covalent bond, an oxygen atom, $S(O)n^6$ (in which $n^6$ represents 0, 1, 2 or 3), or $NR^{28}$ {in which $R^{28}$ has the same meaning as $R^{20}$ or represents $SO_2R^{29}$ (in which $R^{29}$ represents a $C_1$–$C_{10}$ alkyl group is unsubstituted or substituted by halogen atom(s))}], or $(CH_2)m^4X^7COR^{30}$ [in which $m^4$ represent 0, 1 or 2; $R^{30}$ represents a hydrogen atom, a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^{18}R^{18'}$ (in which $R^{18}$ and $R^{18'}$ each independently have the same meanings as defined above), $SR^{19}$ (in which $R^{19}$ has the same meaning as defined above), a $C_6$–$C_{10}$ aromatic group and a heterocyclic group}, or $NR^{31}R^{31'}$ (in which $R^{31}$ and $R^{31'}$ each independently have the same meanings as $R^{18}$); $X^7$ represents an oxygen atom, a sulfur atom or $NR^{32}$ (in which $R^{32}$ has the same meaning as $R^{18}$)]; $R^4$, $R^5$ and $R^6$ each independently represent a hydrogen atom, a halogen atom, a hydroxyl group, a nitro group, a cyano group, a formyl group, a guanidino group, an amidino group, a carboxyl group, a sulfonic acid group, a sulfonamide group, $PO_2H_2$, $PO_3H_2$, a 5-tetrazolyl group, a $C_1$–$C_{10}$ alkyl group {said alkyl group is unsubstituted or substituted by one or more substituents selected from a halogen atom, a hydroxyl group, a $C_1$–$C_{10}$ alkoxy group, $NR^{33}R^{33'}$ (in which $R^{33}$ and $R^{33'}$ each independently represent a hydrogen atom, a $C_1$–$C_{10}$ alkyl group or a $C_6$–$C_{10}$ aromatic group), $SR^{34}$ (in which $R^{34}$ has the same meaning as $R^{33}$), a $C_6$–$C_{10}$ aromatic group and a heterocyclic group}, a $C_1$–$C_{10}$ acyl group {said acyl group is unsubstituted or substituted by one or more substituents selected from a halogen atom, a hydroxyl group, a $C_1$–$C_{10}$ alkoxy group, $NR^{33}R^{33'}$ (in which $R^{33}$ and $R^{33'}$ each independently have the same meanings as defined above), $SR^{34}$ (in which $R^{34}$ has the same meaning as defined above), a $C_6$–$C_{10}$ aromatic group and a heterocyclic group}, a $C_1$–$C_{10}$ alkoxy group, or $NR^{33}R^{33'}$ (in which $R^{33}$ and $R^{33'}$ each independently have the same meanings as defined above);

$R^7$ represents a carboxyl group (said carboxyl group may be protected by a methyl group, a t-butyl group or the like), a sulfonic acid group, a sulfonamide group, $PO_2H_2$, $PO_3H_2$, a 5-tetrazolyl group (said tetrazolyl group may be protected by a triphenylmethyl group, a methoxymethyl group, a methoxyethoxymethyl group, a benzyl group or the like), an oxadiazole group represented by $R^2$, $X^8R^{35}$ {in which $R^{35}$ has the same meaning as $R^{12}$; $X^8$ represents an oxygen atom, a sulfur atom, $NR^{36}$ (in which $R^{36}$ has the same meaning as $R^{33}$), or $SO_2R^{37}$ (in which $R^{37}$ represents a $C_1$–$C_{10}$ alkyl group (said alkyl group is unsubstituted or substituted by halogen atom(s))}, a heterocyclic group {said heterocyclic group is unsubstituted or substituted by one or more substituents selected from a $C_1$–$C_{10}$ alkyl group, a halogen atom, a hydroxyl group, a $C_1$–$C_{10}$ alkoxy group, $NR^{38}R^{38'}$ (in which $R^{38}$ and $R^{38'}$ each independently represent a hydrogen atom, a $C_1$–$C_{10}$ alkyl group or a $C_6$–$C_{10}$ aromatic group), $SR^{39}$ (in which $R^{39}$ has the same meaning as $R^{38}$), a $C_6$–$C_{10}$ aromatic group and a heterocyclic group}, or a substituent of:

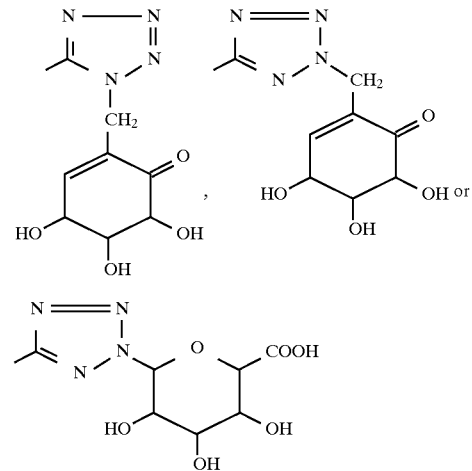

X represents a nitrogen atom or N→O;

Y and Z each independently represent a nitrogen atom or $CR^{40}$ (in which $R^{40}$ has the same meaning as $R^4$);

A represents $(CR^{41}R^{41'})m^7$-L—$(CR^{42}R^{42'})n^7$ {in which $m^7$ and $n^7$ each independently represent 0, 1, 2 or 3; $R^{41}$, $R^{41'}$, $R^{42}$ and $R^{42'}$ each independently have the same meanings as $R^4$;

L represents a covalent bond, an oxygen atom, a carbonyl group, $NR^{43}$ (in which $R^{43}$ represents a hydrogen atom, a $C_1$–$C_{10}$ alkyl group or a $C_6$–$C_{10}$ aromatic group), $NR^{44}$—CO (in which $R^{44}$ has the same meaning as $R^{43}$), CO—$NR^{46}$ (in which $R^{45}$ has the same meaning as $R^{43}$), $S(O)m^6$ (in which $m^6$ represents 0, 1 or 2), $NR^{46}$—CO—$NR^{47}$ (in which $R^{46}$ and $R^{47}$ each independently have the same meanings as $R^{43}$), $CR^{48}$=$CR^{49}$ (in which $R^{48}$ and $R^{49}$ each independently have the same meanings as $R^{43}$), C≡C, or $NR^{50}$—$NR^{51}$ (in which $R^{50}$ and $R^{51}$ each independently have the same meanings as $R^{43}$)};

D represents a $C_6$–$C_{10}$ aromatic group (said aromatic group is unsubstituted or mono-substituted to penta-substituted by one or more substituents represented by $R^3$);

E represents $(CR^{52}R^{53})m^6X^9$ {in which $m^6$ represents 0, 1 or 2; $R^{52}$ and $R^{53}$ each independently have the same meanings as $R^4$;

$X^9$ represents a covalent bond, an oxygen atom, a sulfur atom or $NR^{64}$ (in which $R^{54}$ represents a hydrogen atom, a $C_1$–$C_{10}$ alkyl group or a $C_6$–$C_{10}$ aromatic group)};

G represents a covalent bond, an oxygen atom, $S(O)m^8$ (in which $m^8$ represents 0, 1 or 2), $NR^{55}$ (in which $R^{55}$ represents a hydrogen atom, a $C_1$–$C_{10}$ alkyl group or a $C_6$–$C_{10}$ aromatic group), a carbonyl group, $(CR^{55}R^{56})n^8$ (in which $n^8$ represents 0, 1 or 2; $R^{55}$ and $R^{56}$ each independently represent a hydrogen atom, a $C_1$–$C_{10}$ alkyl group or a $C_6$–$C_{10}$ aromatic group), CO—$NR^{57}$ (in which $R^{57}$ represents a hydrogen atom, a $C_1$–$C_{10}$ alkyl group or a $C_6$–$C_{10}$ aromatic group), or $NR^{58}$—CO (in which $R^{58}$ represents a hydrogen atom, a $C_1$–$C_{10}$ alkyl group or a $C_6$–$C_{10}$ aromatic group)].

Examples of the substituents in the compounds of the above-mentioned formula [1] are mentioned below.

$C_1$–$C_{10}$ alkyl group includes, for example, a methyl group, an ethyl group, an n-propyl group, an i-propyl group, an n-butyl group, a sec-butyl group, a t-butyl group, an n-pentyl group, a neopentyl group, a hexyl group, etc.

$C_2$–$C_{10}$ alkenyl group includes, for example, a vinyl group, an allyl group, an i-propenyl group, a 1-butenyl group, a 2-butenyl group, a 3-butenyl group, a 1,3-butadienyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, a 5-hexenyl group, etc.

$C_2$–$C_{10}$ alkynyl group includes, for example, an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, a 5-hexynyl group, etc.

$C_3$–$C_{10}$ cycloalkyl group is meant to also include an alkylcycloalkyl group and a cycloalkylalkyl group, for example, including a c-propyl group, a c-butyl group, a c-pentyl group, a c-hexyl group, a 4-methyl-c-hexyl group, a c-propylmethyl group, etc.

$C_8$–$C_{10}$ cycloalkenyl group is meant to also include an alkylcycloalkenyl group and a cycloalkenylalkyl group, for example, including a 1-c-pentenyl group, a 2-c-pentenyl group, a 2,4-c-pentadienyl group, a 1-c-hexenyl group, a 2-c-hexenyl group, a 3-c-hexenyl group, a 4-methyl-1-c-hexenyl group, a 1-c-pentenylmethyl group, etc.

$C_6$–$C_{10}$ aromatic group includes, for example, a phenyl group, a 1-indenyl group, a 2-indenyl group, a 3-indenyl group, a 4-indenyl group, a 5-indenyl group, a 6-indenyl group, a 7-indenyl group, a 1-naphthyl group, a 2-naphthyl group, a 1-tetrahydronaphthyl group, a 2-tetrahydronaphthyl group, a 5-tetrahydronaphthyl group, a 6-tetrahydronaphthyl group, a 1-pentalenyl group, a 2-pentalenyl group, a 1-azulenyl group, a 2-azulenyl group, a 4-azulenyl group, a 5-azulenyl group, a 6-azulenyl group, etc.

Heterocyclic group is meant to include an aromatic heterocyclic group and a non-aromatic heterocyclic group.

As aromatic heterocyclic groups, mentioned are a 5-membered to 7-membered mono-heterocyclic group and a condensed bi-heterocyclic group having from 8 to 10 ring-constituting atoms, which contain from 1 to 5 hetero-atoms chosen from among oxygen, nitrogen and/or sulfur atoms.

As non-aromatic heterocyclic groups, mentioned are a 3-membered to 7-membered mono-heterocyclic group, a condensed bi-heterocyclic group having from 6 to 10 ring-constituting atoms and a crosslinked heterocyclic group having up to 10 ring-constituting atoms, which contain from 1 to 5 hetero-atoms chosen from among oxygen, nitrogen and/or sulfur atoms.

Aromatic heterocyclic group includes, for example, a 2-thienyl group, a 3-thienyl group, a 2-furyl group, a 3-furyl group, a 2-pyranyl group, a 3-pyranyl group, a 4-pyranyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, an 8-chromenyl group, a 1-pyrrolyl group, a 2-pyrrolyl group, a 3-pyrrolyl group, a 1-imidazolyl group, a 2-inidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 1-isoindolyl group, a 4-isoindolyl group, a 5-isoindolyl group, 1-indolyl group, a 2-indolyl group, a 3-indolyl group, 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, 3-purinyl group, a 6-purinyl group, a 7-purinyl group, an 8-purinyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 1-phthalazinyl group, a 5-phthalazinyl group, a 6-phthalazinyl group, a 2-naphthyridinyl group, a 3-naphthyridinyl group, a 4-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, an 8-quinazolinyl group, a 3-cinnolinyl group, a 4-cinnolinyl group, a 5-cinnolinyl group, a 6-cinnolinyl group, a 7-cinnolinyl group, an 8-cinnolinyl group, a 2-pteridinyl group, a 4-pteridinyl group, a 6-pteridinyl group, a 7-pteridinyl group, a 3-furazanyl group, etc. These groups is unsubstituted or substituted by one or more substituents selected from a hydroxyl group, a halogen atom, an oxo group (=O), an amino group, an alkyl group, etc.

Non-aromatic heterocyclic group includes, for example, a 2-chromanyl group, a 3-chromanyl group, a 4-chromanyl group, a 5-chromanyl group, a 6-chromanyl group, a 7-chromanyl group, an 8-chromanyl group, a 1-isochromanyl group, a 3-isochromanyl group, a 4-isochromanyl group, a 5-isochromanyl group, a 6-isochromanyl group, a 7-isochromanyl group, an 8-isochromanyl group, a 1-pyrrolidinyl group, a 2-pyrrolidinyl group, a 3-pyrrolidinyl group, a 1-pyrrolinyl group, a 2-pyrrolinyl group, a 3-pyrrolinyl group, a 4-pyrrolinyl group, a 5-pyrrolinyl group, a 1-imidazolidinyl group, a 2-imidazolidinyl group, a 4-imidazolidinyl group, a 1-imidazolinyl group, a 2-imidazolinyl group, a 4-imidazolinyl group, a 1-pyrazolidinyl group, a 3-pyrazolidinyl group, a 4-pyrazolidinyl group, a 1-pyrazolinyl group, a 2-pyrazolinyl group, a 3-pyrazolinyl group, a 4-pyrazolinyl group, a 5-pyrazolinyl group, a 1-piperidyl group, a 2-piperidyl group, a 3-piperidyl group, a 4-piperidyl group, a 1-piperazinyl group, a 2-piperazinyl group, a 3-piperazinyl group, a 1-indolinyl group, a 2-indolinyl group, a 3-indolinyl group, a 4-indolinyl group, a 5-indolinyl group, a 6-indolinyl group, a 7-indolinyl group, a 1-isoindolinyl group, a 2-isoindolinyl group, a 4-isoindolinyl group, a 5-isoindolinyl group, a 2-quinuclidinyl group, a 3-quinuclidinyl group, a 4-quinuclidinyl group, a 2-morpholinyl group, a 3-morpholinyl group, a 4-morpholinyl group, a 1-azetidinyl group, a 2-azetidinyl group, a 3-azetidinyl group, a 1-azetidinonyl group, a 3-azetidinonyl group, a 4-azetidinonyl group, etc. These groups may optionally be substituted by one or more substituents selected from a hydroxyl group, a halogen atom, an oxo group (=O), an amino group, an alkyl group, etc.

$C_1$–$C_{10}$ acyl group includes, for example, a formyl group, an acetyl group, a propionyl group, a butyryl group, an isobutyryl group, a valeryl group, an isovaleryl group, a pivaloyl group, an acryloyl group, a propioloyl group, a methacryloyl group, a crotonoyl group, a benzoyl group, a 2-furoyl group, a 3-furoyl group, a 2-thenoyl group, a 3-thenoyl group, a nicotinoyl group, a cyclopropylcarbonyl group, a hydroatropoyl group, a cinnamoyl group, etc.

$C_1$–$C_{10}$ alkylcarbamoyl group includes, for example, an N-methylcarbamoyl group, an N,N-dimethylcarbamoyl group, an N-ethylcarbamoyl group, an N-propylcarbamoyl group, an N-butyl-N-methylcarbamoyl group, an N-phenylcarbamoyl group, a succinamoyl group, etc.

$C_1$–$C_{10}$ alkoxycarbonyl group includes, for example, a methoxycarbonyl group, an ethoxycarbonyl group, an n-propoxycarbonyl group, an i-propoxycarbonyl group, an n-butoxycarbonyl group, a sec-butoxycarbonyl group, a t-butoxycarbonyl group, a benzyloxycarbonyl group, etc.

$C_6$–$C_{10}$ aryloxycarbonyl group includes, for example, a phenoxycarbonyl group, a 1-naphthyloxycarbonyl group, a 2-naphthyloxycarbonyl group, an 8-quinolinoxycarbonyl group, etc.

$C_1$–$C_{10}$ alkoxy group includes, for example, a methoxy group, an ethoxy group, an n-propoxy group, an i-propoxy group, an n-butoxy group, a sec-butoxy group, a t-butoxy group, a benzyloxy group, a phenoxy group, a 1-naphthyloxy group, a 2-naphthyloxy group, an 8-quinolinoxy group, etc.

Halogen atom includes fluorine atom, chlorine atom, bromine atom and iodine atom.

Pyrazole compounds of formula [1] and their tautomers and salts of the present invention may be produced according to the methods mentioned below.

Reaction Scheme (1)

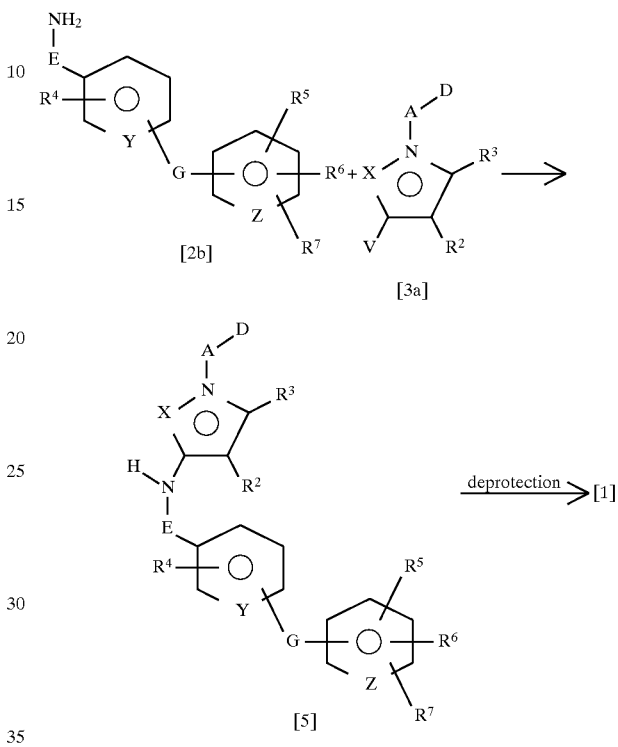

(In these formulae, $R^2$, $R^3$, $R^4$, $R^5$, $R^6$, $R^7$, A, D, E, G, X, Y and Z have the same meanings as defined above; V represents a halogen atom such as chlorine atom, bromine atom, iodine atom, etc., or a leaving group such as a methanesulfonyloxy group, a para-toluenesulfonyloxy group, a trifluoromethanesulfonyloxy group, etc.)

According to the reaction scheme (1), a compound of the formula [2b] is reacted with a compound of formula [3a] to give a compound of the formula [5] and, if necessary, the obtained compound is deprotected to produce a compound of the formula [1] wherein $R^1$ is a hydrogen atom.

Usually, the reaction may be effected in the presence of an inorganic base such as potassium carbonate, sodium carbonate, lithium carbonate, potassium hydrogencarbonate, sodium hydrogencarbonate, lithium hydroxide, etc. Apart from the above-mentioned inorganic bases, also employable are metal hydrides such as sodium hydride, potassium hydride, n-butyl lithium, etc.; metal alkoxides such as sodium methoxide, sodium ethoxide, potassium t-butoxide, etc.; metal amides such as sodium amide, lithium di-isopropylamide, lithium hexamethyldisilazide, lithium 2,2,6,6-tetramethylpiperidide, etc.; and organic bases such as trimethylamine, triethylamine, pyridine, diisopropylethylamine, etc.

Any reaction solvent that does not participate in the reaction may be employable. Usually, used are hydrocarbon solvents such as benzene, toluene, hexane, etc.; ether solvents such as tetrahydrofuran, diethyl ether, 1,4-dioxane, etc.; amide solvents such as formamide, N,N-dimethylformamide, N,N-dimethylacetamide, N-methylpyrrolidone, etc.; alcohol solvents such as methanol, ethanol, propanol, etc.; halogen-containing solvents such as chloroform, methylene chloride, ethylene dichloride, etc.; other solvents such as acetonitrile, dimethylsulfoxide, etc.; water; and mixed solvents comprising two or more of them.

The reaction temperature may be within the range of from −78° C. to the boiling point of the solvent used in the reaction.

The molar ratio of the starting compounds may be defined freely. In general, the compound of the formula [2b] may be reacted with the compound of formula [3a] in an amount of from 0.8 to 1.5 times by mol the latter.

The deprotection may be effected by known methods. For example, the methyl ester or ethyl ester residue in the protected intermediate may be removed by reacting the intermediate with sodium hydroxide, potassium hydroxide or the like in a water-alcohol solvent while cooling with ice or at room temperature or lower. The triphenylmethyl group in the same may be removed by treating the intermediate with an aqueous acetic acid or hydrochloric acid-ethanol or with ethanol under reflux.

The benzyl group may be removed by hydrogenolysis of the protected intermediate with hydrogen gas, using a Pd-carbon catalyst; and the methoxymethyl ether residue may be removed by treating the intermediate with hydrochloric acid-ethanol.

Reaction Scheme (2):

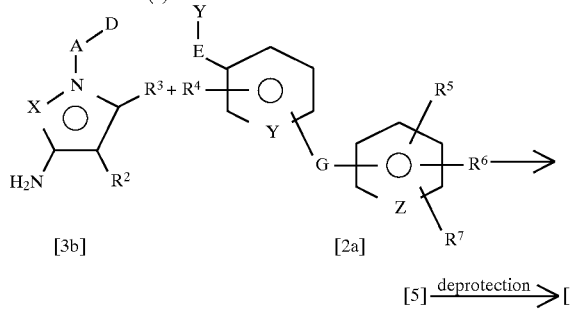

(In these formulae, $R^2$, $R^3$, $R^4$, $R^5$, $R^6$, $R^7$, A, D, E, G, X, Y, Z and V have the same meanings as defined above.)

According to the reaction scheme (2), a compound of the formula [3b] is reacted with a compound of the formula [2a] to give a compound of formula [5] and if necessary, this compound is deprotected to produce a compound of the formula [1] wherein $R^1$ is a hydrogen atom.

The reaction may be conducted under the same conditions as those for the reaction scheme (1). The conditions for the deprotection are the same as those defined above.

The molar ratio of the starting compounds may be defined freely. Usually, the compound of the formula [3b] may be reacted with the compound of the formula [2a] in an amount of from 0.8 to 1.5 times by mol the latter.

Reaction Scheme (3):

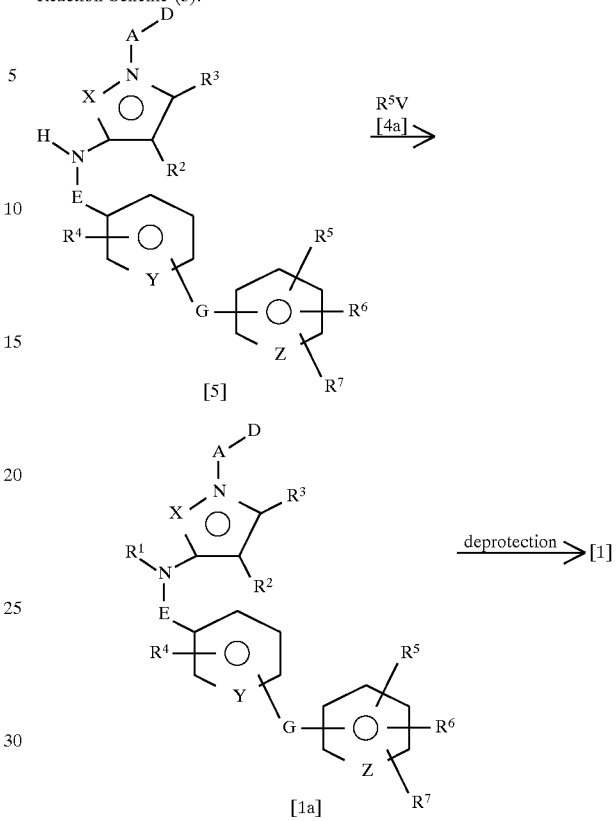

(In these formulae, $R^1$, $R^2$, $R^3$, $R^4$, $R^5$, $R^6$, $R^7$, A, D, E, G, X, Y and Z have the same meanings as defined above; V represents a halogen atom or a leaving group such as chlorine atom, bromine atom, iodine atom, a methanesulfonyloxy group, a para-toluenesulfonyloxy group, a trifluoromethanesulfonyloxy group, etc. when $R^1$ is a hydrogen atom, an alkyl group, an alkenyl group, an alkynyl group or an aralkyl group, while V represents a halogen atom such as chlorine atom, bromine atom, iodine atom, etc., or a methoxy group, an ethoxy group, a methylthio group, an ethylthio group, etc. when $R^1$ is an acyl group.)

According to the reaction scheme (3), a compound of the formula [5] is reacted with a compound of the formula [4a] to give a compound of the formula [1a] and, if necessary, the obtained compound is deprotected to produce a compound of the formula [1] wherein $R^1$ represents the substituents other than hydrogen atom. The reaction may be conducted under the same conditions as those for the reaction scheme (1). The conditions for the deprotection are the same as those defined above.

Reaction Scheme (4):

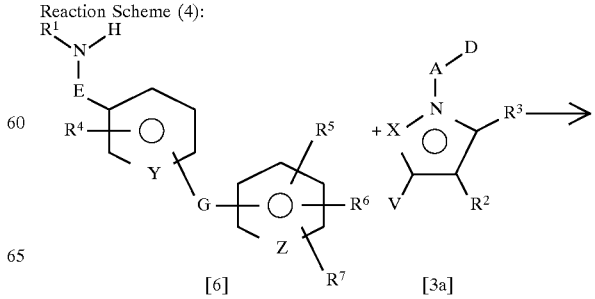

Reaction Scheme (4):

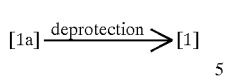

(In these formulae, $R^1$, $R^2$, $R^3$, $R^4$, $R^5$, $R^6$, $R^7$, A, D, E, G, X, Y, Z and V have the same meanings as defined above.)

According to the reaction scheme (4), a compound of the formula [6] is reacted with a compound of the formula [3a] to give a compound of the formula [1a] and, if necessary, the obtained compound is deprotected to produce a compound of the formula [1] wherein $R^1$ represents the substituents other than hydrogen atom. The reaction may be conducted under the same conditions as those for the reaction scheme (1). The conditions for the deprotection are the same as those defined above.

Reaction Scheme (5):

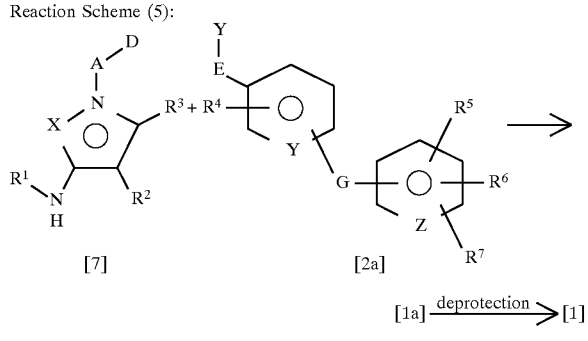

(In these formulae, $R^1$, $R^2$, $R^3$, $R^4$, $R^5$, $R^6$, $R^7$, A, D, E, G, X, Y, Z and V have the same meanings as defined above.)

According to the reaction scheme (5), a compound of the formula [7] is reacted with a compound of the formula [2a] to give a compound of the formula [1a] and, if necessary, the obtained compound is deprotected to produce a compound of the formula [1] wherein $R^1$ represents the substituents other than hydrogen atom. The reaction may be conducted under the same conditions as those for the reaction scheme (1). The conditions for the deprotection are the same as those defined above.

Reaction Scheme (6):

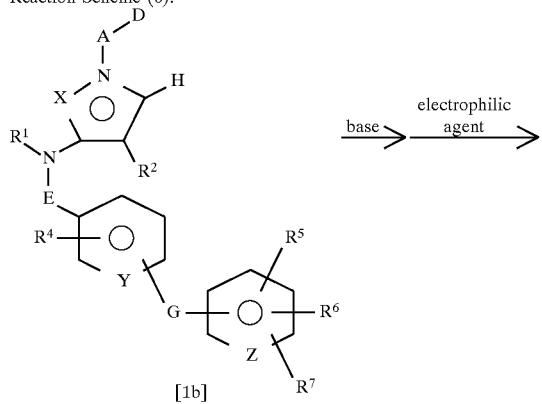

Reaction Scheme (6):

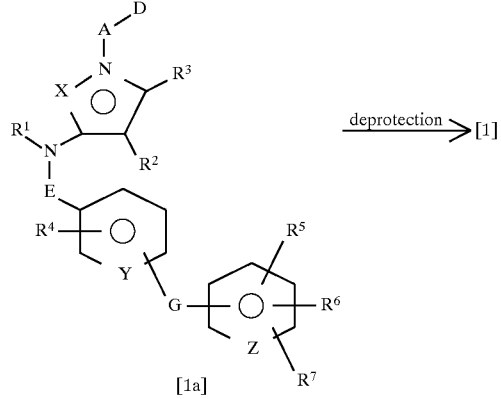

(In these formulae, $R^1$, $R^2$, $R^3$, $R^4$, $R^5$, $R^6$, $R^7$, A, D, E, G, X, Y and Z have the same meanings as defined above.)

According to the reaction scheme (6), a compound of the formula [1b] is reacted with a base to thereby remove its 5-positioned hydrogen atom therefrom, the resulting compound is then reacted with an electrophilic agent to produce a compound of the formula [1a], and, if necessary, the obtained compound is deprotected to obtain a compound of the formula [1].

Usually, the reaction may be conducted, using, as the base, a metal amide such as lithium diisopropylamide, lithium hexamethyldisilazide, lithium 2,2,6,6-tetramethylpiperidide, etc.; an alkali metal such as lithium, sodium, etc.; a metal hydride such as potassium hydride, etc.; or an alkyl metal such as methyl lithium, n-butyl lithium, etc.

As the electrophilic agent, usable are halogens such as fluorine, chlorine, bromine, iodine, etc.; alkyl halides such as 1,1,2,2-tetrafluoro-1,2-dibromoethane, 1,2-dibromoethane, methyl iodide, propyl iodide, etc.; isocyanates such as methyl isocyanate, cyclohexyl isocyanate, etc.; acid halides such as acetyl chloride, ethyl chloroformate, etc.; amides such as N-methoxy-N-methylbenzoylamide, dimethylformamide, etc.; esters such as ethyl acetate, triethyl borate, etc.; carbon dioxide, etc.

The reaction conditions such as the reaction solvent, the reaction temperature and the molar ratio of the starting compounds may be the same as those for the reaction scheme (1). The conditions for the deprotection are the same as those defined above.

Reaction Scheme (7):

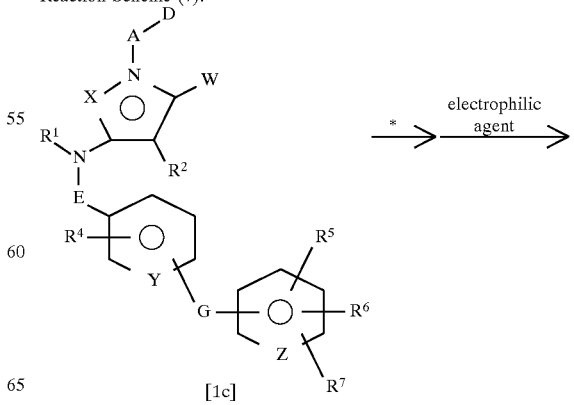

-continued

Reaction Scheme (7):

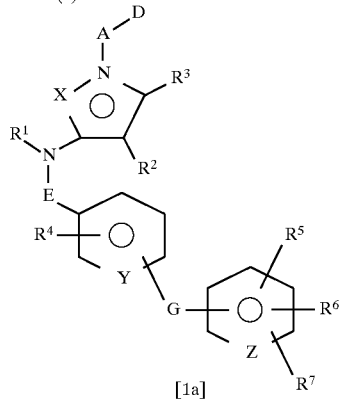

(* organic lithium compound or alkali metal)

(In these formulae, $R^1$, $R^2$, $R^3$, $R^4$, $R^5$, $R^6$, $R^7$, A, D, E, G, X, Y and Z have the same meanings as defined above; W represents a halogen atom such as chlorine, bromine, iodide, etc.)

According to the reaction scheme (7), a compound of the formula [1c] is subjected to halogen-metal exchanging reaction at its 5-positioned halogen, using an organolithium reagent or an alkali metal, the resulting compound is then reacted with an electrophilic agent in the absence or presence of a catalyst to synthesize a compound of the formula [1a], and, if necessary, the obtained compound is deprotected to obtain a compound of the formula [1].

Usually, the reaction may be conducted, using an organolithium reagent such as butyl lithium, methyl lithium, etc., or an alkali metal such as lithium, sodium, potassium, etc.

As the catalyst, if desired, usable are palladium catalysts such as tetrakis(triphenylphosphine) palladium(0), palladium(II) chloride, etc.; nickel catalysts such as dichloro [1,3-bis(diphenylphosphine)propane] nickel(II), tetrakis (tri-p-tolylphosphite) nickel(0), etc.; ruthenium catalysts such as dichloro-tris(triphenylphosphine) ruthenium, etc.; and rhodium catalysts such as chloro-tris (triphenylphosphine) rhodium, etc.

This reaction may be conducted under the same conditions as those for the reaction scheme (6). The conditions for the deprotection are the same as those defined above.

Reaction Scheme (8):

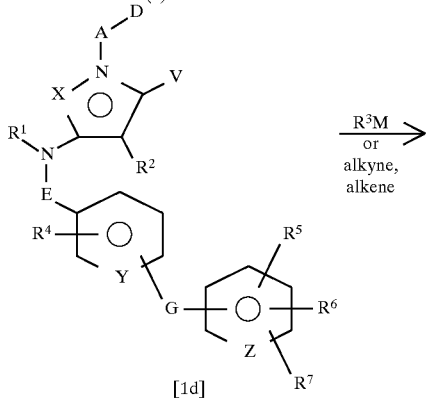

-continued

Reaction Scheme (8):

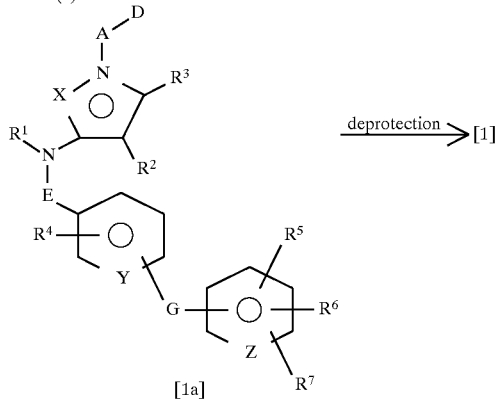

(In these formulae, $R^1$, $R^2$, $R^3$, $R^4$, $R^5$, $R^6$, $R^7$, A, D, E, G, X, Y, Z and V have the same meanings as defined above.)

According to the reaction scheme (8), a compound of the formula [1d] is reacted with an organometallic reagent or an alkyne or alkene in the absence or presence of a catalyst to synthesize a compound of the formula [1a], and, if necessary, the obtained compound is deprotected to obtain a compound of the formula [1].

As the organometallic reagent in this reaction, usable are organolithium reagents such as methyl lithium, n-butyl lithium, phenyl lithium, 4-methylphenyl lithium, etc.; organomagnesium reagents such as methyl magnesium bromide, phenyl magnesium bromide, etc.; organoaluminium reagents such as diisobutyl-1-hexenyl aluminium, etc.; organozinc reagents such as methyl zinc bromide, phenyl zinc bromide, etc.; organotin reagents such as trimethylvinyl tin, etc.; organoboron reagents such as 3-methylphenylboric acid, etc.; organocopper reagents such as methyl copper, phenyl copper, lithium methylcuprate, etc.; metal alkoxides such as sodium methoxide, sodium phenoxide, etc.; metal mercaptides such as sodium methylmercaptide, sodium phenylmercaptide, etc. Also usable are alkynes such as phenylacetylene, trimethylsilylacetylene, etc.; and alkenes such as acrolein, acrylonitrile, etc.

As the catalyst, if desired, usable are palladium catalysts such as tetrakis(triphenylphosphine) palladium(0), palladium(II) chloride, etc.; nickel catalysts such as dichloro [1,3-bis(diphenylphosphine)propane] nickel(II), tetrakis (tri-p-tolylphosphite) nickel(0), etc.; ruthenium catalysts such as dichloro-tris(triphenylphosphine) ruthenium, etc.; and rhodium catalysts such as chloro-tris (triphenylphosphine) rhodium, etc.

This reaction may be conducted under the same conditions as those for the reaction scheme (6). The conditions for the deprotection are the same as those defined above.

Reaction Scheme (9)

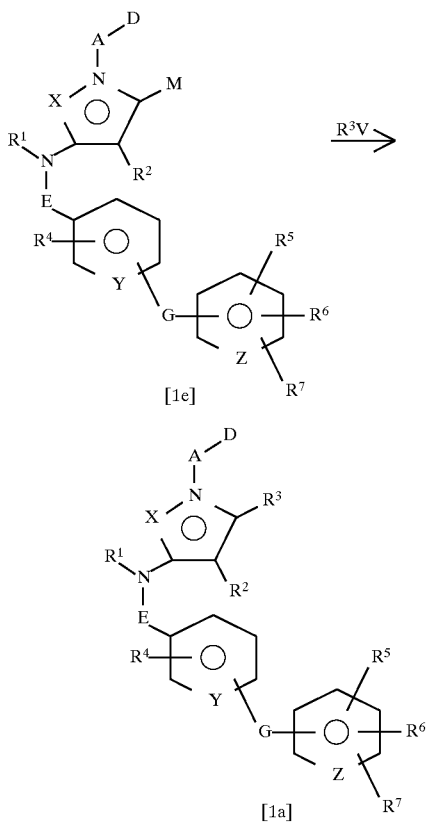

Reaction Scheme (10):

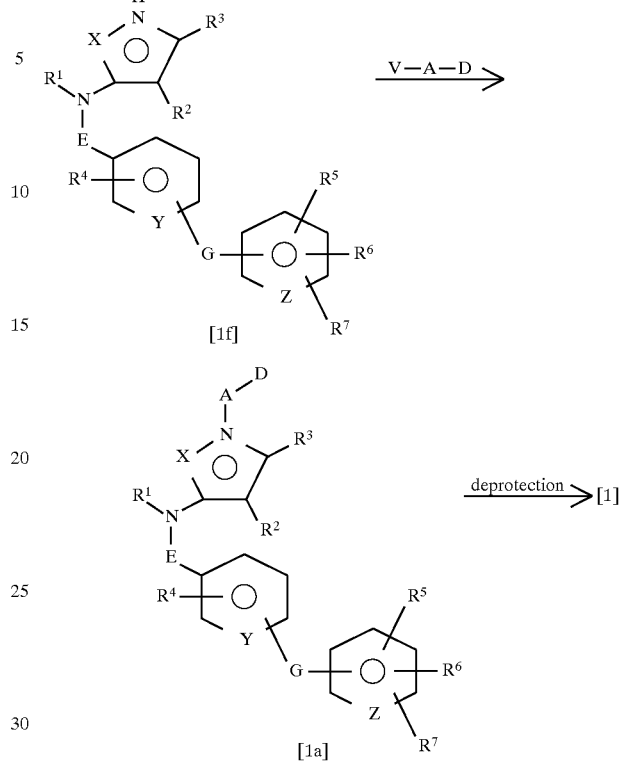

(In these formulae, $R^1$, $R^2$, $R^3$, $R^4$, $R^5$, $R^6$, $R^7$, A, D, E, G, X, Y, Z and V have the same meanings as defined above; M represents a metal atom such as lithium, copper, etc., a metal halide such as zinc chloride, magnesium bromide, etc., an alkyl metal such as trimethyl tin, tributyl tin, etc., or boric acid.)

According to the reaction scheme (9), a compound of the formula [1e] is reacted with an organic halide in the absence or presence of a catalyst to synthesize a compound of the formula [1a], and optionally this is deprotected to obtain a compound of the formula [1].

As the organic halide, usable are alkyl halides such as methyl iodide, propyl iodide, etc.; aryl halides such as phenyl iodide, 2-bromobenzonitrile, etc.; alkene halides such as vinyl bromide, etc.

As the catalyst, if desired, usable are palladium catalysts such as tetrakis(triphenylphosphine) palladium(0), palladium(II) chloride, etc.; nickel catalysts such as dichloro[1,3-bis(diphenylphosphine)propane] nickel(II), tetrakis(tri-p-tolylphosphite) nickel(0), etc.; ruthenium catalysts such as dichloro-tris(triphenylphosphine) ruthenium, etc.; and rhodium catalysts such as chloro-tris(triphenylphosphine) rhodium, etc.

This reaction may be conducted under the same conditions as those for the reaction scheme (6). The conditions for the deprotection are the same as those defined above.

(In these formulae, $R^1$, $R^2$, $R^3$, $R^4$, $R^5$, $R^6$, $R^7$, A, D, E, G, X, Y, Z and V have the same meanings as defined above.)

According to the reaction scheme (10), a compound of the formula [1f] is reacted with an alkyl halide or acid halide in the absence or presence of a catalyst to produce a compound of the formula [1a], and, if necessary, the obtained compound is deprotected to obtain a compound of the formula [1].

This reaction may be normally conducted in the presence of an inorganic base such as potassium carbonate, sodium carbonate, lithium carbonate, potassium hydrogencarbonate, sodium hydrogencarbonate, lithium hydroxide, etc.

Apart from the above-mentioned inorganic bases, also employable are metal hydrides such as sodium hydride, potassium hydride, n-butyl lithium, etc.; metal alkoxides such as sodium methoxide, sodium ethoxide, potassium t-butoxide, etc.; metal amides such as sodium amide, lithium diisopropylamide, lithium hexamethyldisilazide, lithium 2,2,6,6-tetramethylpiperidide, etc.; and organic bases such as trimethylamine, triethylamine, pyridine, diisopropylethylamine, etc.

To conduct this reaction, a quaternary ammonium halide such as Adogen 464 [methyltrialkyl($C_{8-10}$) ammonium chloride; trade name by Ashland Chemical Co.] or the like may be used as the catalyst, if desired. This reaction may be conducted under the same conditions as those for the reaction scheme (6). The conditions for the deprotection are the same as those mentioned above.

Reaction Scheme (11):

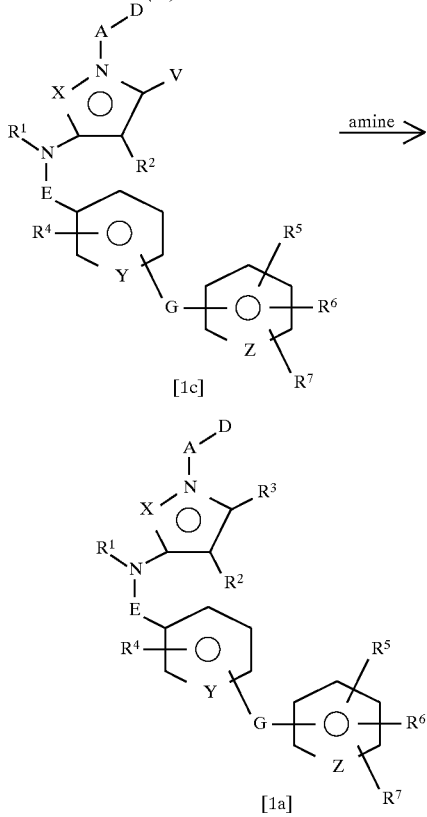

(In these formulae, $R^1$, $R^2$, $R^3$, $R^4$, $R^5$, $R^6$, $R^7$, A, D, E, G, X, Y, Z and V have the same meanings as defined above.)

According to the reaction scheme (11), a compound of the formula [1c] is reacted with a primary or secondary amine to give a compound of the formula [1a], and, if necessary, the obtained compound is deprotected to produce a compound of the formula [1].

This reaction may be generally conducted in the presence of an inorganic base such as potassium carbonate, sodium carbonate, lithium carbonate, potassium hydrogencarbonate, sodium hydrogencarbonate, lithium hydroxide, etc.

As the catalyst for the reaction, if desired, usable are copper catalysts such as copper, copper(I) oxide, copper(II) oxide, etc., singly or as a combination of them.

As the amine, usable are alkylamines such as n-propylamine, n-butylamine, diethylamine, etc., and arylamines such as aniline, etc.

This reaction may be conducted under the same conditions as those for the reaction scheme [1]. The conditions for the deprotection are the same as those defined above.

Compounds of the formulae [6] and [7] which are used as the starting compounds in the above-mentioned methods may be produced, for example, according to the methods defined below.

Reaction Scheme (12):

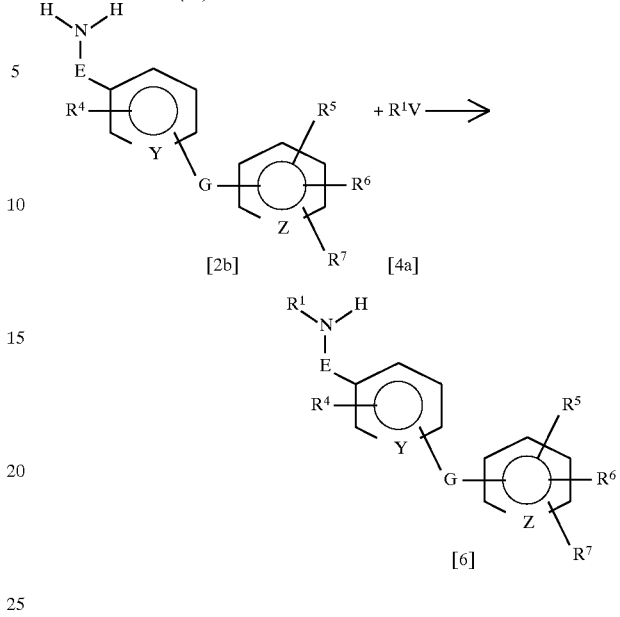

(In these formulae, $R^1$, $R^4$, $R^5$, $R^6$, $R^7$, E, G, Y, Z and V have the same meanings as defined above.)

According to the reaction scheme (12), a compound of the formula [2b] is reacted with a compound of the formula [4a] to synthesize a compound of formula [6]. This reaction may be conducted under the same conditions as those for the reaction scheme (3).

Reaction Scheme (13):

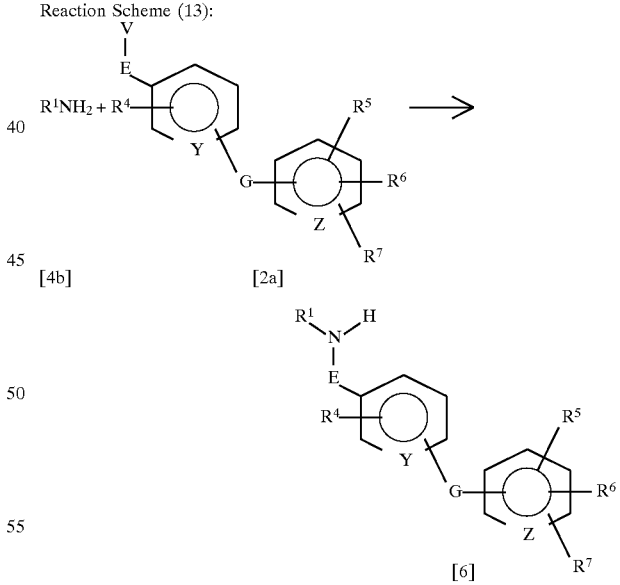

(In these formulae, $R^1$, $R^4$, $R^5$, $R^6$, $R^7$, E, G, Y, Z and V have the same meanings as defined above.)

According to the reaction scheme (13), a compound of the formula [4b] is reacted with a compound of the formula [2a] to synthesize a compound of the formula [6]. This reaction may be conducted under the same conditions as those for the reaction scheme (1).

Reaction Scheme (14):

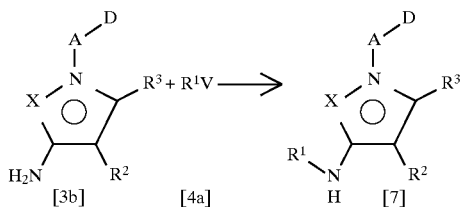

(In these formulae, $R^1$, $R^2$, $R^3$, A, D, X and V have the same meanings as defined above.)

According to the reaction scheme (14), a compound of the formula [3b] is reacted with a compound of the formula [4a] to synthesize a compound of the formula [7]. This reaction may be conducted under the same conditions as those for the reaction scheme (2).

Reaction Scheme (15):

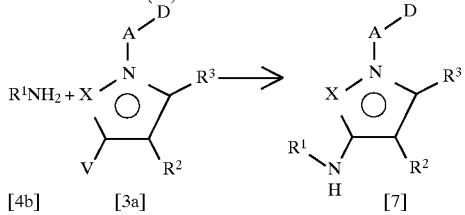

(In these formulae, $R^1$, $R^2$, $R^3$, A, D, X and V have the same meanings as defined above.)

According to the reaction scheme (15), a compound of the formula [4b] is reacted with a compound of the formula [3a] to synthesize a compound of the formula [7]. This reaction may be conducted under the same conditions as those for the reaction scheme (1).

Next, methods for producing compounds of the formulae [3a] and [3b] which are the starting compounds in the above-mention methods will be explained below.

Of compounds of formula [3b], those of formula [11] wherein X is a nitrogen atom may be synthesized according to the methods described in, for example, Z. Chem., 8, 420 (1969); Aust. J. Chem., 36, 135 (1983); Org. Prep. Proded. Int., 17, 70 (1985); J. Heterocycl. Chem., 19, 1265 (1982); J. Heterocycl. Chem., 19, 1267 (1982); J. Med. Chem., 7, 259 (1964); J. Heterocycl. Chem., 17, 73 (1980); Monatsh. Chem., 112, 875 (1981); Tetrahedron Lett., 2991 (1979); Chem. Ber., 98, 2576 (1965); Helv. Chim. Acta, 42, 763 (1959), etc.

Reaction Scheme (16):

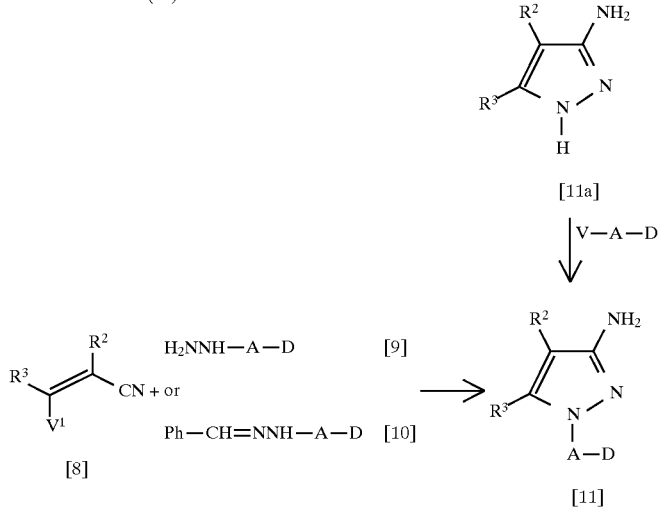

[In these formulae, $R^2$, $R^3$, A, D and V have the same meanings as defined above; $V^1$ represents a halogen atom (e.g., chlorine, bromine, etc.), a hydroxyl group, an alkoxy group (e.g.,methoxy, ethoxy, etc.), or an amino group (e.g., $NH_2$, $NMe_2$, NHPh, etc.).]

Briefly, a compound of the formula [8] is reacted with a compound of the formula [9] or [10] to synthesize a compound of the formula [11]; or alternatively, a compound of the formula [11a] is reacted with a compound of V-A-D in a homogeneous system or a two-layer system to synthesize the same.

Of compounds of the formula [3b], those of the formula [14] wherein X is a nitrogen atom may be produced according to the methods described in, for example, J. Amer. Chem. Soc., 78, 784 (1956); J, Org. Chem., 21, 1240 (1956); EP-320765; J. Prakt. Chem., 331, 552 (1989); DD-248587; J. Heterocycl. Chem., 23, 1035 (1986); J. Heterocycl.

Chem., 22, 1093 (1985); Synthesis, 794 (1985); Synthesis, 3, 276 (1984); EP-53698; EP-53699; EP-53678; Chem. Ber., 114, 2834 (1981); DD-149517; J. Gen. Chem., USSR 50, 2116 (1980); J. Heterocycl. Chem, 17, 1527 (1980); J. Heterocycl. Chem., 11, 423 (1974); J. Chem. Soc., C 1501 (1971); J. Chem. Soc., C 1610 (1971); Helv. Chim. Acta, 36, 86 (1956); Liebigs Ann. Chem., 339, 117 (1905), etc.

phosphorus oxyhalide, or reacting a compound of the formula [16] and a diazo compound, or diazoating a compound of the formula [11] followed by reacting the resulting diazo compound and a copper halide.

Of compounds of the formula [3a], those of the formula [22] wherein X is a nitrogen atom may be produced according to the methods described in, for example, J. Chem. Soc., Reaction Scheme (17):

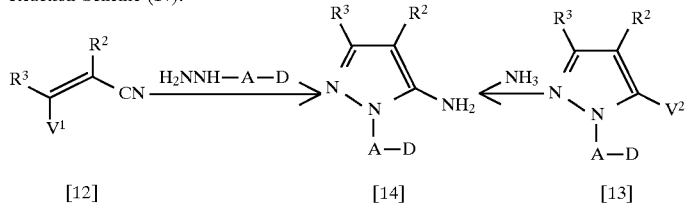

(In these formulae, $R^2$, $R^3$, A, D and V have the same meanings as defined above.)

Briefly, a compound of the formula [12] is reacted with hydrazine to synthesize a compound of the formula [14], or alternatively, a compound of the formula [13] is reacted with ammonia to synthesize the same.

Of compounds of the formula [3a], those of formula [17] wherein X is a nitrogen atom may be produced according to the methods described in, for example, J. Chem. Soc C 1507 (1968); J. Org. Chem., 25, 1259 (1960); J. Amer. Chem. Soc., 73, 4664 (1951); Gazz. Chim. Ital., 78, 332 (1948); Liebigs Ann. Chem., 338, 183 (1905); Liebigs Ann. Chem., 338, 267 (1905), etc.

2769 (1961); Bull. Chem. Soc. Jpn., 46, 1572 (1973); J. Amer. Chem. Soc., 73, 4664 (1951); J. Amer. Chem. Soc., 76, 3686 (1954); J. Heterocycl. Chem., 26, 241 (1989); Acta Chem. Scand., 33, 483 (1979); J. Org. Chem., 36, 2542 (1971); Bull. Soc. Chim. Fr., 1974 (1970); J. Chem. Soc. C 1507 (1968); J. Gen. Chem., USSR 30, 3251 (1960); J. Pharm. Soc., Japan, 61, 26 (1941); J. Chem. Soc., 1739 (1934); J. Chem. Soc., 475 (1933); Liebigs Ann. Chem., 338, 183 (1905); Chem. Ber., 33, 2595 (1900); J. Heterocycl. Chem., 28, 1545 (1991), etc.

Reaction Scheme (18):

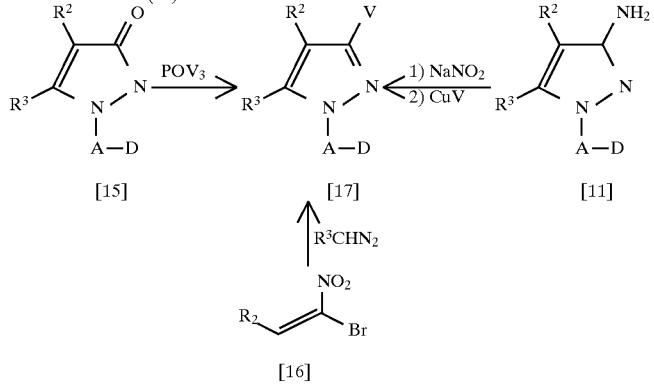

(In these formulae, $R^2$, $R^3$, A, D and V have the same meanings as defined above.)

Briefly, a compound of the formula [17] may be synthesized by reacting a compound of the formula [15] and a Reaction Scheme (19):

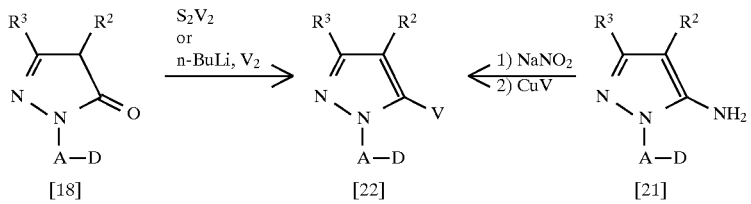

Reaction Scheme (19):

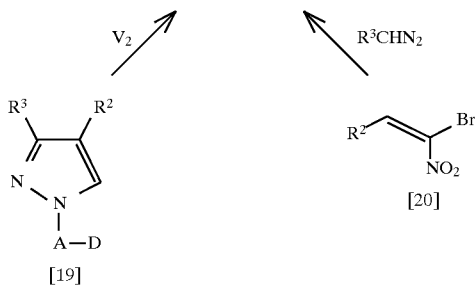

(In these formulae, $R^2$, $R^3$, A, D and V have the same meanings as defined above.)

Briefly, a compound of the formula [22] may be synthesized by reacting a compound of the formula [18] and a phosphorus oxyhalide, or reacting a compound of the formula [19] and a halogen (e.g., chlorine, bromine), or reacting a compound of the formula [20] and a diazo compound, or diazoating a compound of the formula [21] followed by reacting the resulting diazo compound and a copper halide.

Of compounds of the formula [3a], those of the formula [24] wherein X is a nitrogen atom may be produced according to the methods described in, for example, J. Med. Chem., 32, 2573 (1989), etc.

Reaction Scheme (20):

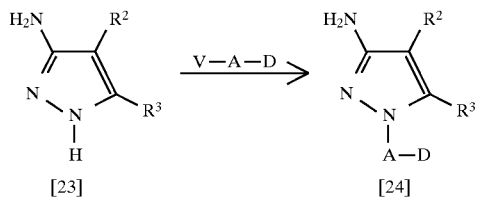

(In these formulae, $R^2$, $R^3$, A, D and V have the same meanings as defined above.)

Briefly, a compound of the formula [23] is reacted with an alkyl halide in the presence of an aqueous solution of Adogen 464, potassium carbonate or sodium hydroxide in toluene to synthesize a compound of the formula [24].

As the routes for administering the pyrazole compounds of the formula [1] and their tautomers and salts of the present invention, they may be administered parenterally as injection (subcutaneous, intravascular, intramuscular or intraabdominal injection), ointment, suppositories, aerosol, etc., or orally as tablets, capsules, granules, pills, syrup, solution, emulsion, suspension, etc.

The medicinal compositions of the present invention contain at least one of the above-mentioned compounds of the formula [1] and their tautomers and salts in an amount of approximately from 0.1 to 99.5% by weight as the compound of the formula [1], preferably approximately from 0.5 to 95% by weight as the same, relative to the total weight of the composition. The compounds of the formula [1] and the compositions containing them may contain other pharmacologically active compounds. The compositions may contain a plurality of the compounds of the formula [1].

The clinical dose of the compounds of the formula [1] to be administered to patients varies, depending on the age, the body weight, the sensitivity and the condition of the patient. Usually, the effective dose of the compound of the formula [1] for an adult is approximately from 0.003 to 1.5 g/day, preferably approximately from 0.01 to 0.6 g/day. If desired, however, doses which are outside the defined range may also be employed.

The compounds of the formula [1] may be formulated into pharmaceutical preparations in accordance with conventional methods commonly employed for the preparations of pharmaceutical formulations.

Namely, tablets, capsules, granules or pills for oral administration, may be prepared by using excipients such as white sugar, lactose, glucose, starch or mannitol; binders such as syrup, arabic gum, gelatin, sorbitol, tragacanth gum, methyl cellulose or polyvinylpyrrolidone; disintegrators such as starch, carboxymethyl cellulose or its calcium salt, crystal cellulose powder or polyethylene glycol; lubricants such as talc, magnesium or calcium stearate, silica; and smoothers such as sodium laurate, glycerol, etc.

The injections, solutions, emulsions, suspensions, syrups and aerosol may be prepared using a solvent for the active ingredient such as water, ethyl alcohol, isopropyl alcohol, propylene glycol, 1,3-butylene glycol or polyethylene glycol; surfactants such as sorbitan fatty acid esters, polyoxyethylene sorbitan fatty acid esters, polyoxyethylene fatty acid esters, polyoxyethylene ether of hydrogenated castor oil, lecithin; suspending agents such as cellulose derivatives such as sodium carboxymethyl cellulose and methyl cellulose or natural rubbers such as tragacanth or arabic gum; preservatives such as para-hydroxybenzoates, benzalkonium chloride, salts of sorbic acid, etc. The suppositories may be prepared by using, cacao butter, polyethylene glycol, lanolin, coconut oil, etc.

As examples of the compounds of the present invention, mentioned are the compounds described in Tables 1 to 5 below and their pharmacologically acceptable salts, in addition to the compounds produced in the examples which follow hereunder.

In the tables, "n-" means normal; "i-" means iso; "c-" means cyclo; "sec-" means secondary; "t-" means tertiary; "Me" means methyl; "Et" means ethyl; "Pr" means propyl; "Bu" means butyl; "Pen" means pentyl; "Hex" means hexyl; "Ph" means phenyl; and "Bz" means benzyl. In these, $J^1$=NHCOEt; $J^2$=N(n-Pen)COPh; U=COOH; and T means the following substituent.

TABLE 1

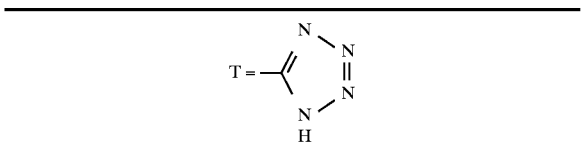

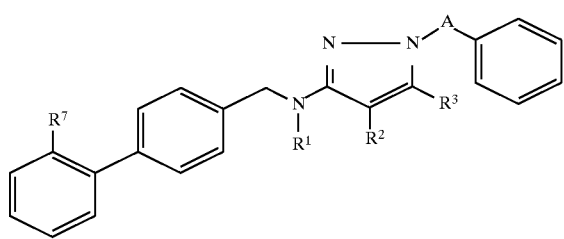

| R¹ | R² | R³ | R⁷ | A |
|---|---|---|---|---|
| n-Pr | U | F | T | — |
| n-Pr | U | Cl | T | — |
| n-Pr | U | Br | T | — |
| n-Pr | U | I | T | — |
| n-Pr | U | Me | T | — |
| n-Pr | U | CF₃ | T | — |
| n-Pr | U | Et | T | — |
| n-Pr | U | n-Pr | T | — |
| n-Pr | U | NO₂ | T | — |
| n-Pr | U | NH₂ | T | — |
| n-Pr | U | NHCOPh | T | — |
| n-Pr | U | CHO | T | — |
| n-Pr | U | CN | T | — |
| n-Pr | U | Ph | T | — |
| n-Pr | U | F | T | CH₂ |
| n-Pr | U | Cl | T | CH₂ |
| n-Pr | U | Br | T | CH₂ |
| n-Pr | U | I | T | CH₂ |
| n-Pr | U | Me | T | CH₂ |
| n-Pr | U | CF₃ | T | CH₂ |
| n-Pr | U | Et | T | CH₂ |
| n-Pr | U | n-Pr | T | CH₂ |
| n-Pr | U | NO₂ | T | CH₂ |
| n-Pr | U | NH₂ | T | CH₂ |
| n-Pr | U | NHCOPh | T | CH₂ |
| n-Pr | U | CHO | T | CH₂ |
| n-Pr | U | CN | T | CH₂ |
| n-Pr | U | Ph | T | CH₂ |
| Et | U | F | T | CH₂ |
| Et | U | Cl | T | CH₂ |
| Et | U | Br | T | CH₂ |
| Et | U | I | T | CH₂ |
| Et | U | Me | T | CH₂ |
| Et | U | CF₃ | T | CH₂ |
| Et | U | Et | T | CH₂ |
| Et | U | n-Pr | T | CH₂ |
| Et | U | NO₂ | T | CH₂ |
| Et | U | NH₂ | T | CH₂ |
| Et | U | NHCOPh | T | CH₂ |
| Et | U | CHO | T | CH₂ |
| Et | U | CN | T | CH₂ |
| Et | U | Ph | T | CH₂ |
| n-Bu | U | F | T | CH₂ |
| n-Bu | U | Cl | T | CH₂ |
| n-Bu | U | Br | T | CH₂ |
| n-Bu | U | I | T | CH₂ |
| n-Bu | U | Me | T | CH₂ |
| n-Bu | U | CF₃ | T | CH₂ |
| n-Bu | U | Et | T | CH₂ |
| n-Bu | U | n-Pr | T | CH₂ |
| n-Bu | U | NO₂ | T | CH₂ |
| n-Bu | U | NH₂ | T | CH₂ |
| n-Bu | U | NHCOPh | T | CH₂ |
| n-Bu | U | CHO | T | CH₂ |
| n-Bu | U | CN | T | CH₂ |
| n-Bu | U | Ph | T | CH₂ |
| c-Pr | U | F | T | CH₂ |
| c-Pr | U | Cl | T | CH₂ |
| c-Pr | U | Br | T | CH₂ |
| c-Pr | U | I | T | CH₂ |
| c-Pr | U | Me | T | CH₂ |
| c-Pr | U | CF₃ | T | CH₂ |
| c-Pr | U | Et | T | CH₂ |
| c-Pr | U | n-Pr | T | CH₂ |
| c-Pr | U | NO₂ | T | CH₂ |
| c-Pr | U | NH₂ | T | CH₂ |
| c-Pr | U | NHCOPh | T | CH₂ |
| c-Pr | U | CHO | T | CH₂ |
| c-Pr | U | CN | T | CH₂ |
| c-Pr | U | Ph | T | CH₂ |
| n-Pr | U | F | T | (CH₂)₃ |
| n-Pr | U | Cl | T | (CH₂)₃ |
| n-Pr | U | Br | T | (CH₂)₃ |
| n-Pr | U | I | T | (CH₂)₃ |
| n-Pr | U | Me | T | (CH₂)₃ |
| n-Pr | U | CF₃ | T | (CH₂)₃ |
| n-Pr | U | Et | T | (CH₂)₃ |
| n-Pr | U | n-Pr | T | (CH₂)₃ |
| n-Pr | U | NO₂ | T | (CH₂)₃ |
| n-Pr | U | NH₂ | T | (CH₂)₃ |
| n-Pr | U | NHCOPh | T | (CH₂)₃ |
| n-Pr | U | CHO | T | (CH₂)₃ |
| n-Pr | U | CN | T | (CH₂)₃ |
| n-Pr | U | Ph | T | (CH₂)₃ |
| Et | U | F | T | (CH₂)₃ |
| Et | U | Cl | T | (CH₂)₃ |
| Et | U | Br | T | (CH₂)₃ |
| Et | U | I | T | (CH₂)₃ |
| Et | U | Me | T | (CH₂)₃ |
| Et | U | CF₃ | T | (CH₂)₃ |
| Et | U | Et | T | (CH₂)₃ |
| Et | U | n-Pr | T | (CH₂)₃ |
| Et | U | NO₂ | T | (CH₂)₃ |
| Et | U | NH₂ | T | (CH₂)₃ |
| Et | U | NHCOPh | T | (CH₂)₃ |
| Et | U | CHO | T | (CH₂)₃ |
| Et | U | CN | T | (CH₂)₃ |
| Et | U | Ph | T | (CH₂)₃ |
| n-Bu | U | F | T | (CH₂)₃ |
| n-Bu | U | Cl | T | (CH₂)₃ |
| n-Bu | U | Br | T | (CH₂)₃ |
| n-Bu | U | I | T | (CH₂)₃ |
| n-Bu | U | Me | T | (CH₂)₃ |
| n-Bu | U | CF₃ | T | (CH₂)₃ |
| n-Bu | U | Et | T | (CH₂)₃ |
| n-Bu | U | n-Pr | T | (CH₂)₃ |
| n-Bu | U | NO₂ | T | (CH₂)₃ |
| n-Bu | U | NH₂ | T | (CH₂)₃ |
| n-Bu | U | NHCOPh | T | (CH₂)₃ |
| n-Bu | U | CHO | T | (CH₂)₃ |
| n-Bu | U | CN | T | (CH₂)₃ |
| n-Bu | U | Ph | T | (CH₂)₃ |
| c-Pr | U | F | T | (CH₂)₃ |
| c-Pr | U | Cl | T | (CH₂)₃ |
| c-Pr | U | Br | T | (CH₂)₃ |
| c-Pr | U | I | T | (CH₂)₃ |

TABLE 1-continued

T = structure (tetrazole)

Structure with R⁷-substituted biphenyl, N-R¹, pyrazole ring with R², R³, and N-A-phenyl

| R¹ | R² | R³ | R⁷ | A |
|---|---|---|---|---|
| c-Pr | U | Me | T | (CH₂)₃ |
| c-Pr | U | CF₃ | T | (CH₂)₃ |
| c-Pr | U | Et | T | (CH₂)₃ |
| c-Pr | U | n-Pr | T | (CH₂)₃ |
| c-Pr | U | NO₂ | T | (CH₂)₃ |
| c-Pr | U | NH₂ | T | (CH₂)₃ |
| c-Pr | U | NHCOPh | T | (CH₂)₃ |
| c-Pr | U | CHO | T | (CH₂)₃ |
| c-Pr | U | CN | T | (CH₂)₃ |
| c-Pr | U | Ph | T | (CH₂)₃ |
| n-Pr | U | F | T | (CH₂)₄ |
| n-Pr | U | Cl | T | (CH₂)₄ |
| n-Pr | U | Br | T | (CH₂)₄ |
| n-Pr | U | I | T | (CH₂)₄ |
| n-Pr | U | Me | T | (CH₂)₄ |
| n-Pr | U | CF₃ | T | (CH₂)₄ |
| n-Pr | U | Et | T | (CH₂)₄ |
| n-Pr | U | n-Pr | T | (CH₂)₄ |
| n-Pr | U | NO₂ | T | (CH₂)₄ |
| n-Pr | U | NH₂ | T | (CH₂)₄ |
| n-Pr | U | NHCOPh | T | (CH₂)₄ |
| n-Pr | U | CHO | T | (CH₂)₄ |
| n-Pr | U | CN | T | (CH₂)₄ |
| n-Pr | U | Ph | T | (CH₂)₄ |
| Et | U | F | T | (CH₂)₄ |
| Et | U | Cl | T | (CH₂)₄ |
| Et | U | Br | T | (CH₂)₄ |
| Et | U | I | T | (CH₂)₄ |
| Et | U | Me | T | (CH₂)₄ |
| Et | U | CF₃ | T | (CH₂)₄ |
| Et | U | Et | T | (CH₂)₄ |
| Et | U | n-Pr | T | (CH₂)₄ |
| Et | U | NO₂ | T | (CH₂)₄ |
| Et | U | NH₂ | T | (CH₂)₄ |
| Et | U | NHCOPh | T | (CH₂)₄ |
| Et | U | CHO | T | (CH₂)₄ |
| Et | U | CN | T | (CH₂)₄ |
| Et | U | Ph | T | (CH₂)₄ |
| n-Bu | U | F | T | (CH₂)₄ |
| n-Bu | U | Cl | T | (CH₂)₄ |
| n-Bu | U | Br | T | (CH₂)₄ |
| n-Bu | U | I | T | (CH₂)₄ |
| n-Bu | U | Me | T | (CH₂)₄ |
| n-Bu | U | CF₃ | T | (CH₂)₄ |
| n-Bu | U | Et | T | (CH₂)₄ |
| n-Bu | U | n-Pr | T | (CH₂)₄ |
| n-Bu | U | NO₂ | T | (CH₂)₄ |
| n-Bu | U | NH₂ | T | (CH₂)₄ |
| n-Bu | U | NHCOPh | T | (CH₂)₄ |
| n-Bu | U | CHO | T | (CH₂)₄ |
| n-Bu | U | CN | T | (CH₂)₄ |
| n-Bu | U | Ph | T | (CH₂)₄ |
| c-Pr | U | F | T | (CH₂)₄ |
| c-Pr | U | Cl | T | (CH₂)₄ |
| c-Pr | U | Br | T | (CH₂)₄ |
| c-Pr | U | I | T | (CH₂)₄ |
| c-Pr | U | Me | T | (CH₂)₄ |
| c-Pr | U | CF₃ | T | (CH₂)₄ |
| c-Pr | U | Et | T | (CH₂)₄ |
| c-Pr | U | n-Pr | T | (CH₂)₄ |
| c-Pr | U | NO₂ | T | (CH₂)₄ |
| c-Pr | U | NH₂ | T | (CH₂)₄ |
| c-Pr | U | NHCOPh | T | (CH₂)₄ |
| c-Pr | U | CHO | T | (CH₂)₄ |
| c-Pr | U | CN | T | (CH₂)₄ |
| c-Pr | U | Ph | T | (CH₂)₄ |
| n-Pr | U | F | T | C(=O) |
| n-Pr | U | Cl | T | C(=O) |
| n-Pr | U | Br | T | C(=a) |
| n-Pr | U | I | T | C(=O) |
| n-Pr | U | Me | T | C(=O) |
| n-Pr | U | CF₃ | T | C(=O) |
| n-Pr | U | Et | T | C(=O) |
| n-Pr | U | n-Pr | T | C(=O) |
| n-Pr | U | NO₂ | T | C(=O) |
| n-Pr | U | NH₂ | T | C(=O) |
| n-Pr | U | NHCOPh | T | C(=O) |
| n-Pr | U | CHO | T | C(=O) |
| n-Pr | U | CN | T | C(=O) |
| n-Pr | U | Ph | T | C(=O) |
| n-Pr | U | F | T | (CH₂)₂CO |
| n-Pr | U | Cl | T | (CH₂)₂CO |
| n-Pr | U | Br | T | (CH₂)₂CO |
| n-Pr | U | I | T | (CH₂)₂CO |
| n-Pr | U | Me | T | (CH₂)₂CO |
| n-Pr | U | CF₃ | T | (CH₂)₂CO |
| n-Pr | U | Et | T | (CH₂)₂CO |
| n-Pr | U | n-Pr | T | (CH₂)₂CO |
| n-Pr | U | NO₂ | T | (CH₂)₂CO |
| n-Pr | U | NH₂ | T | (CH₂)₂CO |
| n-Pr | U | NHCOPh | T | (CH₂)₂CO |
| n-Pr | U | CHO | T | (CH₂)₂CO |
| n-Pr | U | CN | T | (CH₂)₂CO |
| n-Pr | U | Ph | T | (CH₂)₂CO |
| Et | U | F | T | (CH₂)₂CO |
| Et | U | Cl | T | (CH₂)₂CO |
| Et | U | Br | T | (CH₂)₂CO |
| Et | U | I | T | (CH₂)₂CO |
| Et | U | Me | T | (CH₂)₂CO |
| Et | U | CF₃ | T | (CH₂)₂CO |
| Et | U | Et | T | (CH₂)₂CO |
| Et | U | n-Pr | T | (CH₂)₂CO |
| Et | U | NO₂ | T | (CH₂)₂CO |
| Et | U | NH₂ | T | (CH₂)₂CO |
| Et | U | NHCOPh | T | (CH₂)₂CO |
| Et | U | CHO | T | (CH₂)₂CO |
| Et | U | CN | T | (CH₂)₂CO |
| Et | U | Ph | T | (CH₂)₂CO |
| n-Bu | U | F | T | (CH₂)₂CO |
| n-Bu | U | Cl | T | (CH₂)₂CO |
| n-Bu | U | Br | T | (CH₂)₂CO |
| n-Bu | U | I | T | (CH₂)₂CO |
| n-Bu | U | Me | T | (CH₂)₂CO |
| n-Bu | U | CF₃ | T | (CH₂)₂CO |
| n-Bu | U | Et | T | (CH₂)₂CO |
| n-Bu | U | n-Pr | T | (CH₂)₂CO |

TABLE 1-continued

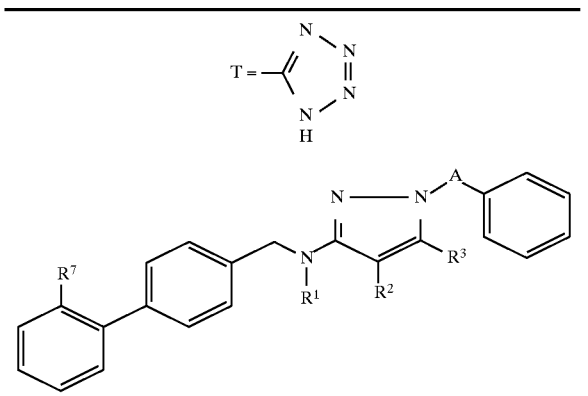

| R¹ | R² | R³ | R⁷ | A |
|---|---|---|---|---|
| n-Bu | U | NO₂ | T | (CH₂)₂CO |
| n-Bu | U | NH₂ | T | (CH₂)₂CO |
| n-Bu | U | NHCOPh | T | (CH₂)₂CO |
| n-Bu | U | CHO | T | (CH₂)₂CO |
| n-Bu | U | CN | T | (CH₂)₂CO |
| n-Bu | U | Ph | T | (CH₂)₂CO |
| c-Pr | U | F | T | (CH₂)₂CO |
| c-Pr | U | Cl | T | (CH₂)₂CO |
| c-Pr | U | Br | T | (CH₂)₂CO |
| c-Pr | U | I | T | (CH₂)₂CO |
| c-Pr | U | Me | T | (CH₂)₂CO |
| c-Pr | U | CF₃ | T | (CH₂)₂CO |
| c-Pr | U | Et | T | (CH₂)₂CO |
| c-Pr | U | n-Pr | T | (CH₂)₂CO |
| c-Pr | U | NO₂ | T | (CH₂)₂CO |
| c-Pr | U | NH₂ | T | (CH₂)₂CO |
| c-Pr | U | NHCOPh | T | (CH₂)₂CO |
| c-Pr | U | CHO | T | (CH₂)₂CO |
| c-Pr | U | CN | T | (CH₂)₂CO |
| c-Pr | U | Ph | T | (CH₂)₂CO |
| n-Pr | U | F | T | CH₂COCH₂ |
| n-Pr | U | Cl | T | CH₂COCH₂ |
| n-Pr | U | Br | T | CH₂COCH₂ |
| n-Pr | U | I | T | CH₂COCH₂ |
| n-Pr | U | Me | T | CH₂COCH₂ |
| n-Pr | U | CF₃ | T | CH₂COCH₂ |
| n-Pr | U | Et | T | CH₂COCH₂ |
| n-Pr | U | n-Pr | T | CH₂COCH₂ |
| n-Pr | U | NO₂ | T | CH₂COCH₂ |
| n-Pr | U | NH₂ | T | CH₂COCH₂ |
| n-Pr | U | NHCOPh | T | CH₂COCH₂ |
| n-Pr | U | CHO | T | CH₂COCH₂ |
| n-Pr | U | CN | T | CH₂COCH₂ |
| n-Pr | U | Ph | T | CH₂COCH₂ |
| Et | U | F | T | CH₂COCH₂ |
| Et | U | Cl | T | CH₂COCH₂ |
| Et | U | Br | T | CH₂COCH₂ |
| Et | U | I | T | CH₂COCH₂ |
| Et | U | Me | T | CH₂COCH₂ |
| Et | U | CF₃ | T | CH₂COCH₂ |
| Et | U | Et | T | CH₂COCH₂ |
| Et | U | n-Pr | T | CH₂COCH₂ |
| Et | U | NO₂ | T | CH₂COCH₂ |
| Et | U | NH₂ | T | CH₂COCH₂ |
| Et | U | NHCOPh | T | CH₂COCH₂ |
| Et | U | CHO | T | CH₂COCH₂ |
| Et | U | CN | T | CH₂COCH₂ |
| Et | U | Ph | T | CH₂COCH₂ |
| n-Bu | U | F | T | CH₂COCH₂ |
| n-Bu | U | Cl | T | CH₂COCH₂ |
| n-Bu | U | Br | T | CH₂COCH₂ |
| n-Bu | U | I | T | CH₂COCH₂ |
| n-Bu | U | Me | T | CH₂COCH₂ |
| n-Bu | U | CF₃ | T | CH₂COCH₂ |
| n-Bu | U | Et | T | CH₂COCH₂ |
| n-Bu | U | n-Pr | T | CH₂COCH₂ |
| n-Bu | U | NO₂ | T | CH₂COCH₂ |
| n-Bu | U | NH₂ | T | CH₂COCH₂ |

TABLE 1-continued

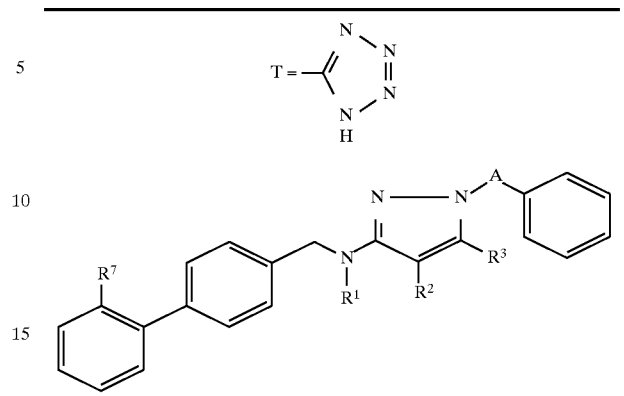

| R¹ | R² | R³ | R⁷ | A |
|---|---|---|---|---|
| n-Bu | U | NHCOPh | T | CH₂COCH₂ |
| n-Bu | U | CHO | T | CH₂COCH₂ |
| n-Bu | U | CN | T | CH₂COCH₂ |
| n-Bu | U | Ph | T | CH₂COCH₂ |
| c-Pr | U | F | T | CH₂COCH₂ |
| c-Pr | U | Cl | T | CH₂COCH₂ |
| c-Pr | U | Br | T | CH₂COCH₂ |
| c-Pr | U | I | T | CH₂COCH₂ |
| c-Pr | U | Me | T | CH₂COCH₂ |
| c-Pr | U | CF₃ | T | CH₂COCH₂ |
| c-Pr | U | Et | T | CH₂COCH₂ |
| c-Pr | U | n-Pr | T | CH₂COCH₂ |
| c-Pr | U | NO₂ | T | CH₂COCH₂ |
| c-Pr | U | NH₂ | T | CH₂COCH₂ |
| c-Pr | U | NHCOPh | T | CH₂COCH₂ |
| c-Pr | U | CHO | T | CH₂COCH₂ |
| c-Pr | U | CN | T | CH₂COCH₂ |
| c-Pr | U | Ph | T | CH₂COCH₂ |
| n-Pr | U | F | T | CH₂CH(Ph) |
| n-Pr | U | Cl | T | CH₂CH(Ph) |
| n-Pr | U | Br | T | CH₂CH(Ph) |
| n-Pr | U | I | T | CH₂CH(Ph) |
| n-Pr | U | Me | T | CH₂CH(Ph) |
| n-Pr | U | CF₃ | T | CH₂CH(Ph) |
| n-Pr | U | Et | T | CH₂CH(Ph) |
| n-Pr | U | n-Pr | T | CH₂CH(Ph) |
| n-Pr | U | c-Pr | T | CH₂CH(Ph) |
| n-Pr | U | NO₂ | T | CH₂CH(Ph) |
| n-Pr | U | NH₂ | T | CH₂CH(Ph) |
| n-Pr | U | N(Me)H | T | CH₂CH(Ph) |
| n-Pr | U | N(Me)₂ | T | CH₂CH(Ph) |
| n-Pr | U | N(Me)n-Bu | T | CH₂CH(Ph) |
| n-Pr | U | N(nPen)H | T | CH₂CH(Ph) |
| n-Pr | U | NHCOPh | T | CH₂CH(Ph) |
| n-Pr | U | N(Me)CO-c-Hex | T | CH₂CH(Ph) |
| n-Pr | U | NHCONHMe | T | CH₂CH(Ph) |
| n-Pr | U | N(Me)CONHPh | T | CH₂CH(Ph) |
| n-Pr | U | NHCONH-c-Hex | T | CH₂CH(Ph) |
| n-Pr | U | NHCOBz | T | CH₂CH(Ph) |
| n-Pr | U | J₁ | T | CH₂CH(Ph) |
| n-Pr | U | NBzCOO-n-Bu | T | CH₂CH(Ph) |
| n-Pr | U | NBzCOO-i-Bu | T | CH₂CH(Ph) |
| n-Pr | U | NHCO-n-Bu | T | CH₂CH(Ph) |
| n-Pr | U | NHCOO-i-Bu | T | CH₂CH(Ph) |
| n-Pr | U | NHCOCF₃ | T | CH₂CH(Ph) |
| n-Pr | U | NHSO₂CF₃ | T | CH₂CH(Ph) |
| n-Pr | U | N(Me)Ph | T | CH₂CH(Ph) |
| n-Pr | U | NHC(=NH)NH₂ | T | CH₂CH(Ph) |
| n-Pr | U | C(=NH)NH₂ | T | CH₂CH(Ph) |
| n-Pr | U | CHO | T | CH₂CH(Ph) |
| n-Pr | U | CN | T | CH₂CH(Ph) |
| n-Pr | U | U | T | CH₂CH(Ph) |
| n-Pr | U | COOMe | T | CH₂CH(Ph) |
| n-Pr | U | CONH₂ | T | CH₂CH(Ph) |
| n-Pr | U | CONHCOMe | T | CH₂CH(Ph) |
| n-Pr | U | CH₂NH₂ | T | CH₂CH(Ph) |
| n-Pr | U | CH₂OH | T | CH₂CH(Ph) |
| n-Pr | U | CH₂NHCOPh | T | CH₂CH(Ph) |

TABLE 1-continued

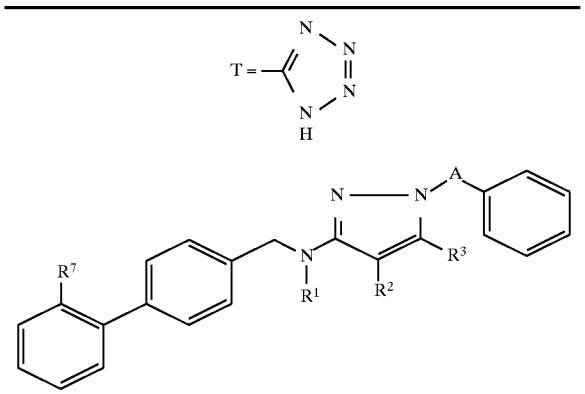
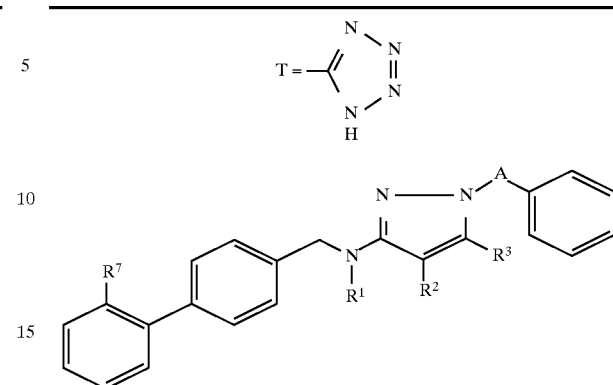

| R¹ | R² | R³ | R⁷ | A |
|---|---|---|---|---|
| n-Pr | U | CH₂N(nPen)COPh | T | CH₂CH(Ph) |
| n-Pr | U | CH₂NHCONHMe | T | CH₂CH(Ph) |
| n-Pr | U | CH₂CONHPh | T | CH₂CH(Ph) |
| n-Pr | U | CH₂COOH | T | CH₂CH(Ph) |
| n-Pr | U | Ph | T | CH₂CH(Ph) |
| n-Pr | U | Bz | T | CH₂CH(Ph) |
| n-Pr | U | CH₂CH₂Ph | T | CH₂CH(Ph) |
| n-Pr | U | 2-thienyl | T | CH₂CH(Ph) |
| n-Pr | U | 3-furyl | T | CH₂CH(Ph) |
| n-Pr | U | 1-pyrrolyl | T | CH₂CH(Ph) |
| n-Pr | U | 1-imidazolyl | T | CH₂CH(Ph) |
| n-Pr | U | 1-pyrazolyl | T | CH₂CH(Ph) |
| n-Pr | U | 2-pyridyl | T | CH₂CH(Ph) |
| n-Pr | U | 1-pyrrolidinyl | T | CH₂CH(Ph) |
| n-Pr | U | 1-piperidyl | T | CH₂CH(Ph) |
| n-Pr | U | 1-piperazinyl | T | CH₂CH(Ph) |
| n-Pr | U | 4-morpholinyl | T | CH₂CH(Ph) |
| n-Pr | U | Ph(2-Cl) | T | CH₂CH(Ph) |
| n-Pr | U | Ph(3-Me) | T | CH₂CH(Ph) |
| n-Pr | U | Ph(4-OMe) | T | CH₂CH(Ph) |
| n-Pr | U | Ph(2-NO₂) | T | CH₂CH(Ph) |
| n-Pr | U | Ph(3-NH₂) | T | CH₂CH(Ph) |
| n-Pr | U | Ph(4-NMe₂) | T | CH₂CH(Ph) |
| n-Pr | U | Ph(4-J²⁾) | T | CH₂CH(Ph) |
| n-Pr | U | Ph(2-Cl, 3-J¹) | T | CH₂CH(Ph) |
| n-Pr | U | Ph(2-Cl, 4-J¹) | T | CH₂CH(Ph) |
| n-Pr | U | Ph(2-Cl, 5-J¹) | T | CH₂CH(Ph) |
| n-Pr | U | Ph(2-Cl, 6-J¹) | T | CH₂CH(Ph) |
| n-Pr | U | CH₂CH₂Ph(2-Cl, 5-J¹) | T | CH₂CH(Ph) |
| n-Pr | U | T | T | CH₂CH(Ph) |
| Et | U | F | T | CH₂CH(Ph) |
| Et | U | Cl | T | CH₂CH(Ph) |
| Et | U | Br | T | CH₂CH(Ph) |
| Et | U | I | T | CH₂CH(Ph) |
| Et | U | Me | T | CH₂CH(Ph) |
| Et | U | CF₃ | T | CH₂CH(Ph) |
| Et | U | Et | T | CH₂CH(Ph) |
| Et | U | n-Pr | T | CH₂CH(Ph) |
| Et | U | c-Pr | T | CH₂CH(Ph) |
| Et | U | NO₂ | T | CH₂CH(Ph) |
| Et | U | NH₂ | T | CH₂CH(Rh) |
| Et | U | N(Me)H | T | CH₂CH(Ph) |
| Et | U | N(Me)₂ | T | CH₂CH(Ph) |
| Et | U | N(Me)n-Bu | T | CH₂CH(Ph) |
| Et | U | N(nPen)H | T | CH₂CH(Ph) |
| Et | U | NHCOPh | T | CH₂CH(Ph) |
| Et | U | NHC(=NH)NH₂ | T | CH₂CH(Ph) |
| Et | U | C(=NH)NH₂ | T | CH₂CH(Ph) |
| Et | U | CHO | T | CH₂CH(Ph) |
| Et | U | CN | T | CH₂CH(Ph) |
| Et | U | U | T | CH₂CH(Ph) |
| Et | U | COOMe | T | CH₂CH(Ph) |
| Et | U | CONH₂ | T | CH₂CH(Ph) |
| Et | U | CONHCOMe | T | CH₂CH(Ph) |
| n-Bu | U | F | T | CH₂CH(Ph) |
| n-Bu | U | Cl | T | CH₂CH(Ph) |
| n-Bu | U | Br | T | CH₂CH(Ph) |
| n-Bu | U | I | T | CH₂CH(Ph) |
| n-Bu | U | Me | T | CH₂CH(Ph) |
| n-Bu | U | CF₃ | T | CH₂CH(Ph) |
| n-Bu | U | Et | T | CH₂CH(Ph) |
| n-Bu | U | n-Pr | T | CH₂CH(Ph) |
| n-Bu | U | c-Pr | T | CH₂CH(Ph) |
| n-Bu | U | NO₂ | T | CH₂CH(Ph) |
| n-Bu | U | NH₂ | T | CH₂CH(Ph) |
| n-Bu | U | N(Me)H | T | CH₂CH(Ph) |
| n-Bu | U | N(Me)₂ | T | CH₂CH(Ph) |
| n-Bu | U | N(Me)n-Bu | T | CH₂CH(Ph) |
| n-Bu | U | N(nPen)H | T | CH₂CH(Ph) |
| n-Bu | U | NHCOPh | T | CH₂CH(Ph) |
| n-Bu | U | NHC(=NH)NH₂ | T | CH₂CH(Ph) |
| n-Bu | U | C(=NH)NH₂ | T | CH₂CH(Ph) |
| n-Bu | U | CHO | T | CH₂CH(Ph) |
| n-Bu | U | CN | T | CH₂CH(Ph) |
| n-Bu | U | U | T | CH₂CH(Ph) |
| n-Bu | U | COOMe | T | CH₂CH(Ph) |
| n-Bu | U | CONH₂ | T | CH₂CH(Ph) |
| n-Bu | U | CONHCOMe | T | CH₂CH(Ph) |
| c-Pr | U | F | T | CH₂CH(Ph) |
| c-Pr | U | Cl | T | CH₂CH(Ph) |
| c-Pr | U | Br | T | CH₂CH(Ph) |
| c-Pr | U | I | T | CH₂CH(Ph) |
| c-Pr | U | Me | T | CH₂CH(Ph) |
| c-Pr | U | CF₃ | T | CH₂CH(Ph) |
| c-Pr | U | Et | T | CH₂CH(Ph) |
| c-Pr | U | n-Pr | T | CH₂CH(Ph) |
| c-Pr | U | c-Pr | T | CH₂CH(Ph) |
| c-Pr | U | NO₂ | T | CH₂CH(Ph) |
| c-Pr | U | NH₂ | T | CH₂CH(Ph) |
| c-Pr | U | N(Me)H | T | CH₂CH(Ph) |
| c-Pr | U | N(Me)₂ | T | CH₂CH(Ph) |
| c-Pr | U | N(Me)n-Bu | T | CH₂CH(Ph) |
| c-Pr | U | N(nPen)H | T | CH₂CH(Ph) |
| c-Pr | U | NHCOPh | T | CH₂CH(Ph) |
| c-Pr | U | NHC(=NH)NH₂ | T | CH₂CH(Ph) |
| c-Pr | U | C(=NH)NH₂ | T | CH₂CH(Ph) |
| c-Pr | U | CHO | T | CH₃CH(Ph) |
| c-Pr | U | CN | T | CH₂CH(Ph) |
| c-Pr | U | U | T | CH₂CH(Ph) |
| c-Pr | U | COOMe | T | CH₂CH(Ph) |
| c-Pr | U | CONH₂ | T | CH₂CH(Ph) |
| c-Pr | U | CONHCOMe | T | CH₂CH(Ph) |
| n-Pr | U | F | U | CH₂CH(Ph) |
| n-Pr | U | Cl | U | CH₂CH(Ph) |
| n-Pr | U | Br | U | CH₂CH(Ph) |
| n-Pr | U | I | U | CH₂CH(Ph) |
| n-Pr | U | Me | U | CH₂CH(Ph) |
| n-Pr | U | CF₃ | U | CH₂CH(Ph) |
| n-Pr | U | Et | U | CH₂CH(Ph) |
| n-Pr | U | n-Pr | U | CH₂CH(Ph) |
| n-Pr | U | c-Pr | U | CH₂CH(Ph) |
| n-Pr | U | NO₂ | U | CH₂CH(Ph) |
| n-Pr | U | NH₂ | U | CH₂CH(Ph) |
| n-Pr | U | N(Me)H | U | CH₂CH(Ph) |
| n-Pr | U | N(Me)₂ | U | CH₂CH(Ph) |
| n-Pr | U | N(Me)n-Bu | U | CH₂CH (Ph) |

TABLE 1-continued

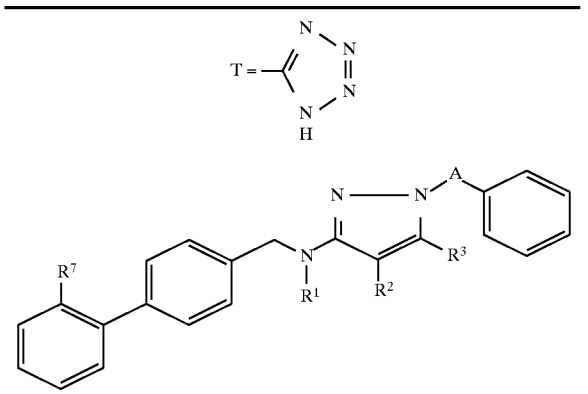

| R¹ | R² | R³ | R⁷ | A |
|---|---|---|---|---|
| n-Pr | U | N(nPen)H | U | CH₂CH(Ph) |
| n-Pr | U | NHCOPh | U | CH₂CH(Ph) |
| n-Pr | U | NHC(=NH)NH₂ | U | CH₂CH(Ph) |
| n-Pr | U | C(=NH)NH₂ | U | CH₂CH(Ph) |
| n-Pr | U | CHO | U | CH₂CH(Ph) |
| n-Pr | U | CN | U | CH₂CH(Ph) |
| n-Pr | U | U | U | CH₂CH(Ph) |
| n-Pr | U | COOMe | U | CH₂CH(Ph) |
| n-Pr | U | CONH₂ | U | CH₂CH(Ph) |
| n-Pr | U | CONHCOMe | U | CH₂CH(Ph) |
| n-Pr | U | F | T | CH₂C(=O) |
| n-Pr | U | Cl | T | CH₂C(=O) |
| n-Pr | U | Br | T | CH₂C(=O) |
| n-Pr | U | I | T | CH₂C(=O) |
| n-Pr | U | Me | T | CH₂C(=O) |
| n-Pr | U | CF₃ | T | CH₂C(=O) |
| n-Pr | U | Et | T | CH₂C(=O) |
| n-Pr | U | n-Pr | T | CH₂C(=O) |
| n-Pr | U | c-Pr | T | CH₂C(=O) |
| n-Pr | U | NO₂ | T | CH₂C(=O) |
| n-Pr | U | NH₂ | T | CH₂C(=O) |
| n-Pr | U | N(Me)H | T | CH₂C(=O) |
| n-Pr | U | N(Me)₂ | T | CH₂C(=O) |
| n-Pr | U | N(Me)n-Bu | T | CH₂C(=O) |
| n-Pr | U | N(nPen)H | T | CH₂C(=O) |
| n-Pr | U | NHCOPh | T | CH₂C(=O) |
| n-Pr | U | N(Me)CO-c-Hex | T | CH₂C(=O) |
| n-Pr | U | NHCONHMe | T | CH₂C(=O) |
| n-Pr | U | N(Me)CONHPh | T | CH₂C(=O) |
| n-Pr | U | NHCONH-c-Hex | T | CH₂C(=O) |
| n-Pr | U | NHCOBz | T | CH₂C(=O) |
| n-Pr | U | J¹ | T | CH₂C(=O) |
| n-Pr | U | NBzCO-n-Bu | T | CH₂C(=O) |
| n-Pr | U | NBzCOO-i-Bu | T | CH₂C(=O) |
| n-Pr | U | NHCO-n-Bu | T | CH₂C(=O) |
| n-Pr | U | NHCOO-i-Bu | T | CH₂C(=O) |
| n-Pr | U | NHCOCF₃ | T | CH₂C(=O) |
| n-Pr | U | NHSO₂CF₃ | T | CH₂C(=O) |
| n-Pr | U | N(Me)Ph | T | CH₂C(=O) |
| n-Pr | U | NHC(=NH)NH₂ | T | CH₂C(=O) |
| n-Pr | U | C(=NH)NH₂ | T | CH₂C(=O) |
| n-Pr | U | CHO | T | CH₂C(=O) |
| n-Pr | U | CN | T | CH₂C(=O) |
| n-Pr | U | U | T | CH₂C(=O) |
| n-Pr | U | COOMe | T | CH₂C(=O) |
| n-Pr | U | CONH₂ | T | CH₂C(=O) |
| n-Pr | U | CONHCOMe | T | CH₂C(=O) |
| n-Pr | U | CH₂NH₂ | T | CH₂C(=O) |
| n-Pr | U | CH₂OH | T | CH₂C(=O) |
| n-Pr | U | CH₂NHCOPh | T | CH₂C(=O) |
| n-Pr | U | CH₂N(nPen)COPh | T | CH₂C(=O) |
| n-Pr | U | CH₂NHCONHMe | T | CH₂C(=O) |
| n-Pr | U | CH₂CONHPh | T | CH₂C(=O) |
| n-Pr | U | CH₂COOH | T | CH₂C(=O) |
| n-Pr | U | Ph | T | CH₂C(=O) |
| n-Pr | U | Bz | T | CH₂C(=O) |
| n-Pr | U | CH₂CH₂Ph | T | CH₂C(=O) |
| n-Pr | U | 2-thienyl | T | CH₂C(=O) |

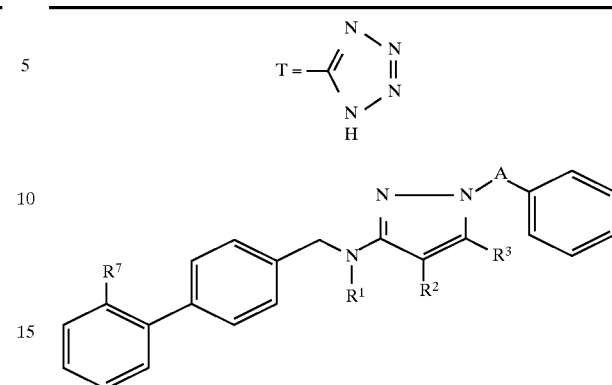

| R¹ | R² | R³ | R⁷ | A |
|---|---|---|---|---|
| n-Pr | U | 3-furyl | T | CH₂C(=O) |
| n-Pr | U | 1-pyrrolyl | T | CH₂C(=O) |
| n-Pr | U | 1-imidazolyl | T | CH₂C(=O) |
| n-Pr | U | 1-pyrazolyl | T | CH₂C(=O) |
| n-Pr | U | 2-pyridyl | T | CH₂C(=O) |
| n-Pr | U | 1-pyrrolidinyl | T | CH₂C(=O) |
| n-Pr | U | 1-piperidyl | T | CH₂C(=O) |
| n-Pr | U | 1-piperazinyl | T | CH₂C(=O) |
| n-Pr | U | 4-morpholinyl | T | CH₂C(=O) |
| n-Pr | U | Ph(2-Cl) | T | CH₂C(=O) |
| n-Pr | U | Ph(3-Me) | T | CH₂C(=O) |
| n-Pr | U | Ph(4-OMe) | T | CH₂C(=O) |
| n-Pr | U | Ph(2-NO₂) | T | CH₂C(=O) |
| n-Pr | U | Ph(3-NH₂) | T | CH₂C(=O) |
| n-Pr | U | Ph(4-NMe₂) | T | CH₂C(=O) |
| n-Pr | U | Ph(4-J²) | T | CH₂C(=O) |
| n-Pr | U | Ph(2-Cl, 3-J¹) | T | CH₂C(=O) |
| n-Pr | U | Ph(2-Cl, 4-J¹) | T | CH₂C(=O) |
| n-Pr | U | Ph(2-Cl, 5-J¹) | T | CH₂C(=O) |
| n-Pr | U | Ph(2-Cl, 6-J¹) | T | CH₂C(=O) |
| n-Pr | U | CH₂CH₂Ph(2-Cl,5-J¹) | T | CH₂C(=O) |
| n-Pr | U | T | T | CH₂C(=O) |
| Et | U | F | T | CH₂C(=O) |
| Et | U | Cl | T | CH₂C(=O) |
| Et | U | Br | T | CH₂C(=O) |
| Et | U | I | T | CH₂C(=O) |
| Et | U | Me | T | CH₂C(=O)) |
| Et | U | CF₃ | T | CH₂C(=O) |
| Et | U | Et | T | CH₂C(=O) |
| Et | U | n-Pr | T | CH₂C(=O) |
| Et | U | c-Pr | T | CH₂C(=O) |
| Et | U | NO₂ | T | CH₂C(=O) |
| Et | U | NH₂ | T | CH₂C(=O) |
| Et | U | N(Me)H | T | CH₂C(=O) |
| Et | U | N(Me)₂ | T | CH₂C(=O) |
| Et | U | N(Me)n-Bu | T | CH₂C(=O) |
| Et | U | N(nPen)H | T | CH₂C(=O) |
| Et | U | NHCOPh | T | CH₂C(=O) |
| Et | U | N(Me)CO-c-Hex | T | CH₂C(=O) |
| Et | U | NHCONHMe | T | CH₂C(=O) |
| Et | U | N(Me)CONHPh | T | CH₂C(=O) |
| Et | U | NHC(=NH)NH₂ | T | CH₂C(=O) |
| Et | U | C(=NH)NH₂ | T | CH₂C(=O) |
| Et | U | CHO | T | CH₂C(=O) |
| Et | U | CN | T | CH₂C(=O) |
| Et | U | U | T | CH₂C(=O) |
| Et | U | COOMe | T | CH₂C(=O) |
| Et | U | CONH₂ | T | CH₂C(=O) |
| Et | U | CONHCOMe | T | CH₂C(=O) |
| n-Bu | U | F | T | CH₂C(=O) |
| n-Bu | U | Cl | T | CH₂C(=O) |
| n-Bu | U | Br | T | CH₂C(=O) |
| n-Bu | U | I | T | CH₂C(=O) |
| n-Bu | U | Me | T | CH₂C(=O) |
| n-Bu | U | CF₃ | T | CH₂C(=O) |
| n-Bu | U | Et | T | CH₂C(=O) |
| n-Bu | U | n-Pr | T | CH₂C(=O) |
| n-Bu | U | c-Pr | T | CH₂C(=O) |

TABLE 1-continued

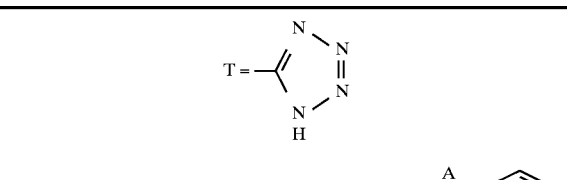

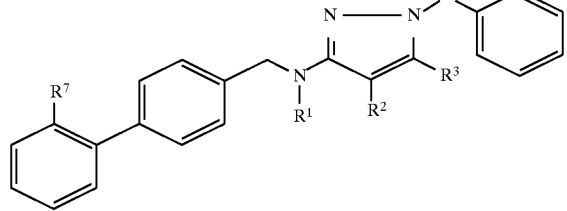

| R¹ | R² | R³ | R⁷ | A |
|---|---|---|---|---|
| n-Bu | U | NO₂ | T | CH₂C(=O) |
| n-Bu | U | NH₂ | T | CH₂C(=O) |
| n-Bu | U | N(Me)H | T | CH₂C(=O) |
| n-Bu | U | N(Me)₂ | T | CH₂C(=O) |
| n-Bu | U | N(Me)n-Bu | T | CH₂C(=O) |
| n-Bu | U | N(nPen)H | T | CH₂C(=O) |
| n-Bu | U | NHCOPh | T | CH₂C(=O) |
| n-Bu | U | NHC(=NH)NH₂ | T | CH₂C(=O) |
| n-Bu | U | C(=NH)NH₂ | T | CH₂C(=O) |
| n-Bu | U | CHO | T | CH₂C(=O) |
| n-Bu | U | CN | T | CH₂C(=O) |
| n-Bu | U | U | T | CH₂C(=O) |
| n-Bu | U | COOMe | T | CH₂C(=O) |
| n-Bu | U | CONH₂ | T | CH₂C(=O) |
| n-Bu | U | CONHCHOMe | T | CH₂C(=O) |
| c-Pr | U | F | T | CH₂C(=O) |
| c-Pr | U | Cl | T | CH₂C(=O) |
| c-Pr | U | Br | T | CH₂C(=O) |
| c-Pr | U | I | T | CH₂C(=O) |
| c-Pr | U | Me | T | CH₂C(=O) |
| c-Pr | U | CF₃ | T | CH₂C(=O) |
| c-Pr | U | Et | T | CH₂C(=O) |
| c-Pr | U | n-Pr | T | CH₂C(=O) |
| c-Pr | U | c-Pr | T | CH₂C(=O) |
| c-Pr | U | NO₂ | T | CH₂C(=O) |
| c-Pr | U | NH₂ | T | CH₂C(=O) |
| c-Pr | U | N(Me)H | T | CH₂C(=O) |
| c-Pr | U | N(Me)₂ | T | CH₂C(=O) |
| c-Pr | U | N(Me)n-Bu | T | CH₂C(=O) |
| c-Pr | U | N(nPen)H | T | CH₂C(=O) |
| c-Pr | U | NHCOPh | T | CH₂C(=O) |
| c-Pr | U | NHC(=NH)NH₂ | T | CH₂C(=O) |
| c-Pr | U | C(=NH)NH₂ | T | CH₂C(=O) |
| c-Pr | U | CHO | T | CH₂C(=O) |
| c-Pr | U | CN | T | CH₂C(=O) |
| c-Pr | U | U | T | CH₂C(=O) |
| c-Pr | U | COOMe | T | CH₂C(=O) |
| c-Pr | U | CONH₂ | T | CH₂C(=O) |
| c-Pr | U | CONHCOMe | T | CH₂C(=O) |
| n-Pr | U | F | T | (CH₂)₂ |
| n-Pr | U | Cl | T | (CH₂)₂ |
| n-Pr | U | Br | T | (CH₂)₂ |
| n-Pr | U | I | T | (CH₂)₂ |
| n-Pr | U | Me | T | (CH₂)₂ |
| n-Pr | U | CF₃ | T | (CH₂)₂ |
| n-Pr | U | Et | T | (CH₂)₂ |
| n-Pr | U | n-Pr | T | (CH₂)₂ |
| n-Pr | U | c-Pr | T | (CH₂)₂ |
| n-Pr | U | NO₂ | T | (CH₂)₂ |
| n-Pr | U | NH₂ | T | (CH₂)₂ |
| n-Pr | U | N(Me)H | T | (CH₂)₂ |
| n-Pr | U | N(Me)₂ | T | (CH₂)₂ |
| n-Pr | U | N(Me)n-Bu | T | (CH₂)₂ |
| n-Pr | U | N(nPen)H | T | (CH₂)₂ |
| n-Pr | U | NHCOPh | T | (CH₂)₂ |
| n-Pr | U | N(Me)CO-c-Hex | T | (CH₂)₂ |
| n-Pr | U | NHCONHMe | T | (CH₂)₂ |
| n-Pr | U | N(Me)CONHPh | T | (CH₂)₂ |
| n-Pr | U | NHCONH-c-Hex | T | (CH₂)₂ |
| n-Pr | U | NHCOBz | T | (CH₂)₂ |
| n-Pr | U | J¹ | T | (CH₂)₂ |
| n-Pr | U | NBzCO-n-Bu | T | (CH₂)₂ |
| n-Pr | U | NBzCOO-i-Bu | T | (CH₂)₂ |
| n-Pr | U | NHCO-n-Bu | T | (CH₂)₂ |
| n-Pr | U | NHCOO-i-Bu | T | (CH₂)₂ |
| n-Pr | U | NHCOCF₃ | T | (CH₂)₂ |
| n-Pr | U | NHSO₂CF₃ | T | (CH₂)₂ |
| n-Pr | U | N(Me)Ph | T | (CH₂)₂ |
| n-Pr | U | NHC(=NH)NH₂ | T | (CH₂)₂ |
| n-Pr | U | C(=NH)NH₂ | T | (CH₂)₂ |
| n-Pr | U | CHO | T | (CH₂)₂ |
| n-Pr | U | CN | T | (CH₂)₂ |
| n-Pr | U | U | T | (CH₂)₂ |
| n-Pr | U | COOMe | T | (CH₂)₂ |
| n-Pr | U | CONH₂ | T | (CH₂)₂ |
| n-Pr | U | CONHCOMe | T | (CH₂)₂ |
| n-Pr | U | CH₂NH₂ | T | (CH₂)₂ |
| n-Pr | U | CH₂OH | T | (CH₂)₂ |
| n-Pr | U | CH₂NHCOPh | T | (CH₂)₂ |
| n-Pr | U | CH₂N(nPen)COPh | T | (CH₂)₂ |
| n-Pr | U | CH₂NHCONHMe | T | (CH₂)₂ |
| n-Pr | U | CH₂CONHPh | T | (CH₂)₂ |
| n-Pr | U | CH₂COOH | T | (CH₂)₂ |
| n-Pr | U | Ph | T | (CH₂)₂ |
| n-Pr | U | Bz | T | (CH₂)₂ |
| n-Pr | U | CH₂CH₂Ph | T | (CH₂)₂ |
| n-Pr | U | 2-thienyl | T | (CH₂)₂ |
| n-Pr | U | 3-furyl | T | (CH₂)₂ |
| n-Pr | U | 1-pyrrolyl | T | (CH₂)₂ |
| n-Pr | U | 1-imidazolyl | T | (CH₂)₂ |
| n-Pr | U | 1-pyrazolyl | T | (CH₂)₂ |
| n-Pr | U | 2-pyridyl | T | (CH₂)₂ |
| n-Pr | U | 1-pyrrolidinyl | T | (CH₂)₂ |
| n-Pr | U | 1-piperidyl | T | (CH₂)₂ |
| n-Pr | U | 1-piperazinyl | T | (CH₂)₂ |
| n-Pr | U | 4-morpholinyl | T | (CH₂)₂ |
| n-Pr | U | Ph(2-Cl) | T | (CH₂)₂ |
| n-Pr | U | Ph(3-Me) | T | (CH₂)₂ |
| n-Pr | U | Ph(4-OMe) | T | (CH₂)₂ |
| n-Pr | U | Ph(2-NO₂) | T | (CH₂)₂ |
| n-Pr | U | Ph(3-NH₂) | T | (CH₂)₂ |
| n-Pr | U | Ph(4-NMe₂) | T | (CH₂)₂ |
| n-Pr | U | Ph(4-J²) | T | (CH₂)₂ |
| n-Pr | U | Ph(2-Cl,3-J¹) | T | (CH₂)₂ |
| n-Pr | U | Ph(2-Cl,4-J¹) | T | (CH₂)₂ |
| n-Pr | U | Ph(2-Cl,5-J¹) | T | (CH₂)₂ |
| n-Pr | U | Ph(2-Cl, 6-J¹) | T | (CH₂)₂ |
| n-Pr | U | Ph(3-NHCOPh) | T | (CH₂)₂ |
| n-Pr | U | Ph(4-NHCO-c-Hex) | T | (CH₂)₂ |
| n-Pr | U | Ph(3-NHCONHMe) | T | (CH₂)₂ |
| n-Pr | U | Ph(4-NMeCONHPh) | T | (CH₂)₂ |
| n-Pr | U | Ph(3-NHCONH-c-Hex) | T | (CH₂)₂ |
| n-Pr | U | Ph(4-NHCOBz) | T | (CH₂)₂ |
| n-Pr | U | Ph(4-N(nPen)COPh) | T | (CH₂)₂ |
| n-Pr | U | Ph(3-NHCOnBu) | T | (CH₂)₂ |

TABLE 1-continued

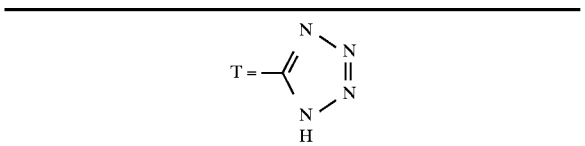

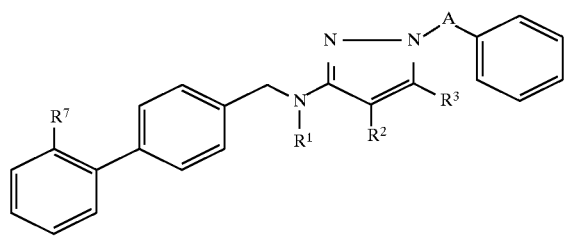

| R¹ | R² | R³ | R⁷ | A |
|---|---|---|---|---|
| n-Pr | U | Ph(4-NHCOCF₃) | T | (CH₂)₂ |
| n-Pr | U | Ph(3-NHSO₂CF₃) | T | (CH₂)₂ |
| n-Pr | U | Ph(4-NMePh) | T | (CH₂)₂ |
| n-Pr | U | Ph(3-NHC(=NH)NH₂) | T | (CH₂)₂ |
| n-Pr | U | Ph(4-C(=NH)NH₂) | T | (CH₂)₂ |
| n-Pr | U | Ph(3-COOH) | T | (CH₂)₂ |
| n-Pr | U | Ph(4-CONH₂) | T | (CH₂)₂ |
| n-Pr | U | Ph(3-CH₂NH₂) | T | (CH₂)₂ |
| n-Pr | U | Ph(4-CH₂OH) | T | (CH₂)₂ |
| n-Pr | U | Ph(4-CH₂²J²) | T | (CH₂)₂ |
| n-Pr | U | Ph(4-CH₂NHCONHMe) | T | (CH₂)₂ |
| n-Pr | U | Ph(4-CH₂CONHPh) | T | (CH₂)₂ |
| n-Pr | U | Ph(4-CH₂COOH) | T | (CH₂)₂ |
| n-Pr | U | Ph(4-Ph) | T | (CH₂)₂ |
| n-Pr | U | CH₂CH₂Ph(2-Cl,5-J¹) | T | (CH₂)₂ |
| n-Pr | U | OH | T | (CH₂)₂ |
| n-Pr | U | OMe | T | (CH₂)₂ |
| n-Pr | U | OPh | T | (CH₂)₂ |
| n-Pr | U | SH | T | (CH₃)₂ |
| n-Pr | U | SPh | T | (CH₂)₂ |
| n-Pr | U | SO₂Ph | T | (CH₂)₂ |
| n-Pr | U | S-n-Bu | T | (CH₂)₂ |
| n-Pr | U | 2-pyrazinyl | T | (CH₂)₂ |
| n-Pr | U | 2-pyrimidinyl | T | (CH₂)₂ |
| n-Pr | U | 3-pyridyl | T | (CH₂)₂ |
| n-Pr | U | 4-pyridyl | T | (CH₂)₂ |
| n-Pr | U | T | T | (CH₂)₂ |
| Me | U | F | T | (CH₂)₂ |
| Me | U | Cl | T | (CH₂)₂ |
| Me | U | Br | T | (CH₂)₂ |
| Me | U | I | T | (CH₂)₂ |
| Me | U | Me | T | (CH₂)₂ |
| Me | U | CF₃ | T | (CH₂)₂ |
| Me | U | Et | T | (CH₂)₂ |
| Me | U | n-Pr | T | (CH₂)₂ |
| Me | U | c-Pr | T | (CH₂)₂ |
| Me | U | NO₂ | T | (CH₂)₂ |
| Me | U | NH₂ | T | (CH₂)₂ |
| Me | U | N(Me)H | T | (CH₂)₂ |
| Me | U | N(Me)₂ | T | (CH₂)₂ |
| Me | U | N(Me)n-Bu | T | (CH₂)₂ |
| Me | U | N(nPen)H | T | (CH₂)₂ |
| Me | U | NHCOPh | T | (CH₂)₂ |
| Me | U | J¹ | T | (CH₂)₂ |
| Me | U | NHC(=NH)NH₂ | T | (CH₂)₂ |
| Me | U | C(=NH)NH₂ | T | (CH₂)₂ |
| Me | U | CHO | T | (CH₂)₂ |
| Me | U | CN | T | (CH₂)₂ |
| Me | U | U | T | (CH₂)₂ |
| Me | U | COOMe | T | (CH₃)₂ |
| Me | U | CONH₂ | T | (CH₂)₂ |
| Me | U | COHCOMe | T | (CH₂)₂ |
| Me | U | CH₂COOH | T | (CH₂)₂ |
| Me | U | Ph | T | (CH₂)₂ |
| Me | U | Bz | T | (CH₂)₂ |
| Me | U | CH₂CH₂Ph | T | (CH₂)₂ |

TABLE 1-continued

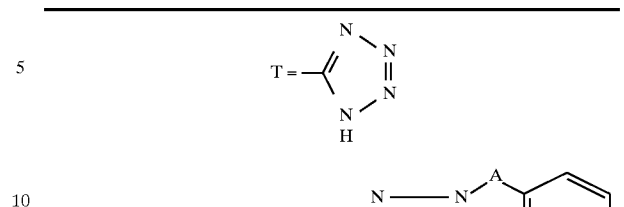

| R¹ | R² | R³ | R⁷ | A |
|---|---|---|---|---|
| Me | U | T | T | (CH₂)₂ |
| Et | U | F | T | (CH₂)₂ |
| Et | U | Cl | T | (CH₂)₂ |
| Et | U | Br | T | (CH₂)₂ |
| Et | U | I | T | (CH₂)₂ |
| Et | U | Me | T | (CH₂)₂ |
| Et | U | CF₃ | T | (CH₂)₂ |
| Et | U | Et | T | (CH₂)₂ |
| Et | U | n-Pr | T | (CH₂)₂ |
| Et | U | c-Pr | T | (CH₂)₂ |
| Et | U | NO₂ | T | (CH₂)₂ |
| Et | U | NH₂ | T | (CH₂)₂ |
| Et | U | N(Me)H | T | (CH₂)₂ |
| Et | U | N(Me)₂ | T | (CH₂)₂ |
| Et | U | N(Me)n-Bu | T | (CH₂)₂ |
| Et | U | N(nPen)H | T | (CH₂)₂ |
| Et | U | NHCOPh | T | (CH₂)₂ |
| Et | U | N(Me)CO-c-Hex | T | (CH₂)₂ |
| Et | U | NHCONHMe | T | (CH₂)₂ |
| Et | U | N(Me)CONHPh | T | (CH₂)₂ |
| Et | U | NHCONH-c-Hex | T | (CH₂)₂ |
| Et | U | NHCOBz | T | (CH₂)₂ |
| Et | U | J¹ | T | (CH₂)₂ |
| Et | U | NBzCO-n-Bu | T | (CH₂)₂ |
| Et | U | NBzCOO-i-Bu | T | (CH₂)₂ |
| Et | U | NHCO-n-Bu | T | (CH₂)₂ |
| Et | U | NHCOO-i-Bu | T | (CH₂)₂ |
| Et | U | NHCOCF₃ | T | (CH₂)₂ |
| Et | U | NHSO₂CF₃ | T | (CH₂)₂ |
| Et | U | N(Me)Ph | T | (CH₂)₂ |
| Et | U | NHC(=NH)NH₂ | T | (CH₂)₂ |
| Et | U | C(=NH)NH₂ | T | (CH₂)₂ |
| Et | U | CHO | T | (CH₂)₂ |
| Et | U | CN | T | (CH₂)₂ |
| Et | U | U | T | (CH₂)₂ |
| Et | U | COOMe | T | (CH₂)₂ |
| Et | U | CONH₂ | T | (CH₂)₂ |
| Et | U | CONHCOMe | T | (CH₂)₂ |
| Et | U | CH₂NH₂ | T | (CH₂)₂ |
| Et | U | CH₂OH | T | (CH₂)₂ |
| Et | U | CH₂NHCOPh | T | (CH₂)₂ |
| Et | U | CH₂N(nPen)COPh | T | (CH₂)₂ |
| Et | U | CH₂NHCONHMe | T | (CH₂)₂ |
| Et | U | CH₂CONHPh | T | (CH₂)₂ |
| Et | U | CH₂COOH | T | (CH₂)₂ |
| Et | U | Ph | T | (CH₂)₂ |
| Et | U | Bz | T | (CH₂)₂ |
| Et | U | CH₂CH₂Ph | T | (CH₂)₂ |
| Et | U | 2-thienyl | T | (CH₂)₂ |
| Et | U | 3-furyl | T | (CH₂)₂ |
| Et | U | 1-pyrrolyl | T | (CH₂)₂ |
| Et | U | 1-imidazolyl | T | (CH₂)₂ |
| Et | U | 1-pyrazolyl | T | (CH₂)₂ |
| Et | U | 2-pyridyl | T | (CH₂)₂ |
| Et | U | 1-pyrrolidinyl | T | (CH₂)₂ |
| Et | U | 1-piperidyl | T | (CH₂)₂ |
| Et | U | 1-piperazinyl | T | (CH₂)₂ |
| Et | U | 1-morpholinyl | T | (CH₂)₂ |

TABLE 1-continued

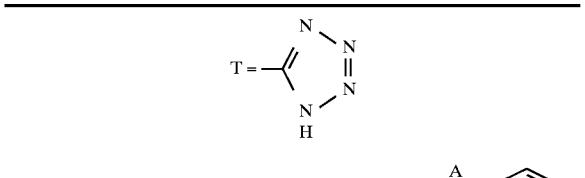

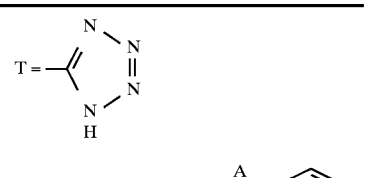

| R¹ | R² | R³ | R⁷ | A |
|---|---|---|---|---|
| Et | U | Ph(2-Cl) | T | (CH₂)₂ |
| Et | U | Ph(3-Me) | T | (CH₂) |
| Et | U | Ph(4-OMe) | T | (CH₂)₂ |
| Et | U | Ph(2-NO₂) | T | (CH₂)₂ |
| Et | U | Ph(3-NH₂) | T | (CH₂)₂ |
| Et | U | Ph(4-NMe₂) | T | (CH₂)₂ |
| Et | U | Ph(4-J²) | T | (CH₂)₂ |
| Et | U | Ph(2-Cl,3-J¹) | T | (CH₂)₂ |
| Et | U | Ph(2-Cl,4-J¹) | T | (CH₂)₂ |
| Et | U | Ph(2-Cl,5-J¹) | T | (CH₂)₂ |
| Et | U | Ph(2-Cl,6-J¹) | T | (CH₂)₂ |
| Et | U | Ph(3-NHCOPh) | T | (CH₂)₂ |
| Et | U | Ph(4-NHCO-c-Hex) | T | (CH₂)₂ |
| Et | U | Ph(3-NHCONHMe) | T | (CH₂)₂ |
| Et | U | Ph(4-NMeCONHPh) | T | (CH₂)₂ |
| Et | U | Ph(3-NHCONH-c-Hex) | T | (CH₂)₂ |
| Et | U | Ph(4-NHCOBz) | T | (CH₂)₂ |
| Et | U | Ph(4-N(nPen)COPh) | T | (CH₂)₂ |
| Et | U | Ph(3-NHCOnBu) | T | (CH₂)₂ |
| Et | U | Ph(4-NHCOCF³) | T | (CH₂)₂ |
| Et | U | Ph(3-NHSO₂CF₃) | T | (CH₂)₂ |
| Et | U | Ph(4-NMePh) | T | (CH₂)₂ |
| Et | U | Ph(3-NHC(=NH)NH₂) | T | (CH₂)₂ |
| Et | U | Ph(4-C(=NH)NH₂) | T | (CH₂)₂ |
| Et | U | Ph(3-COOH) | T | (CH₂) |
| Et | U | Ph(4-CONH₂) | T | (CH₂)₂ |
| Et | U | Ph(3-CH₂NH₂) | T | (CH₂)₂ |
| Et | U | Ph(4-CH₂OH) | T | (CH₂)₂ |
| Et | U | Ph(4-CH₂J²) | T | (CH₂)₂ |
| Et | U | Ph(4-CH₂NHCONHMe) | T | (CH₂)₂ |
| Et | U | Ph(4-CH₂CONHPh) | T | (CH₂)₂ |
| Et | U | Ph(4-CH₂COOH) | T | (CH₂)₂ |
| Et | U | Ph(4-Ph) | T | (CH₂)₂ |
| Et | U | CH₂CH₂Ph(2-Cl,5-J¹) | T | (CH₂)₂ |
| Et | U | OH | T | (CH₂)₂ |
| Et | U | OMe | T | (CH₂)₂ |
| Et | U | OPh | T | (CH₂)₂ |
| Et | U | SH | T | (CH₂)₂ |
| Et | U | SPh | T | (CH₂)₂ |
| Et | U | SO₂Ph | T | (CH₂)₂ |
| Et | U | S-n-Bu | T | (CH₂)₂ |
| Et | U | 2-pyrazinyl | T | (CH₂)₂ |
| Et | U | 2-pyrimidinyl | T | (CH₂)₂ |
| Et | U | 3-pyridyl | T | (CH₂)₂ |
| Et | U | 4-pyridyl | T | (CH₂)₂ |
| Et | U | T | T | (CH₂)₂ |
| n-Bu | U | F | T | (CH₂)₂ |
| n-Bu | U | Cl | T | (CH₂)₂ |
| n-Bu | U | Br | T | (CH₂)₂ |
| n-Bu | U | I | T | (CH₂)₂ |
| n-Bu | U | Me | T | (CH₂)₂ |
| n-Bu | U | CF₃ | T | (CH₂)₂ |
| n-Bu | U | Et | T | (CH₂)₂ |
| n-Bu | U | n-Pr | T | (CH₂)₂ |
| n-Bu | U | c-Pr | T | (CH₂)₂ |
| n-Bu | U | NO₂ | T | (CH₂)₂ |
| n-Bu | U | NH₂ | T | (CH₂)₂ |
| n-Bu | U | N(Me)H | T | (CH₂)₂ |
| n-Bu | U | N(Me)₂ | T | (CH₂)₂ |
| n-Bu | U | N(Me)n-Bu | T | (CH₂)₂ |
| n-Bu | U | N(nPen)H | T | (CH₂)₂ |
| n-Bu | U | NHCOPh | T | (CH₂)₂ |
| n-Bu | U | N(Me)CO-c-Hex | T | (CH₂)₂ |
| n-Bu | U | NHCONHMe | T | (CH₂)₂ |
| n-Bu | U | N(Me)CONHPh | T | (CH₂)₂ |
| n-Bu | U | NHCONH-c-Hex | T | (CH₂)₂ |
| n-Bu | U | NHCOBz | T | (CH₂)₂ |
| n-Bu | U | J¹ | T | (CH₂)₂ |
| n-Bu | U | NBzCO-n-Bu | T | (CH₂)₂ |
| n-Bu | U | NBzCOO-i-Bu | T | (CH₂)₂ |
| n-Bu | U | NHCO-n-Bu | T | (CH₂)₂ |
| n-Bu | U | NHCOO-i-Bu | T | (CH₂)₂ |
| n-Bu | U | NHCOCF₃ | T | (CH₂)₂ |
| n-Bu | U | NHSO₂CF₃ | T | (CH₂)₂ |
| n-Bu | U | N(Me)Ph | T | (CH₂)₂ |
| n-Bu | U | NHC(=NH)NH₂ | T | (CH₃)₂ |
| n-Bu | U | C(=NH)NH₂ | T | (CH₂)₂ |
| n-Bu | U | CHO | T | (CH₂)₂ |
| n-Bu | U | CN | T | (CH₂)₂ |
| n-Bu | U | U | T | (CH₂)₂ |
| n-Bu | U | COOMe | T | (CH₂)₂ |
| n-Bu | U | CONH₂ | T | (CH₂)₂ |
| n-Bu | U | CONHCOMe | T | (CH₂)₂ |
| n-Bu | U | CH₂NH₂ | T | (CH₂)₂ |
| n-Bu | U | CH₂OH | T | (CH₂)₂ |
| n-Bu | U | CH₂NHCOPh | T | (CH₂)₂ |
| n-Bu | U | CH₂N(nPen)COPh | T | (CH₂)₂ |
| n-Bu | U | CH₂NHCONHMe | T | (CH₂)₂ |
| n-Bu | U | CH₂CONHPh | T | (CH₂)₂ |
| n-Bu | U | CH₂COOH | T | (CH₂)₂ |
| n-Bu | U | Ph | T | (CH₂)₂ |
| n-Bu | U | Bz | T | (CH₂)₂ |
| n-Bu | U | CH₂CH₂Ph | T | (CH₂)₂ |
| n-Bu | U | 2-thienyl | T | (CH₂)₂ |
| n-Bu | U | 3-furyl | T | (CH₂)₂ |
| n-Bu | U | 1-pyrrolyl | T | (CH₂)₂ |
| n-Bu | U | 1-imidazolyl | T | (CH₂)₂ |
| n-Bu | U | 1-pyrazolyl | T | (CH₂)₂ |
| n-Bu | U | 2-pyridyl | T | (CH₂)₂ |
| n-Bu | U | 1-pyrrolidinyl | T | (CH₂)₂ |
| n-Bu | U | 1-piperidyl | T | (CH₂)₂ |
| n-Bu | U | 1-piperazinyl | T | (CH₂)₂ |
| n-Bu | U | 4-morpholinyl | T | (CH₂)₂ |
| n-Bu | U | Ph(2-Cl) | T | (CH₂)₂ |
| n-Bu | U | Ph(3-Me) | T | (CH₂)₂ |
| n-Bu | U | Ph(4-OMe) | T | (CH₂)₂ |
| n-Bu | U | Ph(2-NO₂) | T | (CH₂)₂ |
| n-Bu | U | Ph(3-NH₂) | T | (CH₂)₂ |
| n-Bu | U | Ph(4-NMe₂) | T | (CH₂)₂ |
| n-Bu | U | Ph(4-J²) | T | (CH₂)₂ |
| n-Bu | U | Ph(2-Cl,3-J¹) | T | (CH₂)₂ |
| n-Bu | U | Ph(2-Cl,4-J¹) | T | (CH₂)₂ |
| n-Bu | U | Ph(2-Cl,5-J¹) | T | (CH₂)₂ |

TABLE 1-continued

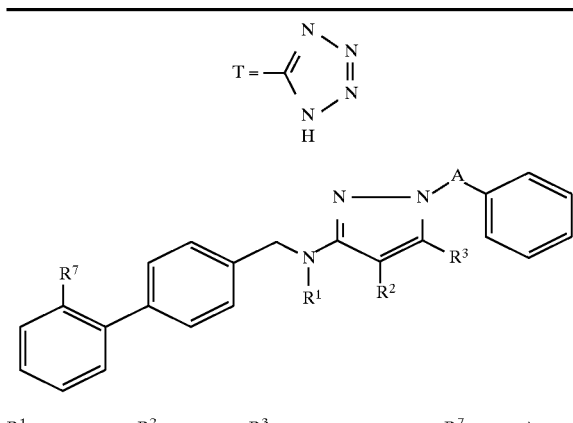

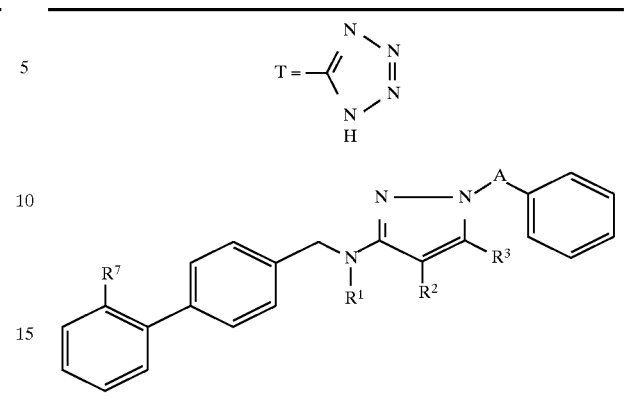

| R¹ | R² | R³ | R⁷ | A |
|---|---|---|---|---|
| n-Bu | U | Ph(2-Cl,6-J¹) | T | (CH₂)₂ |
| n-Bu | U | Ph(3-NHCOPh) | T | (CH₂)₂ |
| n-Bu | U | Ph(4-NHCO-c-Hex) | T | (CH₂)₂ |
| n-Bu | U | Ph(3-NHCONHMe) | T | (CH₂)₂ |
| n-Bu | U | Ph(4-NMeCONHPh) | T | (CH₂)₂ |
| n-Bu | U | Ph(3-NHCO-c-Hex) | T | (CH₂)₂ |
| n-Bu | U | Ph(4-NHCOBz) | T | (CH₂)₂ |
| n-Bu | U | Ph(4-N-(nPen)COPh) | T | (CH₂)₂ |
| n-Bu | U | Ph(3-NHCOnBu) | T | (CH₂)₂ |
| n-Bu | U | Ph(4-NHCOCF₃) | T | (CH₂)₂ |
| n-Bu | U | Ph(3-NHSO₂CF₃) | T | (CH₂)₂ |
| n-Bu | U | Ph(4-NMePh) | T | (CH₂)₂ |
| n-Bu | U | Ph(3-NHC(=NH)NH₂) | T | (CH₂)₂ |
| n-Bu | U | Ph(4-C(=NH)NH₂) | T | (CH₂)₂ |
| n-Bu | U | Ph(3-COOH) | T | (CH₂)₂ |
| n-Bu | U | Ph(4-CONH₂) | T | (CH₂)₂ |
| n-Bu | U | Ph(3-CH₂NH₂) | T | (CH₂)₂ |
| n-Bu | U | Ph(4-CH₂OH) | T | (CH₂)₂ |
| n-Bu | U | Ph(4-CH₂J²) | T | (CH₂)₂ |
| n-Bu | U | Ph(4-CH₂NHCONHMe) | T | (CH₂)₂ |
| n-Bu | U | Ph(4-CH₂CONHPh) | T | (CH₂)₂ |
| n-Bu | U | Ph(4-CH₂COOH) | T | (CH₂)₂ |
| n-Bu | U | Ph (4-Ph) | T | (CH₂)₂ |
| n-Bu | U | CH₂CH₂Ph(2-Cl,5-J¹) | T | (CH₂)₂ |
| n-Bu | U | OH | T | (CH₂)₂ |
| n-Bu | U | OMe | T | (CH₂)₂ |
| n-Bu | U | OPh | T | (CH₂)₂ |
| n-Bu | U | SH | T | (CH₂)₂ |
| n-Bu | U | SPh | T | (CH₂)₂ |
| n-Bu | U | SO₂Ph | T | (CH₂)₂ |
| n-Bu | U | S-n-Bu | T | (CH₂)₂ |
| n-Bu | U | 2-pyrazinyl | T | (CH₂)₂ |
| n-Bu | U | 2-pyrimidinyl | T | (CH₂)₂ |
| n-Bu | U | 3-pyridyl | T | (CH₂)₂ |
| n-Bu | U | 4-pyridyl | T | (CH₂)₂ |
| n-Bu | U | T | T | (CH₂)₂ |
| c-Pr | U | F | T | (CH₂)₂ |
| c-Pr | U | Cl | T | (CH₂)₂ |
| c-Pr | U | Br | T | (CH₂)₂ |
| c-Pr | U | I | T | (CH₂)₂ |
| c-Pr | U | Me | T | (CH₂)₂ |
| c-Pr | U | CF₃ | T | (CH₂)₂ |
| c-Pr | U | Et | T | (CH₂)₂ |
| c-Pr | U | n-Pr | T | (CH₂)₂ |
| c-Pr | U | c-Pr | T | (CH₂)₂ |
| c-Pr | U | NO₂ | T | (CH₂)₂ |
| c-Pr | U | NH₂ | T | (CH₂)₂ |
| c-Pr | U | N(Me)H | T | (CH₂)₂ |
| c-Pr | U | N(Me)₂ | T | (CH₂)₂ |
| c-Pr | U | N(Me)n-Bu | T | (CH₂)₂ |
| c-Pr | U | N(nPen)H | T | (CH₂)₂ |
| c-Pr | U | NHCOPh | T | (CH₂)₂ |
| c-Pr | U | N(Me)CO-c-Hex | T | (CH₂)₂ |
| c-Pr | U | NHCONHMe | T | (CH₂)₂ |
| c-Pr | U | N(Me)CONHPh | T | (CH₂)₂ |
| c-Pr | U | NHCONH-c-Hex | T | (CH₂)₂ |
| c-Pr | U | NHCOBz | T | (CH₂)₂ |
| c-Pr | U | J¹ | T | (CH₃)₂ |
| c-Pr | U | NBzCO-n-Bu | T | (CH₂)₂ |
| c-Pr | U | NBzCOO-i-Bu | T | (CH₂)₂ |
| c-Pr | U | NHCO-n-Bu | T | (CH₂)₂ |
| c-Pr | U | NHCOO-i-Bu | T | (CH₂)₂ |
| c-Pr | U | NHCOCF₃ | T | (CH₂)₂ |
| c-Pr | U | NHSO₂CF₃ | T | (CH₂)₂ |
| c-Pr | U | N(Me)Ph | T | (CH₂)₂ |
| c-Pr | U | NHC(=NH)NH₂ | T | (CH₂)₂ |
| c-Pr | U | C(=NH)NH₂ | T | (CH₂)₂ |
| c-Pr | U | CHO | T | (CH₂)₂ |
| c-Pr | U | U | T | (CH₂)₂ |
| c-Pr | U | COOMe | T | (CH₂)₂ |
| c-Pr | U | CONH₂ | T | (CH₂)₂ |
| c-Pr | U | CONHCOMe | T | (CH₂)₂ |
| c-Pr | U | CH₂NH₂ | T | (CH₂)₂ |
| c-Pr | U | CH₂OH | T | (CH₂)₂ |
| c-Pr | U | CH₂NHCOPh | T | (CH₂)₂ |
| c-Pr | U | CH₂N(nPen)COPh | T | (CH₂)₂ |
| c-Pr | U | CH₂NHCONHMe | T | (CH₂)₂ |
| c-Pr | U | CH₂CONHPh | T | (CH₂)₂ |
| c-Pr | U | CH₂COOH | T | (CH₂)₂ |
| c-Pr | U | Ph | T | (CH₂)₂ |
| c-Pr | U | Bz | T | (CH₂)₂ |
| c-Pr | U | CH₂CH₂Ph | T | (CH₂)₂ |
| c-Pr | U | 2-thienyl | T | (CH₂)₂ |
| c-Pr | U | 3-furyl | T | (CH₂)₂ |
| c-Pr | U | 1-pyrrolyl | T | (CH₂)₂ |
| c-Pr | U | 1-imidazolyl | T | (CH₂)₂ |
| c-Pr | U | 1-pyrazolyl | T | (CH₂)₂ |
| c-Pr | U | 2-pyridyl | T | (CH₂)₂ |
| c-Pr | U | 1-pyrrolidinyl | T | (CH₂)₂ |
| c-Pr | U | 1-piperidyl | T | (CH₂)₂ |
| c-Pr | U | 1-piperazinyl | T | (CH₂)₂ |
| c-Pr | U | 4-morpholinyl | T | (CH₂)₂ |
| c-Pr | U | Ph(2-Cl) | T | (CH₂)₂ |
| c-Pr | U | Ph(3-Me) | T | (CH₂)₂ |
| c-Pr | U | Ph(4-OMe) | T | (CH₂)₂ |
| c-Pr | U | Ph(2-NO₂) | T | (CH₂)₂ |
| c-Pr | U | Ph(3-NH₂) | T | (CH₂)₂ |
| c-Pr | U | Ph(4-NMe₂) | T | (CH₂)₂ |
| c-Pr | U | Ph(4-J²) | T | (CH₂)₂ |
| c-Pr | U | Ph(2-Cl,3-J¹) | T | (CH₂)₂ |
| c-Pr | U | Ph(2-Cl,4-J¹) | T | (CH₂)₂ |
| c-Pr | U | Ph(2-Cl,5-J¹) | T | (CH₂)₂ |
| c-Pr | U | Ph(2-Cl,6-J¹) | T | (CH₂)₂ |
| c-Pr | U | Ph(3-NHCOPh) | T | (CH₂)₂ |
| c-Pr | U | Ph(4-NHCO-c-Hex) | T | (CH₂)₂ |
| c-Pr | U | Ph(3-NHCONHMe) | T | (CH₂)₂ |
| c-Pr | U | Ph(4-NMeCONHPh) | T | (CH₂)₂ |
| c-Pr | U | Ph(4-NHCOBz) | T | (CH₂)₂ |
| c-Pr | U | Ph(4-N(nPen)COPh) | T | (CH₂)₂ |
| c-Pr | U | Ph(3-NHCOnBu) | T | (CH₂)₂ |
| c-Pr | U | Ph(4-NHCOCF₃) | T | (CH₂)₂ |
| c-Pr | U | Ph(3-NHSO₂CF₃) | T | (CH₂)₂ |
| c-Pr | U | Ph(4-NMePh) | T | (CH₂)₂ |
| c-Pr | U | Ph(3- | | |

TABLE 1-continued

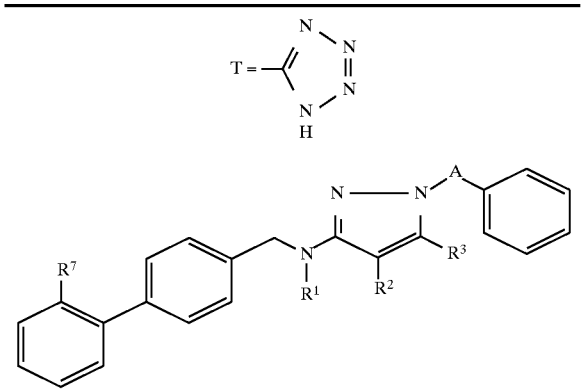

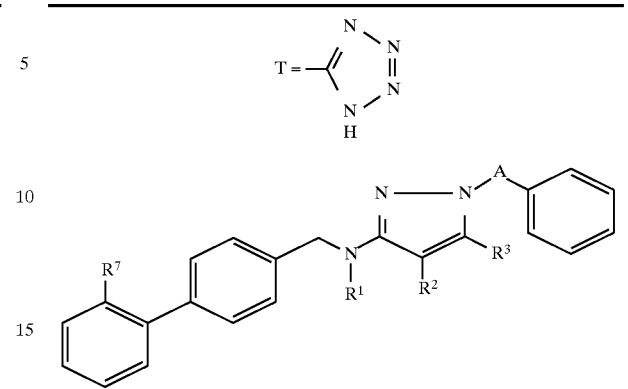

| R¹ | R² | R³ | R⁷ | A |
|---|---|---|---|---|
| | | NHC(=NH)NH₂) | | |
| c-Pr | U | Ph(4-C(=NH)NH₂) | T | (CH₂)₂ |
| c-Pr | U | Ph(3-COOH) | T | (CH₂)₂ |
| c-Pr | U | Ph(4-CONH₂) | T | (CH₂)₂ |
| c-Pr | U | Ph(3-CH₂NH₂) | T | (CH₂)₂ |
| c-Pr | U | Ph(4-CH₂OH) | T | (CH₂)₂ |
| c-Pr | U | Ph(4-CH₂J²) | T | (CH₂)₂ |
| c-Pr | U | Ph(4-CH₂NHCONHMe) | T | (CH₂)₂ |
| c-Pr | U | Ph(4-CH₂CONHPh) | T | (CH₂)₂ |
| c-Pr | U | PH(4-CH₂COOH) | T | (CH₂)₂ |
| c-Pr | U | Ph(4-Ph) | T | (CH₂)₂ |
| c-Pr | U | CH₂CH₂Ph(2-Cl,5-J¹) | T | (CH₂)₂ |
| c-Pr | U | OH | T | (CH₂)₂ |
| c-Pr | U | OMe | T | (CH₂)₂ |
| c-Pr | U | OPh | T | (CH₂)₂ |
| c-Pr | U | SH | T | (CH₂)₂ |
| c-Pr | U | SPh | T | (CH₂)₂ |
| c-Pr | U | SO₂Ph | T | (CH₂)₂ |
| c-Pr | U | S-n-Bu | T | (CH₂)₂ |
| c-Pr | U | 2-pyrazinyl | T | (CH₂)₂ |
| c-Pr | U | 2-pyrimidinyl | T | (CH₂)₂ |
| c-Pr | U | 3-pyridyl | T | (CH₂)₂ |
| c-Pr | U | 4-pyridyl | T | (CH₂)₂ |
| c-Pr | U | T | T | (CH₂)₂ |
| i-Pr | U | F | T | (CH₂)₂ |
| i-Pr | U | Cl | T | (CH₂)₂ |
| i-Pr | U | Br | T | (CH₂)₂ |
| i-Pr | U | I | T | (CH₂)₂ |
| i-Pr | U | Me | T | (CH₂)₂ |
| i-Pr | U | CF₃ | T | (CH₂)₂ |
| i-Pr | U | Et | T | (CH₂)₂ |
| i-Pr | U | n-Pr | T | (CH₂)₂ |
| i-Pr | U | c-Pr | T | (CH₂)₂ |
| i-Pr | U | NO₂ | T | (CH₂)₂ |
| i-Pr | U | NH₂ | T | (CH₂)₂ |
| i-Pr | U | N(Me)H | T | (CH₂)₂ |
| i-Pr | U | N(Me)₂ | T | (CH₂)₂ |
| i-Pr | U | N(Me)n-Bu | T | (CH₂)₂ |
| i-Pr | U | N(nPen)H | T | (CH₂)₂ |
| i-Pr | U | NHCOPh | T | (CH₂)₂ |
| i-Pr | U | J¹ | T | (CH₂)₂ |
| i-Pr | U | NHC(=NH)NH₂ | T | (CH₂)₂ |
| i-Pr | U | C(=NH)NH₂ | T | (CH₂)₂ |
| i-Pr | U | CHO | T | (CH₂)₂ |
| i-Pr | U | CN | T | (CH₂)₂ |
| i-Pr | U | U | T | (CH₂)₂ |
| i-Pr | U | COOMe | T | (CH₂)₂ |
| i-Pr | U | CONH₂ | T | (CH₂)₂ |
| i-Pr | U | CONHCOMe | T | (CH₂)₂ |
| i-Pr | U | CH₂COOH | T | (CH₂)₂ |
| i-Pr | U | Ph | T | (CH₂)₂ |
| i-Pr | U | Bz | T | (CH₂)₂ |
| i-Pr | U | CH₂CH₂Ph | T | (CH₂)₂ |
| n-Pr | T | F | T | (CH₂)₂ |
| n-Pr | T | Cl | T | (CH₂)₂ |
| n-Pr | T | Br | T | (CH₂)₂ |
| n-Pr | T | I | T | (CH₂)₂ |

| R¹ | R² | R³ | R⁷ | A |
|---|---|---|---|---|
| n-Pr | T | Me | T | (CH₂)₂ |
| n-Pr | T | CF₃ | T | (CH₂)₂ |
| n-Pr | T | Et | T | (CH₂)₂ |
| n-Pr | T | n-Pr | T | (CH₂)₂ |
| n-Pr | T | c-Pr | T | (CH₂)₂ |
| n-Pr | T | NO₂ | T | (CH₂)₂ |
| n-Pr | T | NH₂ | T | (CH₂)₂ |
| n-Pr | T | N(Me)H | T | (CH₂)₂ |
| n-Pr | T | N(Me)₂ | T | (CH₂)₂ |
| n-Pr | T | N(Me)n-Bu | T | (CH₂)₂ |
| n-Pr | T | N(nPen)H | T | (CH₂)₂ |
| n-Pr | T | NHCOPh | T | (CH₂)₂ |
| n-Pr | T | J¹ | T | (CH₂)₂ |
| n-Pr | T | NHC(=NH)NH₂ | T | (CH₂)₂ |
| n-Pr | T | C(=NH)NH₂ | T | (CH₂)₂ |
| n-Pr | T | CHO | T | (CH₂)₂ |
| n-Pr | T | CN | T | (CH₂)₂ |
| n-Pr | T | U | T | (CH₂)₂ |
| n-Pr | T | COOMe | T | (CH₂)₂ |
| n-Pr | T | CONH₂ | T | (CH₂)₂ |
| n-Pr | T | CONHCOMe | T | (CH₂)₂ |
| n-Pr | T | CH₂COOH | T | (CH₂)₂ |
| n-Pr | T | Ph | T | (CH₂)₂ |
| n-Pr | T | Bz | T | (CH₂)₂ |
| n-Pr | T | CH₂CH₂Ph | T | (CH₂)₂ |
| n-Pr | T | T | T | (CH₂)₂ |
| 1-Propenyl | U | F | T | (CH₂)₂ |
| 1-Propenyl | U | Cl | T | (CH₂)₂ |
| 1-Propenyl | U | Br | T | (CH₂)₂ |
| 1-Propenyl | U | I | T | (CH₂)₂ |
| 1-Propenyl | U | Me | T | (CH₂)₂ |
| 1-Propenyl | U | CF₃ | T | (CH₂)₂ |
| 1-Propenyl | U | Et | T | (CH₂)₂ |
| 1-Propenyl | U | Br | T | (CH₂)₂ |
| 1-Propenyl | U | I | T | (CH₂)₂ |
| 1-Propenyl | U | Me | T | (CH₂)₂ |
| 1-Propenyl | U | CF₃ | T | (CH₂)₂ |
| 1-Propenyl | U | Et | T | (CH₂)₂ |
| 1-Propenyl | U | n-Pr | T | (CH₂)₂ |
| 1-Propenyl | U | c-Pr | T | (CH₂)₂ |
| 1-Propenyl | U | NO₂ | T | (CH₂)₂ |
| 1-Propenyl | U | NH₂ | T | (CH₂)₂ |
| 1-Propenyl | U | N(Me)H | T | (CH₂)₂ |
| 1-Propenyl | U | N(Me)₂ | T | (CH₂)₂ |
| 1-Propenyl | U | N(Me)n-Bu | T | (CH₂)₂ |
| 1-Propenyl | U | N(nPen)H | T | (CH₂)₂ |
| 1-Propenyl | U | NHCOPh | T | (CH₂)₂ |
| 1-Propenyl | U | N(Me)CO-c-Hex | T | (CH₂)₂ |
| 1-Propenyl | U | NHCONHMe | T | (CH₂)₂ |
| 1-Propenyl | U | N(Me)CONHPh | T | (CH₂)₂ |
| 1-Propenyl | U | NHCONH-c-Hex | T | (CH₂)₂ |
| 1-Propenyl | U | NHCOBz | T | (CH₂)₂ |
| 1-Propenyl | U | J¹ | T | (CH₂)₂ |
| 1-Propenyl | U | NBzCO-n-Bu | T | (CH₂)₂ |
| 1-Propenyl | U | NBzCOO-i-Bu | T | (CH₂)₂ |
| 1-Propenyl | U | NHCO-n-Bu | T | (CH₂)₂ |
| 1-Propenyl | U | NHCOO-i-Bu | T | (CH₂)₂ |
| 1-Propenyl | U | NHCOCF₃ | T | (CH₂)₂ |

TABLE 1-continued

T = tetrazole (5-tetrazolyl, NH)

Structure: biphenyl with R⁷ ortho on one ring; connected via CH₂–N(R¹)–C(=)...pyrazole ring with R², R³ substituents and N–A–phenyl linkage.

| R¹ | R² | R³ | R⁷ | A |
|---|---|---|---|---|
| 1-Propenyl | U | NHSO₂CF₃ | T | (CH₂)₂ |
| 1-Propenyl | U | N(Me)Ph | T | (CH₂)₂ |
| 1-Propenyl | U | NHC(=NH)NH₂ | T | (CH₂)₂ |
| 1-Propenyl | U | C(=NH)NH₂ | T | (CH₂)₂ |
| 1-Propenyl | U | CHO | T | (CH₂)₂ |
| 1-Propenyl | U | CN | T | (CH₂)₂ |
| 1-Propenyl | U | U | T | (CH₂)₂ |
| 1-Propenyl | U | COOMe | T | (CH₂)₂ |
| 1-Propenyl | U | CONH₂ | T | (CH₂)₂ |
| 1-Propenyl | U | CONHCOMe | T | (CH₂)₂ |
| 1-Propenyl | U | CH₂NH₂ | T | (CH₂)₂ |
| 1-Propenyl | U | CH₂OH | T | (CH₂)₂ |
| 1-Propenyl | U | CH₂NHCOPh | T | (CH₂)₂ |
| 1-Propenyl | U | CH₂N(nPen)COPh | T | (CH₂)₂ |
| 1-Propenyl | U | CH₂NHCONHMe | T | (CH₂)₂ |
| 1-Propenyl | U | CH₂CONHPh | T | (CH₂)₂ |
| 1-Propenyl | U | CH₂COOH | T | (CH₂)₂ |
| 1-Propenyl | U | Ph | T | (CH₂)₂ |
| 1-Propenyl | U | Bz | T | (CH₂)₂ |
| 1-Propenyl | U | CH₂CH₂Ph | T | (CH₂)₂ |
| 1-Propenyl | U | 2-thienyl | T | (CH₂)₂ |
| 1-Propenyl | U | 3-furyl | T | (CH₂)₂ |
| 1-Propenyl | U | 1-pyrrolyl | T | (CH₂)₂ |
| 1-Propenyl | U | 1-imidazolyl | T | (CH₂)₂ |
| 1-Propenyl | U | 1-pyrazolyl | T | (CH₂)₂ |
| 1-Propenyl | U | 2-pyridyl | T | (CH₂)₂ |
| 1-Propenyl | U | 1-pyrrolidinyl | T | (CH₂)₂ |
| 1-Propenyl | U | 1-piperidyl | T | (CH₂)₂ |
| 1-Propenyl | U | 1-piperazinyl | T | (CH₂)₂ |
| 1-Propenyl | U | 4-morpholinyl | T | (CH₂)₂ |
| 1-Propenyl | U | Ph(2-Cl) | T | (CH₂)₂ |
| 1-Propenyl | U | Ph(3-Me) | T | (CH₂)₂ |
| 1-Propenyl | U | Ph(4-OMe) | T | (CH₂)₂ |
| 1-Propenyl | U | Ph(2-NO₂) | T | (CH₂)₂ |
| 1-Propenyl | U | Ph(3-NH₂) | T | (CH₂)₂ |
| 1-Propenyl | U | Ph(4-NMe₂) | T | (CH₂)₂ |
| 1-Propenyl | U | Ph(4-J²) | T | (CH₂)₂ |
| 1-Propenyl | U | Ph(2-Cl,3-J¹) | T | (CH₂)₂ |
| 1-Propenyl | U | Ph(2-Cl,4-J¹) | T | (CH₂)₂ |
| 1-Propenyl | U | Ph(2-Cl,5-J¹) | T | (CH₂)₂ |
| 1-Propenyl | U | Ph(2-Cl,6-J¹) | T | (CH₂)₂ |
| 1-Propenyl | U | Ph(3-NHCOPh) | T | (CH₂)₂ |
| 1-Propenyl | U | Ph(4-NHCO-c-Hex) | T | (CH₂)₂ |
| 1-Propenyl | U | Ph(3-NHCONHMe) | T | (CH₂)₂ |
| 1-Propenyl | U | Ph(4-NMeCONHPh) | T | (CH₂)₂ |
| 1-Propenyl | U | Ph(3-NHCONH-c-Hex) | T | (CH₂)₂ |
| 1-Propenyl | U | Ph(4-NHCOBz) | T | (CH₂)₂ |
| 1-Propenyl | U | Ph(4-N(nPen)COPh) | T | (CH₂)₂ |
| 1-Propenyl | U | Ph(3-NHCOnBu) | T | (CH₂)₂ |
| 1-Propenyl | U | Ph(4-NHCOCF₃) | T | (CH₂)₂ |
| 1-Propenyl | U | Ph(3-NHSO₂CF₃) | T | (CH₂)₂ |
| 1-Propenyl | U | Ph(4-NMePh) | T | (CH₂)₂ |
| 1-Propenyl | U | Ph(3-NHC(=NH)NH₂) | T | (CH₂)₂ |
| 1-Propenyl | U | Ph(4-C(=NH)NH₂) | T | (CH₂)₂ |
| 1-Propenyl | U | Ph(3-COOH) | T | (CH₂)₂ |
| 1-Propenyl | U | Ph(4-CONH₂) | T | (CH₂)₂ |
| 1-Propenyl | U | Ph(3-CH₂NH₂) | T | (CH₂)₂ |
| 1-Propenyl | U | Ph(4-CH₂OH) | T | (CH₂)₂ |
| 1-Propenyl | U | Ph(4-CH₂J²) | T | (CH₂)₂ |
| 1-Propenyl | U | Ph(4-CH₂NHCONHMe) | T | (CH₂)₂ |
| 1-Propenyl | U | Ph(4-CH₂CONHPh) | T | (CH₂)₂ |
| 1-Propenyl | U | Ph(4-CH₂COOH) | T | (CH₂)₂ |
| 1-Propenyl | U | Ph(4-Ph) | T | (CH₂)₂ |
| 1-Propenyl | U | CH₂CH₂Ph(2-Cl,5-J¹) | T | (CH₂)₂ |
| 1-Propenyl | U | OH | T | (CH₂)₂ |
| 1-Propenyl | U | OMe | T | (CH₂)₂ |
| 1-Propenyl | U | OPh | T | (CH₂)₂ |
| 1-Propenyl | U | SH | T | (CH₂)₂ |
| 1-Propenyl | U | SPh | T | (CH₂)₂ |
| 1-Propenyl | U | SO₂Ph | T | (CH₂)₂ |
| 1-Propenyl | U | S-n-Bu | T | (CH₂)₂ |
| 1-Propenyl | U | 2-pyrazinyl | T | (CH₂)₂ |
| 1-Propenyl | U | 2-pyrimidinyl | T | (CH₂)₂ |
| 1-Propenyl | U | 3-pyridyl | T | (CH₂)₂ |
| 1-Propenyl | U | 4-pyridyl | T | (CH₂)₂ |
| 1-Propenyl | U | T | T | (CH₂)₂ |
| 2-Propenyl | U | F | T | (CH₂)₂ |
| 2-Propenyl | U | Cl | T | (CH₂)₂ |
| 2-Propenyl | U | Br | T | (CH₂)₂ |
| 2-Propenyl | U | I | T | (CH₂)₂ |
| 2-Propenyl | U | Me | T | (CH₂)₂ |
| 2-Propenyl | U | CF₃ | T | (CH₂)₂ |
| 2-Propenyl | U | Et | T | (CH₂)₂ |
| 2-Propenyl | U | n-Pr | T | (CH₂)₂ |
| 2-Propenyl | U | c-Pr | T | (CH₂)₂ |
| 2-Propenyl | U | NO₂ | T | (CH₂)₂ |
| 2-Propenyl | U | NH₂ | T | (CH₂)₂ |
| 2-Propenyl | U | N(ME)H | T | (CH₂)₂ |
| 2-Propenyl | U | N(Me)₂ | T | (CH₂)₂ |
| 2-Propenyl | U | N(Me)n-Bu | T | (CH₂)₂ |
| 2-Propenyl | U | N(nPen)H | T | (CH₂)₂ |
| 2-Propenyl | U | NHCOPh | T | (CH₂)₂ |
| 2-Propenyl | U | N(Me)CO-c-Hex | T | (CH₂)₂ |
| 2-Propenyl | U | NHCONHMe | T | (CH₂)₂ |
| 2-Propenyl | U | N(Me)CONHPh | T | (CH₂)₂ |
| 2-Propenyl | U | NHCONH-c-Hex | T | (CH₂)₂ |
| 2-Propenyl | U | NHCOBz | T | (CH₂)₂ |
| 2-Propenyl | U | J¹ | T | (CH₂)₂ |
| 2-Propenyl | U | NBzCO-n-Bu | T | (CH₂)₂ |
| 2-Propenyl | U | NBzCOO-i-Bu | T | (CH₂)₂ |
| 2-Propenyl | U | NHCO-n-Bu | T | (CH₂)₂ |
| 2-Propenyl | U | NHCOO-i-Bu | T | (CH₂)₂ |
| 2-Propenyl | U | NHCOCF₃ | T | (CH₂)₂ |
| 2-Propenyl | U | NHSO₂CF₃ | T | (CH₂)₂ |
| 2-Propenyl | U | N(Me)Ph | T | (CH₂)₂ |
| 2-Propenyl | U | NHC(=NH)NH₂ | T | (CH₂)₂ |
| 2-Propenyl | U | C(=NH)NH₂ | T | (CH₂)₂ |
| 2-Propenyl | U | CHO | T | (CH₂)₂ |
| 2-Propenyl | U | CN | T | (CH₂)₂ |
| 2-Propenyl | U | U | T | (CH₂)₂ |
| 2-Propenyl | U | COOMe | T | (CH₂)₂ |
| 2-Propenyl | U | CONH₂ | T | (CH₂)₂ |
| 2-Propenyl | U | CONHCOMe | T | (CH₂)₂ |
| 2-Propenyl | U | CH₂NH₂ | T | (CH₂)₂ |

TABLE 1-continued

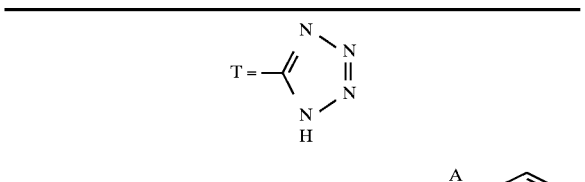

| R¹ | R² | R³ | R⁷ | A |
|---|---|---|---|---|
| 2-Propenyl | U | CH₂OH | T | (CH₂)₂ |
| 2-Propenyl | U | CH₂NHCOPh | T | (CH₂)₂ |
| 2-Propenyl | U | CH₂N(nPen)COPh | T | (CH₂)₂ |
| 2-Propenyl | U | CH₂NHCONHMe | T | (CH₂)₂ |
| 2-Propenyl | U | CH₂CONHPh | T | (CH₂)₂ |
| 2-Propenyl | U | CH₂COOH | T | (CH₂)₂ |
| 2-Propenyl | U | Ph | T | (CH₂)₂ |
| 2-Propenyl | U | Bz | T | (CH₂)₂ |
| 2-Propenyl | U | CH₂CH₂Ph | T | (CH₂)₂ |
| 2-Propenyl | U | 2-thienyl | T | (CH₂)₂ |
| 2-Propenyl | U | 3-furyl | T | (CH₂)₂ |
| 2-Propenyl | U | 1-pyrrolyl | T | (CH₂)₂ |
| 2-Propenyl | U | 1-imidazolyl | T | (CH₂)₂ |
| 2-Propenyl | U | 1-pyrazolyl | T | (CH₂)₂ |
| 2-Propenyl | U | 2-pyridyl | T | (CH₂)₂ |
| 2-Propenyl | U | 1-pyrrolidinyl | T | (CH₂)₂ |
| 2-Propenyl | U | 1-piperidyl | T | (CH₂)₂ |
| 2-Propenyl | U | 1-piperazinyl | T | (CH₂)₂ |
| 2-Propenyl | U | 4-morpholinyl | T | (CH₂)₂ |
| 2-Propenyl | U | Ph(2-Cl) | T | (CH₂)₂ |
| 2-Propenyl | U | Ph(3-Me) | T | (CH₂)₂ |
| 2-Propenyl | U | Ph(4-OMe) | T | (CH₂)₂ |
| 2-Propenyl | U | Ph(3-NH₂) | T | (CH₂)₂ |
| 2-Propenyl | U | Ph(2-NO₂) | T | (CH₂)₂ |
| 2-Propenyl | U | Ph(4-NMe₂) | T | (CH₂)₂ |
| 2-Propenyl | U | Ph(4-J²) | T | (CH₂)₂ |
| 2-Propenyl | U | Ph(2-Cl,3-J¹) | T | (CH₂)₂ |
| 2-Propenyl | U | Ph(2-Cl,4-J¹) | T | (CH₂)₂ |
| 2-Propenyl | U | Ph(3-Cl,5-J¹) | T | (CH₂)₂ |
| 2-Propenyl | U | Ph(2-Cl,6-J¹) | T | (CH₂)₂ |
| 2-Propenyl | U | Ph(3-NHCOPh) | T | (CH₂)₂ |
| 2-Propenyl | U | Ph(4-NHCO-c-Hex) | T | (CH₂)₂ |
| 2-Propenyl | U | Ph(3-NHCONHMe) | T | (CH₂)₂ |
| 2-Propenyl | U | Ph(4-NMeCONHPh) | T | (CH₂)₂ |
| 2-Propenyl | U | Ph(3-NHCONH-c-Hex) | T | (CH₂)₂ |
| 2-Propenyl | U | Ph(4-NHCOBz) | T | (CH₂)₂ |
| 2-Propenyl | U | Ph(4-N(nPen)COPh) | T | (CH₂)₂ |
| 2-Propenyl | U | Ph(3-NHCOnBu) | T | (CH₂)₂ |
| 2-Propenyl | U | Ph(4-NHCOCF₃) | T | (CH₂)₂ |
| 2-Propenyl | U | Ph(3-NHSO₂CF₃) | T | (CH₂)₂ |
| 2-Propenyl | U | Ph(4-NMePh) | T | (CH₂)₂ |
| 2-Propenyl | U | Ph(3-NHC(=NH)NH₂) | T | (CH₂)₂ |
| 2-Propenyl | U | Ph(4-C(=NH)NH₂) | T | (CH₂)₂ |
| 2-Propenyl | U | Ph(3-COOH) | T | (CH₂)₂ |
| 2-Propenyl | U | Ph(4-CONH₂) | T | (CH₂)₂ |
| 2-Propenyl | U | Ph(3-CH₂NH₂) | T | (CH₂)₂ |
| 2-Propenyl | U | Ph(4-CH₂OH) | T | (CH₂)₂ |
| 2-Propenyl | U | Ph(4-CH₂J²) | T | (CH₂)₂ |
| 2-Propenyl | U | Ph(4-CH₂NHCONHMe) | T | (CH₂)₂ |
| 2-Propenyl | U | Ph(4-CH₂CONHPh) | T | (CH₂)₂ |
| 2-Propenyl | U | Ph(4-CH₂COOH) | T | (CH₂)₂ |
| 2-Propenyl | U | Ph(4-Ph) | T | (CH₂)₂ |
| 2-Propenyl | U | CH₂CH₂Ph(2-Cl,5-J¹) | T | (CH₂)₂ |
| 2-Propenyl | U | OH | T | (CH₂)₂ |
| 2-Propenyl | U | OMe | T | (CH₂)₂ |

TABLE 1-continued

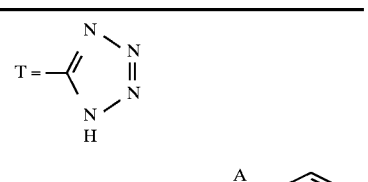

| R¹ | R² | R³ | R⁷ | A |
|---|---|---|---|---|
| 2-Propenyl | U | OPh | T | (CH₂)₂ |
| 2-Propenyl | U | SH | T | (CH₂)₂ |
| 2-Propenyl | U | SPh | T | (CH₂)₂ |
| 2-Propenyl | U | SO₂Ph | T | (CH₂)₂ |
| 2-Propenyl | U | S-n-Bu | T | (CH₂)₂ |
| 2-Propenyl | U | 2-pyrazinyl | T | (CH₂)₂ |
| 2-Propenyl | U | 2-pyrimidinyl | T | (CH₂)₂ |
| 2-Propenyl | U | 3-pyridyl | T | (CH₂)₂ |
| 2-Propenyl | U | 4-pyridyl | T | (CH₂)₂ |
| 2-Propenyl | U | T | T | (CH₂)₂ |
| 1-Butenyl | U | F | T | (CH₂)₂ |
| 1-Butenyl | U | Cl | T | (CH₂)₂ |
| 1-Butenyl | U | Br | T | (CH₂)₂ |
| 1-Butenyl | U | I | T | (CH₂)₂ |
| 1-Butenyl | U | Me | T | (CH₂)₂ |
| 1-Butenyl | U | CF₃ | T | (CH₂)₂ |
| 1-Butenyl | U | Et | T | (CH₂)₂ |
| 1-Butenyl | U | n-Pr | T | (CH₂)₂ |
| 1-Butenyl | U | c-Pr | T | (CH₂)₂ |
| 1-Butenyl | U | NO₂ | T | (CH₂)₂ |
| 1-Butenyl | U | NH₂ | T | (CH₂)₂ |
| 1-Butenyl | U | N(Me)H | T | (CH₂)₂ |
| 1-Butenyl | U | N(Me)₂ | T | (CH₂)₂ |
| 1-Butenyl | U | N(Me)n-Bu | T | (CH₂)₂ |
| 1-Butenyl | U | N(nPen)H | T | (CH₂)₂ |
| 1-Butenyl | U | NHCOPh | T | (CH₂)₂ |
| 1-Butenyl | U | J¹ | T | (CH₂)₂ |
| 1-Butenyl | U | NHC(=NH)NH₂ | T | (CH₂)₂ |
| 1-Butenyl | U | C(=NH)NH₂ | T | (CH₂)₂ |
| 1-Butenyl | U | CHO | T | (CH₂)₂ |
| 1-Butenyl | U | CN | T | (CH₂)₂ |
| 1-Butenyl | U | U | T | (CH₂)₂ |
| 1-Butenyl | U | COOMe | T | (CH₂)₂ |
| 1-Butenyl | U | CONH₂ | T | (CH₂)₂ |
| 1-Butenyl | U | CONHCOMe | T | (CH₂)₂ |
| 1-Butenyl | U | CH₂COOH | T | (CH₂)₂ |
| 1-Butenyl | U | Ph | T | (CH₂)₂ |
| 1-Butenyl | U | Bz | T | (CH₂)₂ |
| 1-Butenyl | U | CH₂CH₂Ph | T | (CH₂)₂ |
| 1-Butenyl | U | 2-thienyl | T | (CH₂)₂ |
| 1-Butenyl | U | 3-furyl | T | (CH₂)₂ |
| 1-Butenyl | U | Ph(4-J²) | T | (CH₂)₂ |
| 1-Butenyl | U | Ph(2-Cl,3-J¹) | T | (CH₂)₂ |
| 1-Butenyl | U | Ph(2-Cl,4-J¹) | T | (CH₂)₂ |
| 1-Butenyl | U | Ph(2-Cl,5-J¹) | T | (CH₂)₂ |
| 1-Butenyl | U | Ph(2-Cl,6-J¹) | T | (CH₂)₂ |
| 1-Butenyl | U | Ph(3-NHCOPh) | T | (CH₂)₂ |
| 1-Butenyl | U | Ph(4-NHCO-c-Hex) | T | (CH₂)₂ |
| 1-Butenyl | U | Ph(3-NHCONHMe) | T | (CH₂)₂ |
| 1-Butenyl | U | Ph-4-NMeCONHPh) | T | (CH₂)₂ |
| 1-Butenyl | U | Ph(3-NHCONH-c-Hex) | T | (CH₂)₂ |
| 1-Butenyl | U | Ph(4-NHCOBz) | T | (CH₂)₂ |
| 1-Butenyl | U | Ph(4-N(nPen)COPh) | T | (CH₂)₂ |
| 1-Butenyl | U | Ph(3-NHCOnBu) | T | (CH₂)₂ |
| 1-Butenyl | U | Ph(4-NHCOCF₃) | T | (CH₂)₂ |
| 1-Butenyl | U | Ph(3-NHSO₂CF₃) | T | (CH₂)₂ |
| 1-Butenyl | U | Ph(4-NMePh) | T | (CH₂)₂ |

TABLE 1-continued

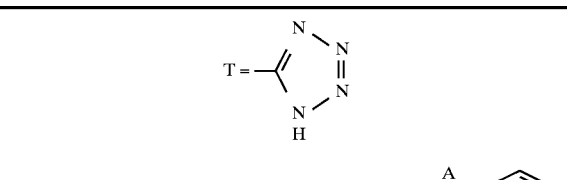

| R¹ | R² | R³ | R⁷ | A |
|---|---|---|---|---|
| 1-Butenyl | U | Ph(3-NHC(=NH)NH$_2$) | T | (CH$_2$)$_2$ |
| 1-Butenyl | U | Ph(4-C(=NH)NH$_2$) | T | (CH$_2$)$_2$ |
| 1-Butenyl | U | Ph(3-COOH) | T | (CH$_2$)$_2$ |
| 1-Butenyl | U | Ph(4-CONH$_2$) | T | (CH$_2$)$_2$ |
| 1-Butenyl | U | Ph(3-CH$_2$NH$_2$) | T | (CH$_2$)$_2$ |
| 1-Butenyl | U | Ph(4-CH$_2$OH) | T | (CH$_2$)$_2$ |
| 1-Butenyl | U | Ph(4-CH$_2$J$^2$) | T | (CH$_2$)$_2$ |
| 1-Butenyl | U | Ph(4-CH$_2$NHCONHMe) | T | (CH$_2$)$_2$ |
| 1-Butenyl | U | Ph(4-CH$_2$CONHPh) | T | (CH$_2$)$_2$ |
| 1-Butenyl | U | Ph(4-CH$_2$COOH) | T | (CH$_2$)$_2$ |
| 1-Butenyl | U | Ph(4-Ph) | T | (CH$_2$)$_2$ |
| 1-Butenyl | U | CH$_2$CH$_2$Ph(2-Cl,5-J$^1$) | T | (CH$_2$)$_2$ |
| 1-Butenyl | U | OH | T | (CH$_2$)$_2$ |
| 1-Butenyl | U | T | T | (CH$_2$)$_2$ |
| 2-Butenyl | U | F | T | (CH$_2$)$_2$ |
| 2-Butenyl | U | Cl | T | (CH$_2$)$_2$ |
| 2-Butenyl | U | Br | T | (CH$_2$)$_2$ |
| 2-Butenyl | U | I | T | (CH$_2$)$_2$ |
| 2-Butenyl | U | Me | T | (CH$_2$)$_2$ |
| 2-Butenyl | U | CF$_3$ | T | (CH$_2$)$_2$ |
| 2-Butenyl | U | Et | T | (CH$_2$)$_2$ |
| 2-Butenyl | U | n-Pr | T | (CH$_2$)$_2$ |
| 2-Butenyl | U | c-Pr | T | (CH$_2$)$_2$ |
| 2-Butenyl | U | NO$_2$ | T | (CH$_2$)$_2$ |
| 2-Butenyl | U | NH$_2$ | T | (CH$_2$)$_2$ |
| 2-Butenyl | U | N(Me)H | T | (CH$_2$)$_2$ |
| 2-Butenyl | U | N(Me)$_2$ | T | (CH$_2$)$_2$ |
| 2-Butenyl | U | N(Me)n-Bu | T | (CH$_2$)$_2$ |
| 2-Butenyl | U | N(nPen)H | T | (CH$_2$)$_2$ |
| 2-Butenyl | U | NHCOPh | T | (CH$_2$)$_2$ |
| 2-Butenyl | U | N(Me)CO-c-Hex | T | (CH$_2$)$_2$ |
| 2-Butenyl | U | NHCONHMe | T | (CH$_2$)$_2$ |
| 2-Butenyl | U | N(Me)CONHPh | T | (CH$_2$)$_2$ |
| 2-Butenyl | U | J$^1$ | T | (CH$_2$)$_2$ |
| 2-Butenyl | U | NHC(=NH)NH$_2$ | T | (CH$_2$)$_2$ |
| 2-Butenyl | U | C(=NH)NH$_2$ | T | (CH$_2$)$_2$ |
| 2-Butenyl | U | CHO | T | (CH$_2$)$_2$ |
| 2-Butenyl | U | CN | T | (CH$_2$)$_2$ |
| 2-Butenyl | U | U | T | (CH$_2$)$_2$ |
| 2-Butenyl | U | COOMe | T | (CH$_2$)$_2$ |
| 2-Butenyl | U | CONH$_2$ | T | (CH$_2$)$_2$ |
| 2-Butenyl | U | CONHCOMe | T | (CH$_2$)$_2$ |
| 2-Butenyl | U | CH$_2$COOH | T | (CH$_2$)$_2$ |
| 2-Butenyl | U | Ph | T | (CH$_2$)$_2$ |
| 2-Butenyl | U | Bz | T | (CH$_2$)$_2$ |
| 2-Butenyl | U | CH$_2$CH$_2$Ph | T | (CH$_2$)$_2$ |
| 2-Butenyl | U | 2-thienyl | T | (CH$_2$)$_2$ |
| 2-Butenyl | U | 3-furyl | T | (CH$_2$)$_2$ |
| 2-Butenyl | U | Ph(4-J$^2$) | T | (CH$_2$)$_2$ |
| 2-Butenyl | U | Ph(2-Cl,3-J$^1$) | T | (CH$_2$)$_2$ |
| 2-Butenyl | U | Ph(2-Cl,4-J$^1$) | T | (CH$_2$)$_2$ |
| 2-Butenyl | U | Ph(2-Cl,5-J$^1$) | T | (CH$_2$)$_2$ |
| 2-Butenyl | U | Ph(2-Cl,6-J$^1$) | T | (CH$_2$)$_2$ |
| 2-Butenyl | U | Ph(3-NHCOPh) | T | (CH$_2$)$_2$ |
| 2-Butenyl | U | Ph(4-NHCO-c-Hex) | T | (CH$_2$)$_2$ |
| 2-Butenyl | U | Ph(3-NHCONHMe) | T | (CH$_2$)$_2$ |

TABLE 1-continued

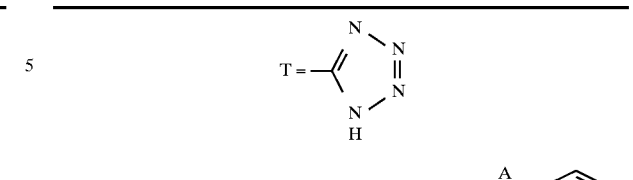

| R¹ | R² | R³ | R⁷ | A |
|---|---|---|---|---|
| 2-Butenyl | U | Ph(4-NMeCONHPh) | T | (CH$_2$)$_2$ |
| 2-Butenyl | U | Ph(3-NHCONH-c-Hex) | T | (CH$_2$)$_2$ |
| 2-Butenyl | U | Ph(4-NHCOBz) | T | (CH$_2$)$_2$ |
| 2-Butenyl | U | Ph(4-N(nPen)COPh) | T | (CH$_2$)$_2$ |
| 2-Butenyl | U | Ph(3-NHCOnBu) | T | (CH$_2$)$_2$ |
| 2-Butenyl | U | Ph(4-NHCOCF$_2$) | T | (CH$_2$)$_2$ |
| 2-Butenyl | U | Ph(3-NHSO$_2$CF$_3$) | T | (CH$_2$)$_2$ |
| 2-Butenyl | U | Ph(4-NMePh) | T | (CH$_2$)$_2$ |
| 2-Butenyl | U | Ph(3-NHC(=NH)NH$_2$) | T | (CH$_2$)$_2$ |
| 2-Butenyl | U | Ph(4-C(=NH)NH$_2$) | T | (CH$_2$)$_2$ |
| 2-Butenyl | U | Ph(3-COOH) | T | (CH$_2$)$_2$ |
| 2-Butenyl | U | Ph(4-CONH$_2$) | T | (CH$_2$)$_2$ |
| 2-Butenyl | U | Ph(3-CH$_2$NH$_2$) | T | (CH$_2$)$_2$ |
| 2-Butenyl | U | Ph(4-CH$_2$OH) | T | (CH$_2$)$_2$ |
| 2-Butenyl | U | Ph(4-CH$_2$J$^2$) | T | (CH$_2$)$_2$ |
| 2-Butenyl | U | Ph(4-CH$_2$NHCONHMe) | T | (CH$_2$)$_2$ |
| 2-Butenyl | U | Ph(4-CH$_2$CONHPh) | T | (CH$_2$)$_2$ |
| 2-Butenyl | U | Ph(4-CH$_2$COOH) | T | (CH$_2$)$_2$ |
| 2-Butenyl | U | Ph(4-Ph) | T | (CH$_2$)$_2$ |
| 2-Butenyl | U | CH$_2$CH$_2$Ph(2-Cl,5-J$^1$) | T | (CH$_2$)$_2$ |
| 2-Butenyl | U | T | T | (CH$_2$)$_2$ |
| 3-Butenyl | U | F | T | (CH$_2$)$_2$ |
| 3-Butenyl | U | Cl | T | (CH$_2$)$_2$ |
| 3-Butenyl | U | Br | T | (CH$_2$)$_2$ |
| 3-Butenyl | U | I | T | (CH$_2$)$_2$ |
| 3-Butenyl | U | Me | T | (CH$_2$)$_2$ |
| 3-Butenyl | U | CF$_3$ | T | (CH$_2$)$_2$ |
| 3-Butenyl | U | Et | T | (CH$_2$)$_2$ |
| 3-Butenyl | U | n-Pr | T | (CH$_2$)$_2$ |
| 3-Butenyl | U | c-Pr | T | (CH$_2$)$_2$ |
| 3-Butenyl | U | NO$_2$ | T | (CH$_2$)$_2$ |
| 3-Butenyl | U | NH$_2$ | T | (CH$_2$)$_2$ |
| 3-Butenyl | U | N(Me)H | T | (CH$_2$)$_2$ |
| 3-Butenyl | U | N(Me)$_2$ | T | (CH$_2$)$_2$ |
| 3-Butenyl | U | N(Me)n-Bu | T | (CH$_2$)$_2$ |
| 3-Butenyl | U | N(nPen)H | T | (CH$_2$)$_2$ |
| 3-Butenyl | U | NHCOPh | T | (CH$_2$)$_2$ |
| 3-Butenyl | U | J$^1$ | T | (CH$_2$)$_2$ |
| 3-Butenyl | U | NHC(=NH)NH$_2$ | T | (CH$_2$)$_2$ |
| 3-Butenyl | U | C(=NH)NH$_2$ | T | (CH$_2$)$_2$ |
| 3-Butenyl | U | CHO | T | (CH$_2$)$_2$ |
| 3-Butenyl | U | CN | T | (CH$_2$)$_2$ |
| 3-Butenyl | U | U | T | (CH$_2$)$_2$ |
| 3-Butenyl | U | COOMe | T | (CH$_2$)$_2$ |
| 3-Butenyl | U | CONH$_2$ | T | (CH$_2$)$_2$ |
| 3-Butenyl | U | CONHCOMe | T | (CH$_2$)$_2$ |
| 3-Butenyl | U | CH$_2$COOH | T | (CH$_2$)$_2$ |
| 3-Butenyl | U | Ph | T | (CH$_2$)$_2$ |
| 3-Butenyl | U | Bz | T | (CH$_2$)$_2$ |
| 3-Butenyl | U | CH$_2$CH$_2$Ph | T | (CH$_2$)$_2$ |
| 3-Butenyl | U | 2-thienyl | T | (CH$_2$)$_2$ |
| 3-Butenyl | U | 3-furyl | T | (CH$_2$)$_2$ |
| 3-Butenyl | U | Ph(4-J$^2$) | T | (CH$_2$)$_2$ |
| 3-Butenyl | U | Ph(2-Cl,3-J$^1$) | T | (CH$_2$)$_2$ |
| 3-Butenyl | U | Ph(2-Cl,4-J$^1$) | T | (CH$_2$)$_2$ |

TABLE 1-continued

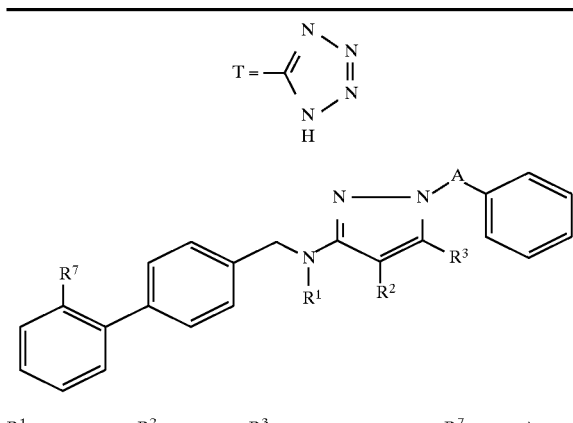

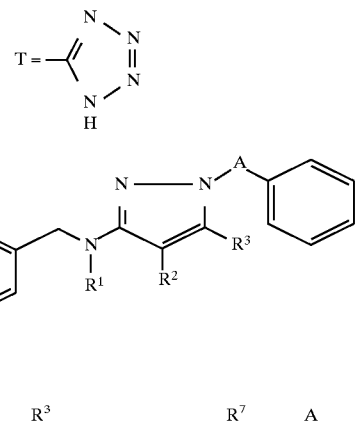

| R¹ | R² | R³ | R⁷ | A |
|---|---|---|---|---|
| 3-Butenyl | U | Ph(2-Cl,5-J¹) | T | (CH₂)₂ |
| 3-Butenyl | U | Ph(2-Cl,6-J¹) | T | (CH₂)₂ |
| 3-Butenyl | U | Ph(3-NHCOPh) | T | (CH₂)₂ |
| 3-Butenyl | U | Ph(4-NHCO-c-Hex) | T | (CH₂)₂ |
| 3-Butenyl | U | Ph(3-NHCONHMe) | T | (CH₂)₂ |
| 3-Butenyl | U | Ph(4-NMeCONHPh) | T | (CH₂)₂ |
| 3-Butenyl | U | Ph(3-NHCONH-c-Hex) | T | (CH₂)₂ |
| 3-Butenyl | U | Ph(4-NHCOBz) | T | (CH₂)₂ |
| 3-Butenyl | U | Ph(4-N(nPen)COPh) | T | (CH₂)₂ |
| 3-Butenyl | U | Ph(3-NHCOnBu) | T | (CH₂)₂ |
| 3-Butenyl | U | Ph(4-NHCOCF₃) | T | (CH₂)₂ |
| 3-Butenyl | U | Ph(3-NHSO₂CF₃) | T | (CH₂)₂ |
| 3-Butenyl | U | Ph(4-NMePh) | T | (CH₂)₂ |
| 3-Butenyl | U | Ph(3-NHC(=NH)NH₂) | T | (CH₂)₂ |
| 3-Butenyl | U | Ph(4-C(=NH)NH₂) | T | (CH₂)₂ |
| 3-Butenyl | U | Ph(3-COOH) | T | (CH₂)₂ |
| 3-Butenyl | U | Ph(4-CONH₂) | T | (CH₂)₂ |
| 3-Butenyl | U | Ph(3-CH₂NH₂) | T | (CH₂)₂ |
| 3-Butenyl | U | Ph(4-CH₂OH) | T | (CH₂)₂ |
| 3-Butenyl | U | Ph(4-CH₂J²) | T | (CH₂)₂ |
| 3-Butenyl | U | Ph(4-CH₂NHCONHMe) | T | (CH₂)₂ |
| 3-Butenyl | U | Ph(4-CH₂CONHPh) | T | (CH₂)₂ |
| 3-Butenyl | U | Ph(4-CH₂COOH) | T | (CH₂)₂ |
| 3-Butenyl | U | Ph(4-Ph) | T | (CH₂)₂ |
| 3-Butenyl | U | CH₂CH₂Ph(2-Cl,5-J¹) | T | (CH₂)₂ |
| 3-Butenyl | U | T | T | (CH₂)₂ |
| C₂H₅CH(OH) | U | F | T | (CH₂)₂ |
| C₂H₅CH(OH) | U | Cl | T | (CH₂)₂ |
| C₂H₅CH(OH) | U | Br | T | (CH₂)₂ |
| C₂H₅CH(OH) | U | I | T | (CH₂)₂ |
| C₂H₅CH(OH) | U | Me | T | (CH₂)₂ |
| C₂H₅CH(OH) | U | CF₃ | T | (CH₂)₂ |
| C₂H₅CH(OH) | U | Et | T | (CH₂)₂ |
| C₂H₅CH(OH) | U | n-Pr | T | (CH₂)₂ |
| C₂H₅CH(OH) | U | c-Pr | T | (CH₂)₂ |
| C₂H₅CH(OH) | U | NO₂ | T | (CH₂)₂ |
| C₂H₅CH(OH) | U | NH₂ | T | (CH₂)₂ |
| C₂H₅CH(OH) | U | N(Me)H | T | (CH₂)₂ |
| C₂H₅CH(OH) | U | N(Me)₂ | T | (CH₂)₂ |
| C₂H₅CH(OH) | U | N(Me)n-Bu | T | (CH₂)₂ |
| C₂H₅CH(OH) | U | N(nPen)H | T | (CH₂)₂ |
| C₂H₅CH(OH) | U | NHCOPh | T | (CH₂)₂ |
| C₂H₅CH(OH) | U | N(Me)CO-c-Hex | T | (CH₂)₂ |
| C₂H₅CH(OH) | U | NHCONHMe | T | (CH₂)₂ |
| C₂H₅CH(OH) | U | N(Me)CONHPh | T | (CH₂)₂ |
| C₂H₅CH(OH) | U | NHCONH-c-Hex | T | (CH₂)₂ |
| C₂H₅CH(OH) | U | NHCOBz | T | (CH₂)₂ |
| C₂H₅CH(OH) | U | J¹ | T | (CH₂)₂ |
| C₂H₅CH(OH) | U | NBzCO-n-Bu | T | (CH₂)₂ |
| C₂H₅CH(OH) | U | NBzCOO-i-Bu | T | (CH₂)₂ |
| C₂H₅CH(OH) | U | NHCO-n-Bu | T | (CH₂)₂ |
| C₂H₅CH(OH) | U | NHCOO-i-Bu | T | (CH₂)₂ |
| C₂H₅CH(OH) | U | NHCOCF₃ | T | (CH₂)₂ |
| C₂H₅CH(OH) | U | NHSO₂CF₃ | T | (CH₂)₂ |
| C₂H₅CH(OH) | U | N(Me)Ph | T | (CH₂)₂ |
| C₂H₅CH(OH) | U | NHC(=NH)NH₂ | T | (CH₂)₂ |
| C₂H₅CH(OH) | U | C(=NH)NH₂ | T | (CH₂)₂ |
| C₂H₅CH(OH) | U | CHO | T | (CH₂)₂ |
| C₂H₅CH(OH) | U | CN | T | (CH₂)₂ |
| C₂H₅CH(OH) | U | U | T | (CH₂)₂ |
| C₂H₅CH(OH) | U | COOMe | T | (CH₂)₂ |
| C₂H₅CH(OH) | U | CONH₂ | T | (CH₂)₂ |
| C₂H₅CH(OH) | U | CONHCOMe | T | (CH₂)₂ |
| C₂H₅CH(OH) | U | CH₂NH₂ | T | (CH₂)₂ |
| C₂H₅CH(OH) | U | CH₂OH | T | (CH₂)₂ |
| C₂H₅CH(OH) | U | CH₂NHCOPh | T | (CH₂)₂ |
| C₂H₅CH(OH) | U | CH₂N(nPen)COPh | T | (CH₂)₂ |
| C₂H₅CH(OH) | U | CH₂NHCONHMe | T | (CH₂)₂ |
| C₂H₅CH(OH) | U | CH₂CONHPh | T | (CH₂)₂ |
| C₂H₅CH(OH) | U | CH₂COOH | T | (CH₂)₂ |
| C₂H₅CH(OH) | U | Ph | T | (CH₂)₂ |
| C₂H₅CH(OH) | U | Bz | T | (CH₂)₂ |
| C₂H₅CH(OH) | U | CH₂CH₂Ph | T | (CH₂)₂ |
| C₂H₅CH(OH) | U | 2-thienyl | T | (CH₂)₂ |
| C₂H₅CH(OH) | U | 3-furyl | T | (CH₂)₂ |
| C₂H₅CH(OH) | U | 1-pyrrolyl | T | (CH₂)₂ |
| C₂H₅CH(OH) | U | 1-imidazolyl | T | (CH₂)₂ |
| C₂H₅CH(OH) | U | 1-pyrazolyl | T | (CH₂)₂ |
| C₂H₅CH(OH) | U | 1-pyridyl | T | (CH₂)₂ |
| C₂H₅CH(OH) | U | 1-pyrrolidinyl | T | (CH₂)₂ |
| C₂H₅CH(OH) | U | 1-piperazinyl | T | (CH₂)₂ |
| C₂H₅CH(OH) | U | 1-morpholinyl | T | (CH₂)₂ |
| C₂H₅CH(OH) | U | Ph(2-Cl) | T | (CH₂)₂ |
| C₂H₅CH(OH) | U | Ph(3-Me) | T | (CH₂)₂ |
| C₂H₅CH(OH) | U | Ph(4-OMe) | T | (CH₂)₂ |
| C₂H₅CH(OH) | U | Ph(2-NO₂) | T | (CH₂)₂ |
| C₂H₅CH(OH) | U | Ph(3-NH₂) | T | (CH₂)₂ |
| C₂H₅CH(OH) | U | Ph(4-NMe₂) | T | (CH₂)₂ |
| C₂H₅CH(OH) | U | Ph(4-J²) | T | (CH₂)₂ |
| C₂H₅CH(OH) | U | Ph(2-Cl,3-J¹) | T | (CH₂)₂ |
| C₂H₅CH(OH) | U | Ph(2-Cl,4-J¹) | T | (CH₂)₂ |
| C₂H₅CH(OH) | U | Ph(2-Cl,5-J¹) | T | (CH₂)₂ |
| C₂H₅CH(OH) | U | Ph(2-Cl,6-J¹) | T | (CH₂)₂ |
| C₂H₅CH(OH) | U | Ph(3-NHCOPh) | T | (CH₂)₂ |
| C₂H₅CH(OH) | U | Ph(4-NHCO-c-Hex) | T | (CH₂)₂ |
| C₂H₅CH(OH) | U | Ph(3-NHCONHMe) | T | (CH₂)₂ |
| C₂H₅CH(OH) | U | Ph(4-NMeCONHPh) | T | (CH₂)₂ |
| C₂H₅CH(OH) | U | Ph(3-NHCONH-c-Hex) | T | (CH₂)₂ |
| C₂H₅CH(OH) | U | Ph(4-NHCOBz) | T | (CH₂)₂ |
| C₂H₅CH(OH) | U | Ph(4-N(nPen)COPh) | T | (CH₂)₂ |
| C₂H₅CH(OH) | U | Ph(3-NHCOnBu) | T | (CH₂)₂ |
| C₂H₅CH(OH) | U | Ph(4-NHCOCF₃) | T | (CH₂)₂ |
| C₂H₅CH(OH) | U | Ph(3-NHSO₂CF₃) | T | (CH₂)₂ |
| C₂H₅CH(OH) | U | Ph(4-NMePh) | T | (CH₂)₂ |
| C₂H₅CH(OH) | U | Ph(3-NHC(=NH)NH₂) | T | (CH₂)₂ |
| C₂H₅CH(OH) | U | Ph(4-C(=NH)NH₂) | T | (CH₂)₂ |
| C₂H₅CH(OH) | U | Ph(3-COOH) | T | (CH₂)₂ |
| C₂H₅CH(OH) | U | Ph(4-CONH₂) | T | (CH₂)₂ |
| C₂H₅CH(OH) | U | Ph(3-CH₂NH₂) | T | (CH₂)₂ |
| C₂H₅CH(OH) | U | Ph(4-CH₂OH) | T | (CH₂)₂ |
| C₂H₅CH(OH) | U | Ph(4-CH₂J²) | T | (CH₂)₂ |

TABLE 1-continued

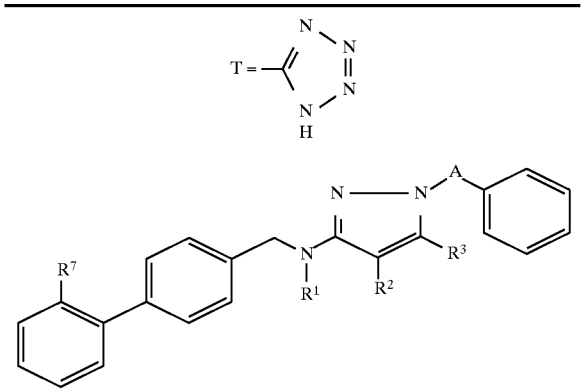

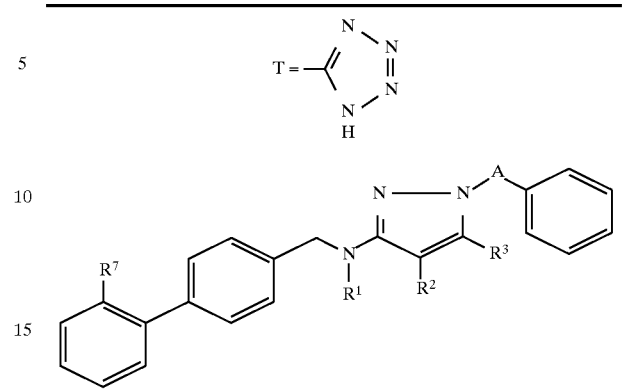

| R¹ | R² | R³ | R⁷ | A |
|---|---|---|---|---|
| C₂H₅CH(OH) | U | Ph(4-CH₂NHCONHMe) | T | (CH₂)₂ |
| C₂H₅CH(OH) | U | Ph(4-CH₂CONHPh) | T | (CH₂)₂ |
| C₂H₅CH(OH) | U | Ph(4-CH₂COOH) | T | (CH₂)₂ |
| C₂H₅CH(OH) | U | Ph(4-Ph) | T | (CH₂)₂ |
| C₂H₅CH(OH) | U | CH₂CH₂Ph(2-Cl,5-J¹) | T | (CH₂)₂ |
| C₂H₅CH(OH) | U | OH | T | (CH₂)₂ |
| C₂H₅CH(OH) | U | OMe | T | (CH₂)₂ |
| C₂H₅CH(OH) | U | OPh | T | (CH₂)₂ |
| C₂H₅CH(OH) | U | SH | T | (CH₂)₂ |
| C₂H₅CH(OH) | U | SPh | T | (CH₂)₂ |
| C₂H₅CH(OH) | U | SO₂Ph | T | (CH₂)₂ |
| C₂H₅CH(OH) | U | S-n-Bu | T | (CH₂)₂ |
| C₂H₅CH(OH) | U | 2-pyrazinyl | T | (CH₂)₂ |
| C₂H₅CH(OH) | U | 2-pyrimidinyl | T | (CH₂)₂ |
| C₂H₅CH(OH) | U | 3-pyridyl | T | (CH₂)₂ |
| C₂H₅CH(OH) | U | 4-pyridyl | T | (CH₂)₂ |
| C₂H₅CH(OH) | U | T | T | (CH₂)₂ |
| n-Pr | CH₂OH | F | T | (CH₂)₂ |
| n-Pr | CH₂OH | Cl | T | (CH₂)₂ |
| n-Pr | CH₂OH | Br | T | (CH₂)₂ |
| n-Pr | CH₂OH | I | T | (CH₂)₂ |
| n-Pr | CH₂OH | Me | T | (CH₂)₂ |
| n-Pr | CH₂OH | CF₃ | T | (CH₂)₂ |
| n-Pr | CH₂OH | Et | T | (CH₂)₂ |
| n-Pr | CH₂OH | n-Pr | T | (CH₂)₂ |
| n-Pr | CH₂OH | c-Pr | T | (CH₂)₂ |
| n-Pr | CH₂OH | NO₂ | T | (CH₂)₂ |
| n-Pr | CH₂OH | NH₂ | T | (CH₂)₂ |
| n-Pr | CH₂OH | N(Me)H | T | (CH₂)₂ |
| n-Pr | CH₂OH | N(Me)₂ | T | (CH₂)₂ |
| n-Pr | CH₂OH | N(Me)n-Bu | T | (CH₂)₂ |
| n-Pr | CH₂OH | N(nPen)H | T | (CH₂)₂ |
| n-Pr | CH₂OH | NHCOPh | T | (CH₂)₂ |
| n-Pr | CH₂OH | NHC(=NH)NH₂ | T | (CH₂)₂ |
| n-Pr | CH₂OH | C(=NH)NH₂ | T | (CH₂)₂ |
| n-Pr | CH₂OH | CHO | T | (CH₂)₂ |
| n-Pr | CH₂OH | CN | T | (CH₂)₂ |
| n-Pr | CH₂OH | U | T | (CH₂)₂ |
| n-Pr | CH₂OH | COOMe | T | (CH₂)₂ |
| n-Pr | CH₂OH | CONH₂ | T | (CH₂)₂ |
| n-Pr | CH₂OH | CONHCOMe | T | (CH₂)₂ |
| n-Pr | CH₂OH | CH₂COOH | T | (CH₂)₂ |
| n-Pr | CH₂OH | Ph | T | (CH₂)₂ |
| n-Pr | CH₂OH | Bz | T | (CH₂)₂ |
| n-Pr | CH₂OH | CH₂CH₂Ph | T | (CH₂)₂ |
| n-Pr | CH₂OH | 2-thienyl | T | (CH₂)₂ |
| n-Pr | CH₂OH | 3-furyl | T | (CH₂)₂ |
| n-Pr | CH₂OH | T | T | (CH₂)₂ |
| n-Pr | CHO | F | T | (CH₂)₂ |
| n-Pr | CHO | Cl | T | (CH₂)₂ |
| n-Pr | CHO | Br | T | (CH₂)₂ |
| n-Pr | CHO | I | T | (CH₂)₂ |
| n-Pr | CHO | Me | T | (CH₂)₂ |
| n-Pr | CHO | CF₃ | T | (CH₂)₂ |
| n-Pr | CHO | Et | T | (CH₂)₂ |
| n-Pr | CHO | n-Pr | T | (CH₂)₂ |
| n-Pr | CHO | c-Pr | T | (CH₂)₂ |
| n-Pr | CHO | NO₂ | T | (CH₂)₂ |
| n-Pr | CHO | NH₂ | T | (CH₂)₂ |
| n-Pr | CHO | N(Me)H | T | (CH₂)₂ |
| n-Pr | CHO | N(Me)₂ | T | (CH₂)₂ |
| n-Pr | CHO | N(Me)n-Bu | T | (CH₂)₂ |
| n-Pr | CHO | N(nPen)H | T | (CH₂)₂ |
| n-Pr | CHO | NHCOPh | T | (CH₂)₂ |
| n-Pr | CHO | NHC(=NH)NH₂ | T | (CH₂)₂ |
| n-Pr | CHO | C(=NH)NH₂ | T | (CH₂)₂ |
| n-Pr | CHO | CHO | T | (CH₂)₂ |
| n-Pr | CHO | CN | T | (CH₂)₂ |
| n-Pr | CHO | U | T | (CH₂)₂ |
| n-Pr | CHO | COOMe | T | (CH₂)₂ |
| n-Pr | CHO | CONH₂ | T | (CH₂)₂ |
| n-Pr | CHO | CONHCOMe | T | (CH₂)₂ |
| n-Pr | CHO | CH₂NH₂ | T | (CH₂)₂ |
| n-Pr | CHO | CH₂OH | T | (CH₂)₂ |
| n-Pr | CHO | CH₂NHCOPh | T | (CH₂)₂ |
| n-Pr | CHO | CH₂N(nPen)COPh | T | (CH₂)₂ |
| n-Pr | CHO | CH₂NHCONHMe | T | (CH₂)₂ |
| n-Pr | CHO | CH₂CONHPh | T | (CH₂)₂ |
| n-Pr | CHO | CH₂COOH | T | (CH₂)₂ |
| n-Pr | CHO | Ph | T | (CH₂)₂ |
| n-Pr | CHO | Bz | T | (CH₂)₂ |
| n-Pr | CHO | CH₂CH₂Ph | T | (CH₂)₂ |
| n-Pr | CHO | 2-thienyl | T | (CH₂)₂ |
| n-Pr | CHO | 3-furyl | T | (CH₂)₂ |
| n-Pr | CHO | T | T | (CH₂)₂ |
| n-Pr | NHCOCF₃ | F | T | (CH₂)₂ |
| n-Pr | NHCOCF₃ | Cl | T | (CH₂)₂ |
| n-Pr | NHCOCF₃ | Br | T | (CH₂)₂ |
| n-Pr | NHCOCF₃ | I | T | (CH₂)₂ |
| n-Pr | NHCOCF₃ | Me | T | (CH₂)₂ |
| n-Pr | NHCOCF₃ | CF₃ | T | (CH₂)₂ |
| n-Pr | NHCOCF₃ | Et | T | (CH₂)₂ |
| n-Pr | NHCOCF₃ | n-Pr | T | (CH₂)₂ |
| n-Pr | NHCOCF₃ | c-Pr | T | (CH₂)₂ |
| n-Pr | NHCOCF₃ | NO₂ | T | (CH₂)₂ |
| n-Pr | NHCOCF₃ | NH₂ | T | (CH₂)₂ |
| n-Pr | NHCOCF₃ | N(Me)H | T | (CH₂)₂ |
| n-Pr | NHCOCF₃ | N(Me)₂ | T | (CH₂)₂ |
| n-Pr | NHCOCF₃ | N(Me)n-Bu | T | (CH₂)₂ |
| n-Pr | NHCOCF₃ | N(nPen)H | T | (CH₂)₂ |
| n-Pr | NHCOCF₃ | NHCOPh | T | (CH₂)₂ |
| n-Pr | NHCOCF₃ | NHC(=NH)NH₂ | T | (CH₂)₂ |
| n-Pr | NHCOCF₃ | C(=NH)NH₂ | T | (CH₂)₂ |
| n-Pr | NHCOCF₃ | CHO | T | (CH₂)₂ |
| n-Pr | NHCOCF₃ | CN | T | (CH₂)₂ |
| n-Pr | NHCOCF₃ | U | T | (CH₂)₂ |
| n-Pr | NHCOCF₃ | COOMe | T | (CH₂)₂ |
| n-Pr | NHCOCF₃ | CONH₂ | T | (CH₂)₂ |
| n-Pr | NHCOCF₃ | CONHCOMe | T | (CH₂)₂ |
| n-Pr | NHCOCF₃ | CH₂COOH | T | (CH₂)₂ |
| n-Pr | NHCOCF₃ | Ph | T | (CH₂)₂ |
| n-Pr | NHCOCF₃ | Bz | T | (CH₂)₂ |
| n-Pr | NHCOCF₃ | CH₂CH₂Ph | T | (CH₂)₂ |
| n-Pr | NHCOCF₃ | 2-thienyl | T | (CH₂)₂ |
| n-Pr | NHCOCF₃ | 3-furyl | T | (CH₂)₂ |

TABLE 1-continued

T = [tetrazole structure with NH]

[Structure: biphenyl with R7 substituent, CH2-N(R1)-pyrazole(R2,R3)-N-A-phenyl]

| R¹ | R² | R³ | R⁷ | A |
|---|---|---|---|---|
| n-Pr | NH₂ | T | T | (CH₂)₂ |
| n-Pr | NH₂ | F | T | (CH₂)₂ |
| n-Pr | NH₂ | Cl | T | (CH₂)₂ |
| n-Pr | NH₂ | Br | T | (CH₂)₂ |
| n-Pr | NH₂ | I | T | (CH₂)₂ |
| n-Pr | NH₂ | Me | T | (CH₂)₂ |
| n-Pr | NH₂ | CF₃ | T | (CH₂)₂ |
| n-Pr | NH₂ | Et | T | (CH₂)₂ |
| n-Pr | NH₂ | n-Pr | T | (CH₂)₂ |
| n-Pr | NH₂ | c-Pr | T | (CH₂)₂ |
| n-Pr | NH₂ | NO₂ | T | (CH₂)₂ |
| n-Pr | NH₂ | NH₂ | T | (CH₂)₂ |
| n-Pr | NH₂ | N(Me)H | T | (CH₂)₂ |
| n-Pr | NH₂ | N(Me)₂ | T | (CH₂)₂ |
| n-Pr | NH₂ | N(Me)n-Bu | T | (CH₂)₂ |
| n-Pr | NH₂ | N(nPen)H | T | (CH₂)₂ |
| n-Pr | NH₂ | NHCOPh | T | (CH₂)₂ |
| n-Pr | NH₂ | NHC(=NH)NH₂ | T | (CH₂)₂ |
| n-Pr | NH₂ | C(=NH)NH₂ | T | (CH₂)₂ |
| n-Pr | NH₂ | CHO | T | (CH₂)₂ |
| n-Pr | NH₂ | CN | T | (CH₂)₂ |
| n-Pr | NH₂ | U | T | (CH₂)₂ |
| n-Pr | NH₂ | COOMe | T | (CH₂)₂ |
| n-Pr | NH₂ | CONH₂ | T | (CH₂)₂ |
| n-Pr | NH₂ | CONHCOMe | T | (CH₂)₂ |
| n-Pr | NH₂ | CH₂COOH | T | (CH₂)₂ |
| n-Pr | NH₂ | Ph | T | (CH₂)₂ |
| n-Pr | NH₂ | Bz | T | (CH₂)₂ |
| n-Pr | NH₂ | CH₂CH₂Ph | T | (CH₂)₂ |
| n-Pr | NH₂ | 2-thienyl | T | (CH₂)₂ |
| n-Pr | NH₂ | 3-furyl | T | (CH₂)₂ |

TABLE 2

[Structure: pyridine ring with R4, R5, R6, R7, Y, Z substituents connected via CH2-N(n-Pr)- to pyrazole(R2, R3)-N-N-CH2-phenyl]

| R³ | R⁴ | R⁵ | R⁶ | R⁷ | Y | Z |
|---|---|---|---|---|---|---|
| F | Me | H | H | T | CH | CH |
| Cl | Me | H | H | T | CH | CH |
| Br | Me | H | H | T | CH | CH |
| I | Me | H | H | T | CH | CH |
| Me | Me | H | H | T | CH | CH |
| CF₃ | Me | H | H | T | CH | CH |
| Et | Me | H | H | T | CH | CH |
| n-Pr | Me | H | H | T | CH | CH |
| c-Pr | Me | H | H | T | CH | CH |
| NO₂ | Me | H | H | T | CH | CH |
| NH₂ | Me | H | H | T | CH | CH |
| N(Me)H | Me | H | H | T | CH | CH |
| N(Me)₂ | Me | H | H | T | CH | CH |
| N(Me)n-Bu | Me | H | H | T | CH | CH |
| N(nPen)H | Me | H | H | T | CH | CH |
| NHCOPh | Me | H | H | T | CH | CH |
| NHC(=NH)NH₂ | Me | H | H | T | CH | CH |
| C(=NH)NH₂ | Me | H | H | T | CH | CH |
| CHO | Me | H | H | T | CH | CH |
| CN | Me | H | H | T | CH | CH |
| U | Me | H | H | T | CH | CH |
| COOMe | Me | H | H | T | CH | CH |
| CONH₂ | Me | H | H | T | CH | CH |
| CONHCOMe | Me | H | H | T | CH | CH |
| Ph | Me | H | H | T | CH | CH |
| Bz | Me | H | H | T | CH | CH |
| CH₂CH₂Ph | Me | H | H | T | CH | CH |
| 2-thienyl | Me | H | H | T | CH | CH |
| 3-furyl | Me | H | H | T | CH | CH |
| Ph(4-J²) | Me | H | H | T | CH | CH |
| Ph(2-Cl, 5-J¹) | Me | H | H | T | CH | CH |
| T | Me | H | H | T | CH | CH |
| F | F | H | H | T | CH | CH |
| Cl | F | H | H | T | CH | CH |
| Br | F | H | H | T | CH | CH |
| I | F | H | H | T | CH | CH |
| Me | F | H | H | T | CH | CH |
| CF₃ | F | H | H | T | CH | CH |
| Et | F | H | H | T | CH | CH |
| n-Pr | F | H | H | T | CH | CH |
| c-Pr | F | H | H | T | CH | CH |
| NO₂ | F | H | H | T | CH | CH |
| NH₂ | F | H | H | T | CH | CR |
| N(Me)H | F | H | H | T | CH | CH |
| N(Me)₂ | F | H | H | T | CH | CH |
| N(Me)n-Bu | F | H | H | T | CH | CH |
| N(nPen)H | F | H | H | T | CH | CH |
| NHCOPh | F | H | H | T | CH | CH |
| J¹ | F | H | H | T | CH | CH |
| NHC(=NH)NH₂ | F | H | H | T | CH | CH |
| C(=NH)NH₂ | F | H | H | T | CH | CH |
| CHO | F | H | H | T | CH | CH |
| CN | F | H | H | T | CH | CH |
| U | F | H | H | T | CH | CH |
| COOMe | F | H | H | T | CH | CH |
| CONH₂ | F | H | H | T | CH | CH |
| CONHCOMe | F | H | H | T | CH | CH |
| CH₂N(nPen)COPh | F | H | H | T | CH | CH |
| Ph | F | H | H | T | CH | CH |
| Bz | F | H | H | T | CH | CH |
| CH₂CH₂Ph | F | H | H | T | CH | CH |
| 2-thienyl | F | H | H | T | CH | CH |
| 3-furyl | F | H | H | T | CH | CH |

TABLE 2-continued

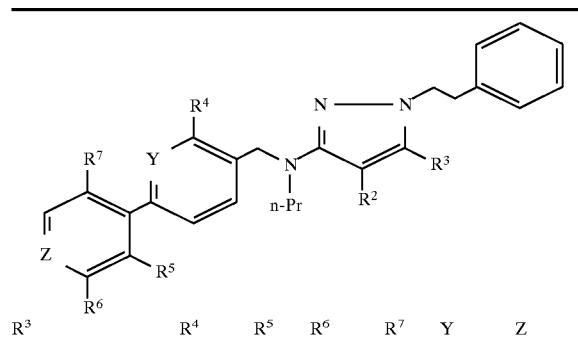

| R³ | R⁴ | R⁵ | R⁶ | R⁷ | Y | Z |
|---|---|---|---|---|---|---|
| Ph(4-J²) | F | H | H | T | CH | CH |
| Ph(2-Cl, 5-J¹) | F | H | H | T | CH | CH |
| T | F | H | H | T | CH | CH |
| F | Cl | H | H | T | CH | CH |
| Cl | Cl | H | H | T | CH | CH |
| Br | Cl | H | H | T | CH | CH |
| I | Cl | H | H | T | CH | CH |
| Me | Cl | H | H | T | CH | CH |
| CF₃ | Cl | H | H | T | CH | CH |
| Et | Cl | H | H | T | CH | CH |
| n-Pr | Cl | H | H | T | CH | CH |
| c-Pr | Cl | H | H | T | CH | CH |
| NO₂ | Cl | H | H | T | CH | CH |
| NH₂ | Cl | H | H | T | CH | CH |
| N(Me)H | Cl | H | H | T | CH | CH |
| N(Me)₂ | Cl | H | H | T | CH | CH |
| N(Me)n-Bu | Cl | H | H | T | CH | CH |
| N(nPen)H | Cl | H | H | T | CH | CH |
| NHCOPh | Cl | H | H | T | CH | CH |
| J¹ | Cl | H | H | T | CH | CH |
| NHC(=NH)NH₂ | Cl | H | H | T | CH | CH |
| C(=NH)NH₂ | Cl | H | H | T | CH | CH |
| CHO | Cl | H | H | T | CH | CH |
| CN | Cl | H | H | T | CH | CH |
| U | Cl | H | H | T | CH | CH |
| COOMe | Cl | H | H | T | CH | CH |
| CONH₂ | Cl | H | H | T | CH | CH |
| CONHCOMe | Cl | H | H | T | CH | CH |
| CH₂N(nPen)COPh | Cl | H | H | T | CH | CH |
| Ph | Cl | H | H | T | CH | CH |
| Bz | Cl | H | H | T | CH | CH |
| CH₂CH₂Ph | Cl | H | H | T | CH | CH |
| 2-thienyl | Cl | H | H | T | CH | CH |
| 3-furyl | Cl | H | H | T | CH | CH |
| Ph(4-J²) | Cl | H | H | T | CH | CH |
| Ph(2-Cl, 5-J¹) | Cl | H | H | T | CH | CH |
| T | Cl | H | H | T | CH | CH |
| F | Br | H | H | T | CH | CH |
| Cl | Br | H | H | T | CH | CH |
| Br | Br | H | H | T | CH | CH |
| I | Br | H | H | T | CH | CH |
| Me | Br | H | H | T | CH | CH |
| CF₃ | Br | H | H | T | CH | CH |
| Et | Br | H | H | T | CH | CH |
| n-Pr | Br | H | H | T | CH | CH |
| c-Pr | Br | H | H | T | CH | CH |
| NO₂ | Br | H | H | T | CH | CH |
| NH₂ | Br | H | H | T | CH | CH |
| N(Me)H | Br | H | H | T | CH | CH |
| N(Me)₂ | Br | H | H | T | CH | CH |
| N(Me)n-Bu | Br | H | H | T | CH | CH |
| N(nPen)H | Br | H | H | T | CH | CH |
| NHCOPh | Br | H | H | T | CH | CH |
| J¹ | Br | H | H | T | CH | CH |
| NHC(=NH)NH₂ | Br | H | H | T | CH | CH |
| C(=NH)NH₂ | Br | H | H | T | CH | CH |
| CHO | Br | H | H | T | CH | CH |
| CN | Br | H | H | T | CH | CH |
| U | Br | H | H | T | CH | CH |
| COOMe | Br | H | H | T | CH | CH |
| CONH₂ | Br | H | H | T | CH | CH |
| CONHCOMe | Br | H | H | T | CH | CH |
| CH₂N(nPen)COPh | Br | H | H | T | CH | CH |
| Ph | Br | H | H | T | CH | CH |
| Bz | Br | H | H | T | CH | CH |
| CH₂CH₂Ph | Br | H | H | T | CH | CH |
| 2-thienyl | Br | H | H | T | CH | CH |
| 3-furyl | Br | H | H | T | CH | CH |
| Ph(4-J²) | Br | H | H | T | CH | CH |
| Ph(2-Cl, 5-J¹) | Br | H | H | T | CH | CH |
| T | Br | H | H | T | CH | CH |
| F | OH | H | H | T | CH | CH |
| Cl | OH | H | H | T | CH | CH |
| Br | OH | H | H | T | CH | CH |
| I | OH | H | H | T | CH | CH |
| Me | OH | H | H | T | CH | CH |
| CF₃ | OH | H | H | T | CH | CH |
| Et | OH | H | H | T | CH | CH |
| n-Pr | OH | H | H | T | CH | CH |
| c-Pr | OH | H | H | T | CH | CH |
| NO₂ | OH | H | H | T | CH | CH |
| NH₂ | OH | H | H | T | CH | CH |
| N(Me)H | OH | H | H | T | CH | CH |
| N(Me)₂ | OH | H | H | T | CH | CH |
| N(Me)n-Bu | OH | H | H | T | CH | CH |
| N(nPen)H | OH | H | H | T | CH | CH |
| NHCOPh | OH | H | H | T | CH | CH |
| J¹ | OH | H | H | T | CH | CH |
| NHC(=NH)NH₂ | OH | H | H | T | CH | CH |
| C(=NH)NH₂ | OH | H | H | T | CH | CH |
| CHO | OH | H | H | T | CH | CH |
| CN | OH | H | H | T | CH | CH |
| U | OH | H | H | T | CH | CH |
| COOMe | OH | H | H | T | CH | CH |
| CH₂N(nPen)COPh | OH | H | H | T | CH | CH |
| Ph | OH | H | H | T | CH | CH |
| Bz | OH | H | H | T | CH | CH |
| CH₂CH₂Ph | OH | H | H | T | CH | CH |
| 2-thienyl | OH | H | H | T | CH | CH |
| 3-furyl | OH | H | H | T | CH | CH |
| Ph(4-J²) | OH | H | H | T | CH | CH |
| Ph(2-Cl, 5-J¹) | OH | H | H | T | CH | CH |
| T | OH | H | H | T | CH | CH |
| F | H | H | H | T | CMe | CH |
| Cl | H | H | H | T | CMe | CH |
| Br | H | H | H | T | CMe | CH |
| I | H | H | H | T | CMe | CH |
| Me | H | H | H | T | CMe | CH |
| CF₃ | H | H | H | T | CMe | CH |
| Et | H | H | H | T | CMe | CH |
| n-Pr | H | H | H | T | CMe | CH |
| c-Pr | H | H | H | T | CMe | CH |
| NO₂ | H | H | H | T | CMe | CH |
| NH₂ | H | H | H | T | CMe | CH |
| N(Me)H | H | H | H | T | CMe | CH |
| N(Me)₂ | H | H | H | T | CMe | CH |
| N(Me)n-Bu | H | H | H | T | CMe | CH |
| N(nPen)H | H | H | H | T | CMe | CH |
| NHCOPh | H | H | H | T | CMe | CH |
| J¹ | H | H | H | T | CMe | CH |
| NHC(=NH)NH₂ | H | H | H | T | CMe | CH |
| C(=NH)NH₂ | H | H | H | T | CMe | CH |
| CHO | H | H | H | T | CMe | CH |
| CN | H | H | H | T | CMe | CH |
| U | H | H | H | T | CMe | CH |
| COOMe | H | H | H | T | CMe | CH |

TABLE 2-continued

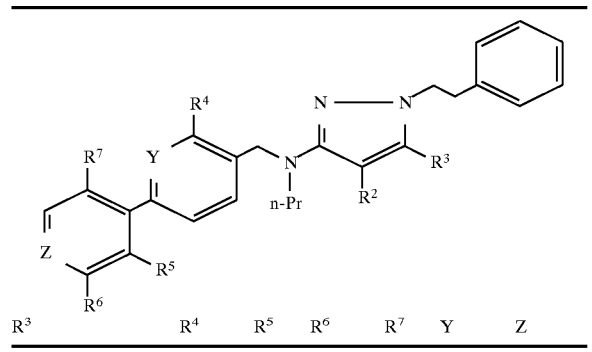

| R³ | R⁴ | R⁵ | R⁶ | R⁷ | Y | Z |
|---|---|---|---|---|---|---|
| CONH₂ | H | H | H | T | CMe | CH |
| CONHCOMe | H | H | H | T | CMe | CH |
| CH₂N(nPen)COPh | H | H | H | T | CMe | CH |
| Ph | H | H | H | T | CMe | CH |
| Bz | H | H | H | T | CMe | CH |
| CH₂CH₂Ph | H | H | H | T | CMe | CH |
| 2-thienyl | H | H | H | T | CMe | CH |
| 3-furyl | H | H | H | T | CMe | CH |
| Ph(4-J²) | H | H | H | T | CMe | CH |
| Ph(2-Cl, 5-J¹) | H | H | H | T | CMe | CH |
| T | H | H | H | T | CMe | CH |
| F | H | H | H | T | CF | CH |
| Cl | H | H | H | T | CF | CH |
| Br | H | H | H | T | CF | CH |
| I | H | H | H | T | CF | CH |
| Me | H | H | H | T | CF | CH |
| CF₃ | H | H | H | T | CF | CH |
| Et | H | H | H | T | CF | CH |
| n-Pr | H | H | H | T | CF | CH |
| c-Pr | H | H | H | T | CF | CH |
| NO₂ | H | H | H | T | CF | CH |
| NH₂ | H | H | H | T | CF | CH |
| N(Me)H | H | H | H | T | CF | CH |
| N(Me)₂ | H | H | H | T | CF | CH |
| N(Me)n-Bu | H | H | H | T | CF | CH |
| N(nPen)H | H | H | H | T | CF | CH |
| NHCOPh | H | H | H | T | CF | CH |
| J¹ | H | H | H | T | CF | CH |
| NHC(=NH)NH₂ | H | H | H | T | CF | CH |
| C(=NH)NH₂ | H | H | H | T | CF | CH |
| CHO | H | H | H | T | CF | CH |
| CN | H | H | H | T | CF | CH |
| U | H | H | H | T | CF | CH |
| COOMe | H | H | H | T | CF | CH |
| CONH₂ | H | H | H | T | CF | CH |
| CONHCOMe | H | H | H | T | CF | CH |
| CH₂N(nPen)COPh | H | H | H | T | CF | CH |
| Ph | H | H | H | T | CF | CH |
| Bz | H | H | H | T | CF | CH |
| CH₂CH₂Ph | H | H | H | T | CF | CH |
| 2-thienyl | H | H | H | T | CF | CH |
| 3-furyl | H | H | H | T | CF | CH |
| Ph(4-J²) | H | H | H | T | CF | CH |
| Ph(2-Cl, 5-J¹) | H | H | H | T | CF | CH |
| T | H | H | H | T | CF | CH |
| F | H | H | H | T | CCl | CH |
| Cl | H | H | H | T | CCl | CH |
| Br | H | H | H | T | CCl | CH |
| I | H | H | H | T | CCl | CH |
| Me | H | H | H | T | CCl | CH |
| CF₃ | H | H | H | T | CCl | CH |
| Et | H | H | H | T | CCl | CH |
| n-Pr | H | H | H | T | CCl | CH |
| c-Pr | H | H | H | T | CCl | CH |
| NO₂ | H | H | H | T | CCl | CH |
| NH₂ | H | H | H | T | CCl | CH |
| N(Me)H | H | H | H | T | CCl | CH |
| N(Me)₂ | H | H | H | T | CCl | CH |
| N(Me)n-Bu | H | H | H | T | CCl | CH |
| N(nPen)H | H | H | H | T | CCl | CH |
| NHCOPh | H | H | H | T | CCl | CH |
| J¹ | H | H | H | T | CCl | CH |
| NHC(=NH)NH₂ | H | H | H | T | CCl | CH |
| C(=NH)NH₂ | H | H | H | T | CCl | CH |
| CHO | H | H | H | T | CCl | CH |
| CN | H | H | H | T | CCl | CH |
| U | H | H | H | T | CCl | CH |
| COOMe | H | H | H | T | CCl | CH |
| CONH₂ | H | H | H | T | CCl | CH |
| CONHCOMe | H | H | H | T | CCl | CH |
| CH₂N(nPen)COPh | H | H | H | T | CCl | CH |
| Ph | H | H | H | T | CCl | CH |
| Bz | H | H | H | T | CCl | CH |
| CH₂CH₂Ph | H | H | H | T | CCl | CH |
| 2-thienyl | H | H | H | T | CCl | CH |
| 3-furyl | H | H | H | T | CCl | CH |
| Ph(4-J²) | H | H | H | T | CCl | CH |
| Ph(2-Cl, 5-J¹) | H | H | H | T | CCl | CH |
| T | H | H | H | T | CCl | CH |
| F | H | H | H | T | CBr | CH |
| Cl | H | H | H | T | CBr | CH |
| Br | H | H | H | T | CBr | CH |
| I | H | H | H | T | CBr | CH |
| Me | H | H | H | T | CBr | CH |
| CF₃ | H | H | H | T | CBr | CH |
| Et | H | H | H | T | CBr | CH |
| n-Pr | H | H | H | T | CBr | CH |
| c-Pr | H | H | H | T | CBr | CH |
| NO₂ | H | H | H | T | CBr | CH |
| NH₂ | H | H | H | T | CBr | CH |
| N(Me)H | H | H | H | T | CBr | CH |
| N(Me)₂ | H | H | H | T | CBr | CH |
| N(Me)n-Bu | H | H | H | T | CBr | CH |
| N(nPen)H | H | H | H | T | CBr | CH |
| NHCOPh | H | H | H | T | CBr | CH |
| J¹ | H | H | H | T | CBr | CH |
| NHC(=NH)NH₂ | H | H | H | T | CBr | CH |
| C(=NH)NH₂ | H | H | H | T | CBr | CH |
| CHO | H | H | H | T | CBr | CH |
| CN | H | H | H | T | CBr | CH |
| U | H | H | H | T | CBr | CH |
| COOMe | H | H | H | T | CBr | CH |
| CONH₂ | H | H | H | T | CBr | CH |
| CONHCOMe | H | H | H | T | CBr | CH |
| CH₂N(nPen)COPh | H | H | H | T | CBr | CH |
| Ph | H | H | H | T | CBr | CH |
| Bz | H | H | H | T | CBr | CH |
| CH₂CH₂Ph | H | H | H | T | CBr | CH |
| 2-thienyl | H | H | H | T | CBr | CH |
| 3-furyl | H | H | H | T | CBr | CH |
| Ph(4-J²) | H | H | H | T | CBr | CH |
| Ph(2-Cl, 5-J¹) | H | H | H | T | CBr | CH |
| T | H | H | H | T | CBr | CH |
| F | H | H | H | T | COH | CH |
| Cl | H | H | H | T | COH | CH |
| Br | H | H | H | T | COH | CH |
| I | H | H | H | T | COH | CH |
| Me | H | H | H | T | COH | CH |
| CF₃ | H | H | H | T | COH | CH |
| Et | H | H | H | T | COH | CH |
| n-Pr | H | H | H | T | COH | CH |
| c-Pr | H | H | H | T | COH | CH |
| NO₂ | H | H | H | T | COH | CH |
| NH₂ | H | H | H | T | COH | CH |
| N(Me)H | H | H | H | T | COH | CH |
| N(Me)₂ | H | H | H | T | COH | CH |

TABLE 2-continued

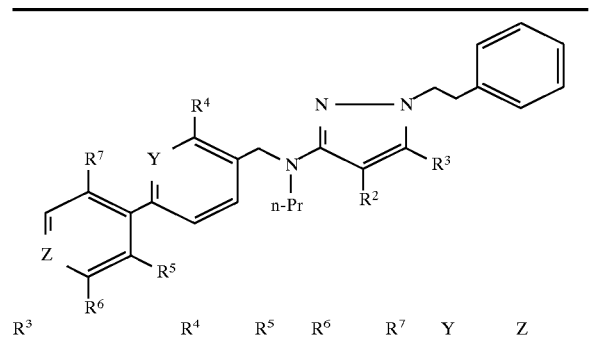

| R³ | R⁴ | R⁵ | R⁶ | R⁷ | Y | Z |
|---|---|---|---|---|---|---|
| N(Me)n-Bu | H | H | H | T | COH | CH |
| N(nPen)H | H | H | H | T | COH | CH |
| NHCOPh | H | H | H | T | COH | CH |
| J¹ | H | H | H | T | COH | CH |
| NHC(=NH)NH₂ | H | H | H | T | COH | CH |
| C(=NH)NH₂ | H | H | H | T | COH | CH |
| CHO | H | H | H | T | COH | CH |
| CN | H | H | H | T | COH | CH |
| U | H | H | H | T | COH | CH |
| COOMe | H | H | H | T | COH | CH |
| CONH₂ | H | H | H | T | COH | CH |
| CONHCOMe | H | H | H | T | COH | CH |
| Ph | H | H | H | T | COH | CH |
| Bz | H | H | H | T | COH | CH |
| CH₂CH₂Ph | H | H | H | T | COH | CH |
| 2-thienyl | H | H | H | T | COH | CH |
| Ph(4-J²) | H | H | H | T | COH | CH |
| Ph(2-Cl, 5-J¹) | H | H | H | T | COH | CH |
| T | H | H | H | T | COH | CH |
| F | H | H | H | T | N | CH |
| Cl | H | H | H | T | N | CH |
| Br | H | H | H | T | N | CH |
| I | H | H | H | T | N | CH |
| Me | H | H | H | T | N | CH |
| CF₃ | H | H | H | T | N | CH |
| Et | H | H | H | T | N | CH |
| n-Pr | H | H | H | T | N | CH |
| c-Pr | H | H | H | T | N | CH |
| NO₂ | H | H | H | T | N | CH |
| NH₂ | H | H | H | T | N | CH |
| N(Me)H | H | H | H | T | N | CH |
| N(Me)₂ | H | H | H | T | N | CH |
| N(Me)n-Bu | H | H | H | T | N | CH |
| N(nPen)H | H | H | H | T | N | CH |
| NHCOPh | H | H | H | T | N | CH |
| J¹ | H | H | H | T | N | CH |
| NHC(=NH)NH₂ | H | H | H | T | N | CH |
| C(=NH)NH₂ | H | H | H | T | N | CH |
| CHO | H | H | H | T | N | CH |
| CN | H | H | H | T | N | CH |
| U | H | H | H | T | N | CH |
| COOMe | H | H | H | T | N | CH |
| CONH₂ | H | H | H | T | N | CH |
| CONHCOMe | H | H | H | T | N | CH |
| CH₂N(nPen)COPh | H | H | H | T | N | CH |
| Ph | H | H | H | T | N | CH |
| Bz | H | H | H | T | N | CH |
| CH₂CH₂Ph | H | H | H | T | N | CH |
| 2-thienyl | H | H | H | T | N | CH |
| 3-furyl | H | H | H | T | N | CH |
| Ph(4-J²) | H | H | H | T | N | CH |
| Ph(2-Cl, 5-J¹) | H | H | H | T | N | CH |
| T | H | H | H | T | N | CH |
| F | H | Me | H | T | CH | CH |
| Cl | H | Me | H | T | CH | CH |
| Br | H | Me | H | T | CH | CH |
| I | H | Me | H | T | CH | CH |
| Me | H | Me | H | T | CH | CH |
| CF₃ | H | Me | H | T | CH | CH |
| Et | H | Me | H | T | CH | CH |
| n-Pr | H | Me | H | T | CH | CH |
| c-Pr | H | Me | H | T | CH | CH |
| NO₂ | H | Me | H | T | CH | CH |
| NH₂ | H | Me | H | T | CH | CH |
| N(Me)H | H | Me | H | T | CH | CH |
| N(Me)₂ | H | Me | H | T | CH | CH |
| N(Me)n-Bu | H | Me | H | T | CH | CH |
| N(nPen)H | H | Me | H | T | CH | CH |
| NHCOPh | H | Me | H | T | CH | CH |
| J¹ | H | Me | H | T | CH | CH |
| NHC(=NH)NH₂ | H | Me | H | T | CH | CH |
| C(=NH)NH₂ | H | Me | H | T | CH | CH |
| CHO | H | Me | H | T | CH | CH |
| CN | H | Me | H | T | CH | CH |
| U | H | Me | H | T | CH | CH |
| COOMe | H | Me | H | T | CH | CH |
| CONH₂ | H | Me | H | T | CH | CH |
| CONHCOMe | H | Me | H | T | CH | CH |
| CH₂N(nPen)COPh | H | Me | H | T | CH | CH |
| Ph | H | Me | H | T | CH | CH |
| Bz | H | Me | H | T | CH | CH |
| CH₂CH₂Ph | H | Me | H | T | CH | CH |
| 2-thienyl | H | Me | H | T | CH | CH |
| 3-furyl | H | Me | H | T | CH | CH |
| Ph(4-J²) | H | Me | H | T | CH | CH |
| Ph(2-Cl, 5-J¹) | H | Me | H | T | CH | CH |
| T | H | Me | H | T | CH | CH |
| F | H | F | H | T | CH | CH |
| Cl | H | F | H | T | CH | CH |
| Br | H | F | H | T | CH | CH |
| I | H | F | H | T | CH | CH |
| Me | H | F | H | T | CH | CH |
| CF₃ | H | F | H | T | CH | CH |
| Et | H | F | H | T | CH | CH |
| n-Pr | H | F | H | T | CH | CH |
| c-Pr | H | F | H | T | CH | CH |
| NO₂ | H | F | H | T | CH | CH |
| NH₂ | H | F | H | T | CH | CH |
| N(Me)H | H | F | H | T | CH | CH |
| N(Me)₂ | H | F | H | T | CH | CH |
| N(Me)n-Bu | H | F | H | T | CH | CH |
| N(nPen)H | H | F | H | T | CH | CH |
| NHCOPh | H | F | H | T | CH | CH |
| J¹ | H | F | H | T | CH | CH |
| NHC(=NH)NH₂ | H | F | H | T | CH | CH |
| C(=NH)NH₂ | H | F | H | T | CH | CH |
| CHO | H | F | H | T | CH | CH |
| CN | H | F | H | T | CH | CH |
| U | H | F | H | T | CH | CH |
| COOMe | H | F | H | T | CH | CH |
| CONH₂ | H | F | H | T | CH | CH |
| CONHCOMe | H | F | H | T | CH | CH |
| CH₂N(nPen)COPh | H | F | H | T | CH | CH |
| Ph | H | F | H | T | CH | CH |
| Bz | H | F | H | T | CH | CH |
| CH₂CH₂Ph | H | F | H | T | CH | CH |
| 2-thienyl | H | F | H | T | CH | CH |
| 3-furyl | H | F | H | T | CH | CH |
| Ph(4-J²) | H | F | H | T | CH | CH |
| Ph(2-Cl, 5-J¹) | H | F | H | T | CH | CH |
| T | H | F | H | T | CH | CH |
| F | H | Cl | H | T | CH | CH |
| Cl | H | Cl | H | T | CH | CH |
| Br | H | Cl | H | T | CH | CH |
| I | H | Cl | H | T | CH | CH |
| Me | H | Cl | H | T | CH | CH |

TABLE 2-continued

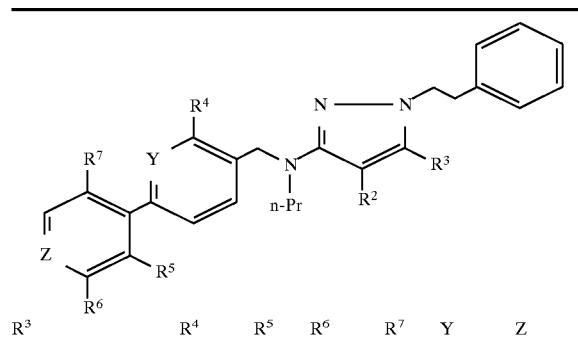

| R³ | R⁴ | R⁵ | R⁶ | R⁷ | Y | Z |
|---|---|---|---|---|---|---|
| CF₃ | H | Cl | H | T | CH | CH |
| Et | H | Cl | H | T | CH | CH |
| n-Pr | H | Cl | H | T | CH | CH |
| c-Pr | H | Cl | H | T | CH | CH |
| NO₂ | H | Cl | H | T | CH | CH |
| NH₂ | H | Cl | H | T | CH | CH |
| N(Me)H | H | Cl | H | T | CH | CH |
| N(Me)₂ | H | Cl | H | T | CH | CH |
| N(Me)n-Bu | H | Cl | H | T | CH | CH |
| N(nPen)H | H | Cl | H | T | CH | CH |
| NHCOPh | H | Cl | H | T | CH | CH |
| J¹ | H | Cl | H | T | CH | CH |
| NHC(=NH)NH₂ | H | Cl | H | T | CH | CH |
| C(=NH)NH₂ | H | Cl | H | T | CH | CH |
| CHO | H | Cl | H | T | CH | CH |
| CN | H | Cl | H | T | CH | CH |
| U | H | Cl | H | T | CH | CH |
| COOMe | H | Cl | H | T | CH | CH |
| CONH₂ | H | Cl | H | T | CH | CH |
| CONHCOMe | H | Cl | H | T | CH | CH |
| CH₂N(nPen)COPh | H | Cl | H | T | CH | CH |
| Ph | H | Cl | H | T | CH | CH |
| Bz | H | Cl | H | T | CH | CH |
| CH₂CH₂Ph | H | Cl | H | T | CH | CH |
| 2-thienyl | H | Cl | H | T | CH | CH |
| 3-furyl | H | Cl | H | T | CH | CH |
| Ph(4-J²) | H | Cl | H | T | CH | CH |
| Ph(2-Cl, 5-J¹) | H | Cl | H | T | CH | CH |
| T | H | Cl | H | T | CH | CH |
| F | H | Br | H | T | CH | CH |
| Cl | H | Br | H | T | CH | CH |
| Br | H | Br | H | T | CH | CH |
| I | H | Br | H | T | CH | CH |
| Me | H | Br | H | T | CH | CH |
| CF₃ | H | Br | H | T | CH | CH |
| Et | H | Br | H | T | CH | CH |
| n-Pr | H | Br | H | T | CH | CH |
| c-Pr | H | Br | H | T | CH | CH |
| NO₂ | H | Br | H | T | CH | CH |
| NH₂ | H | Br | H | T | CH | CH |
| N(Me)H | H | Br | H | T | CH | CH |
| N(Me)₂ | H | Br | H | T | CH | CH |
| N(Me)n-Bu | H | Br | H | T | CH | CH |
| N(nPen)H | H | Br | H | T | CH | CH |
| NHCOPh | H | Br | H | T | CH | CH |
| J¹ | H | Br | H | T | CH | CH |
| NHC(=NH)NH₂ | H | Br | H | T | CH | CH |
| C(=NH)NH₂ | H | Br | H | T | CH | CH |
| CHO | H | Br | H | T | CH | CH |
| CN | H | Br | H | T | CH | CH |
| U | H | Br | H | T | CH | CH |
| COOMe | H | Br | H | T | CH | CH |
| CONH₂ | H | Br | H | T | CH | CH |
| CONHCOMe | H | Br | H | T | CH | CH |
| CH₂N(nPen)COPh | H | Br | H | T | CH | CH |
| Ph | H | Br | H | T | CH | CH |
| Bz | H | Br | H | T | CH | CH |
| CH₂CH₂Ph | H | Br | H | T | CH | CH |
| 2-thienyl | H | Br | H | T | CH | CH |
| 3-furyl | H | Br | H | T | CH | CH |
| Ph(4-J²) | H | Br | H | T | CH | CH |
| Ph(2-Cl, 5-J¹) | H | Br | H | T | CH | CH |
| T | H | Br | H | T | CH | CH |
| F | H | OH | H | T | CH | CH |
| Cl | H | OH | H | T | CH | CH |
| Br | H | OH | H | T | CH | CH |
| I | H | OH | H | T | CH | CH |
| Me | H | OH | H | T | CH | CH |
| CF₃ | H | OH | H | T | CH | CH |
| Et | H | OH | H | T | CH | CH |
| n-Pr | H | OH | H | T | CH | CH |
| c-Pr | H | OH | H | T | CH | CH |
| NO₂ | H | OH | H | T | CH | CH |
| NH₂ | H | OH | H | T | CH | CH |
| N(Me)H | H | OH | H | T | CH | CH |
| N(Me)₂ | H | OH | H | T | CH | CH |
| N(Me)n-Bu | H | OH | H | T | CH | CH |
| N(nPen)H | H | OH | H | T | CH | CH |
| NHCOPh | H | OH | H | T | CH | CH |
| J¹ | H | OH | H | T | CH | CH |
| NHC(=NH)NH₂ | H | OH | H | T | CH | CH |
| C(=NH)NH₂ | H | OH | H | T | CH | CH |
| CHO | H | OH | H | T | CH | CH |
| CN | H | OH | H | T | CH | CH |
| U | H | OH | H | T | CH | CH |
| COOMe | H | OH | H | T | CH | CH |
| CONH₂ | H | OH | H | T | CH | CH |
| CONHCOMe | H | OH | H | T | CH | CH |
| CH₂N(nPen)COPh | H | OH | H | T | CH | CH |
| Ph | H | OH | H | T | CH | CH |
| Bz | H | OH | H | T | CH | CH |
| CH₂CH₂Ph | H | OH | H | T | CH | CH |
| 2-thienyl | H | OH | H | T | CH | CH |
| 3-furyl | H | OH | H | T | CH | CH |
| 1-pyrrolyl | H | OH | H | T | CH | CH |
| Ph(4-J²) | H | OH | H | T | CH | CH |
| Ph(2-Cl, 5-J¹) | H | OH | H | T | CH | CH |
| T | H | OH | H | T | CH | CH |
| F | H | H | Me | T | CH | CH |
| Cl | H | H | Me | T | CH | CH |
| Br | H | H | Me | T | CH | CH |
| I | H | H | Me | T | CH | CH |
| Me | H | H | Me | T | CH | CH |
| CF₃ | H | H | Me | T | CH | CH |
| Et | H | H | Me | T | CH | CH |
| n-Pr | H | H | Me | T | CH | CH |
| c-Pr | H | H | Me | T | CH | CH |
| NO₂ | H | H | Me | T | CH | CH |
| NH₂ | H | H | Me | T | CH | CH |
| N(Me)H | H | H | Me | T | CH | CH |
| N(Me)₂ | H | H | Me | T | CH | CH |
| N(Me)n-Bu | H | H | Me | T | CH | CH |
| N(nPen)H | H | H | Me | T | CH | CH |
| NHCOPh | H | H | Me | T | CH | CH |
| J¹ | H | H | Me | T | CH | CH |
| NHC(=NH)NH₂ | H | H | Me | T | CH | CH |
| C(=NH)NH₂ | H | H | Me | T | CH | CH |
| CHO | H | H | Me | T | CH | CH |
| CN | H | H | Me | T | CH | CH |
| U | H | H | Me | T | CH | CH |
| COOMe | H | H | Me | T | CH | CH |
| CONH₂ | H | H | Me | T | CH | CH |
| CONHCOMe | H | H | Me | T | CH | CH |
| CH₂N(nPen)COPh | H | H | Me | T | CH | CH |
| Ph | H | H | Me | T | CH | CH |
| Bz | H | H | Me | T | CH | CH |

TABLE 2-continued

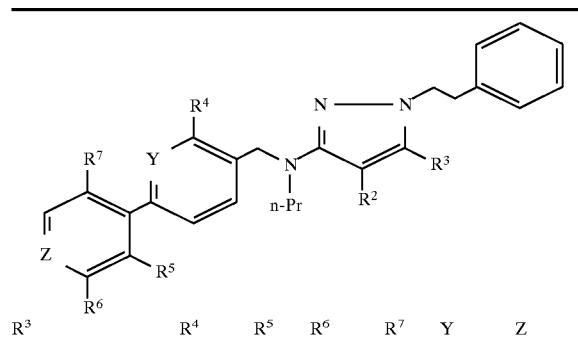

| R³ | R⁴ | R⁵ | R⁶ | R⁷ | Y | Z |
|---|---|---|---|---|---|---|
| CH₂CH₂Ph | H | H | Me | T | CH | CH |
| 2-thienyl | H | H | Me | T | CH | CH |
| 3-furyl | H | H | Me | T | CH | CH |
| Ph(4-J²) | H | H | Me | T | CH | CH |
| Ph(2-Cl, 5-J¹) | H | H | Me | T | CH | CH |
| T | H | H | Me | T | CH | CH |
| F | H | H | F | T | CH | CH |
| Cl | H | H | F | T | CH | CH |
| Br | H | H | F | T | CH | CH |
| I | H | H | F | T | CH | CH |
| Me | H | H | F | T | CH | CH |
| CF₃ | H | H | F | T | CH | CH |
| Et | H | H | F | T | CH | CH |
| n-Pr | H | H | F | T | CH | CH |
| c-Pr | H | H | F | T | CH | CH |
| NO₂ | H | H | F | T | CH | CH |
| NH₂ | H | H | F | T | CH | CH |
| N(Me)H | H | H | F | T | CH | CH |
| N(Me)₂ | H | H | F | T | CH | CH |
| N(Me)n-Bu | H | H | F | T | CH | CH |
| N(nPen)H | H | H | F | T | CH | CH |
| NHCOPh | H | H | F | T | CH | CH |
| J¹ | H | H | F | T | CH | CH |
| NHC(=NH)NH₂ | H | H | F | T | CH | CH |
| C(=NH)NH₂ | H | H | F | T | CH | CH |
| CHO | H | H | F | T | CH | CH |
| CN | H | H | F | T | CH | CH |
| U | H | H | F | T | CH | CH |
| COOMe | H | H | F | T | CH | CH |
| CONH₂ | H | H | F | T | CH | CH |
| CONHCOMe | H | H | F | T | CH | CH |
| CH₂N(nPen)COPh | H | H | F | T | CH | CH |
| Ph | H | H | F | T | CH | CH |
| Bz | H | H | F | T | CH | CH |
| CH₂CH₂Ph | H | H | F | T | CH | CH |
| 2-thienyl | H | H | F | T | CH | CH |
| 3-furyl | H | H | F | T | CH | CH |
| Ph(4-J²) | H | H | F | T | CH | CH |
| Ph(2-Cl, 5-J¹) | H | H | F | T | CH | CH |
| T | H | H | F | T | CH | CH |
| F | H | H | Cl | T | CH | CH |
| Cl | H | H | Cl | T | CH | CH |
| Br | H | H | Cl | T | CH | CH |
| I | H | H | Cl | T | CH | CH |
| Me | H | H | Cl | T | CH | CH |
| CF₃ | H | H | Cl | T | CH | CH |
| Et | H | H | Cl | T | CH | CH |
| n-Pr | H | H | Cl | T | CH | CH |
| c-Pr | H | H | Cl | T | CH | CH |
| NO₂ | H | H | Cl | T | CH | CH |
| NH₂ | H | H | Cl | T | CH | CH |
| N(Me)H | H | H | Cl | T | CH | CH |
| N(Me)₂ | H | H | Cl | T | CH | CH |
| N(Me)n-Bu | H | H | Cl | T | CH | CH |
| N(nPen)H | H | H | Cl | T | CH | CH |
| NHCOPh | H | H | Cl | T | CH | CH |
| J¹ | H | H | Cl | T | CH | CH |
| NHC(=NH)NH₂ | H | H | Cl | T | CH | CH |
| C(=NH)NH₂ | H | H | Cl | T | CH | CH |
| CHO | H | H | Cl | T | CH | CH |
| CN | H | H | Cl | T | CH | CH |
| U | H | H | Cl | T | CH | CH |
| COOMe | H | H | Cl | T | CH | CH |
| CONH₂ | H | H | Cl | T | CH | CH |
| CONHCOMe | H | H | Cl | T | CH | CH |
| CH₂N(nPen)COPh | H | H | Cl | T | CH | CH |
| Ph | H | H | Cl | T | CH | CH |
| Bz | H | H | Cl | T | CH | CH |
| CH₂CH₂Ph | H | H | Cl | T | CH | CH |
| 2-thienyl | H | H | Cl | T | CH | CH |
| 3-furyl | H | H | Cl | T | CH | CH |
| Ph(4-J²) | H | H | Cl | T | CH | CH |
| Ph(2-Cl, 5-J¹) | H | H | Cl | T | CH | CH |
| T | H | H | Cl | T | CH | CH |
| F | H | H | Br | T | CH | CH |
| Cl | H | H | Br | T | CH | CH |
| Br | H | H | Br | T | CH | CH |
| I | H | H | Br | T | CH | CH |
| Me | H | H | Br | T | CH | CH |
| CF₃ | H | H | Br | T | CH | CH |
| Et | H | H | Br | T | CH | CH |
| n-Pr | H | H | Br | T | CH | CH |
| c-Pr | H | H | Br | T | CH | CH |
| NO₂ | H | H | Br | T | CH | CH |
| NH₂ | H | H | Br | T | CH | CH |
| N(Me)H | H | H | Br | T | CH | CH |
| N(Me)₂ | H | H | Br | T | CH | CH |
| N(Me)n-Bu | H | H | Br | T | CH | CH |
| N(nPen)H | H | H | Br | T | CH | CH |
| NHCOPh | H | H | Br | T | CH | CH |
| J¹ | H | H | Br | T | CH | CH |
| NHC(=NH)NH₂ | H | H | Br | T | CH | CH |
| C(=NH)NH₂ | H | H | Br | T | CH | CH |
| CHO | H | H | Br | T | CH | CH |
| CN | H | H | Br | T | CH | CH |
| U | H | H | Br | T | CH | CH |
| COOMe | H | H | Br | T | CH | CH |
| CONH₂ | H | H | Br | T | CH | CH |
| CONHCOMe | H | H | Br | T | CH | CH |
| CH₂N(nPen)COPh | H | H | Br | T | CH | CH |
| Ph | H | H | Br | T | CH | CH |
| Bz | H | H | Br | T | CH | CH |
| CH₂CH₂Ph | H | H | Br | T | CH | CH |
| 2-thienyl | H | H | Br | T | CH | CH |
| 3-furyl | H | H | Br | T | CH | CH |
| Ph(4-J²) | H | H | Br | T | CH | CH |
| Ph(2-Cl, 5-J¹) | H | H | Br | T | CH | CH |
| T | H | H | Br | T | CH | CH |
| F | H | H | OH | T | CH | CH |
| Cl | H | H | OH | T | CH | CH |
| Br | H | H | OH | T | CH | CH |
| I | H | H | OH | T | CH | CH |
| Me | H | H | OH | T | CH | CH |
| CF₃ | H | H | OH | T | CH | CH |
| Et | H | H | OH | T | CH | CH |
| n-Pr | H | H | OH | T | CH | CH |
| c-Pr | H | H | OH | T | CH | CH |
| NO₂ | H | H | OH | T | CH | CH |
| NH₂ | H | H | OH | T | CH | CH |
| N(Me)H | H | H | OH | T | CH | CH |
| N(Me)₂ | H | H | OH | T | CH | CH |
| N(Me)n-Bu | H | H | OH | T | CH | CH |
| N(nPen)H | H | H | OH | T | CH | CH |
| NHCOPh | H | H | OH | T | CH | CH |
| J¹ | H | H | OH | T | CH | CH |
| NHC(=NH)NH₂ | H | H | OH | T | CH | CH |

TABLE 2-continued

| R³ | R⁴ | R⁵ | R⁶ | R⁷ | Y | Z |
|---|---|---|---|---|---|---|
| C(=NH)NH₂ | H | H | OH | T | CH | CH |
| CHO | H | H | OH | T | CH | CH |
| CN | H | H | OH | T | CH | CH |
| U | H | H | OH | T | CH | CH |
| COOMe | H | H | OH | T | CH | CH |
| CONH₂ | H | H | OH | T | CH | CH |
| CONHCOMe | H | H | OH | T | CH | CH |
| CH₂N(nPen)COPh | H | H | OH | T | CH | CH |
| Ph | H | H | OH | T | CH | CH |
| Bz | H | H | OH | T | CH | CH |
| CH₂CH₂Ph | H | H | OH | T | CH | CH |
| 2-thienyl | H | H | OH | T | CH | CH |
| 3-furyl | H | H | OH | T | CH | CH |
| Ph(4-J²) | H | H | OH | T | CH | CH |
| Ph(2-Cl, 5-J¹) | H | H | OH | T | CH | CH |
| T | H | H | OH | T | CH | CH |
| F | H | H | H | T | CH | CMe |
| Cl | H | H | H | T | CH | CMe |
| Br | H | H | H | T | CH | CMe |
| I | H | H | H | T | CH | CMe |
| Me | H | H | H | T | CH | CMe |
| CF₃ | H | H | H | T | CH | CMe |
| Et | H | H | H | T | CH | CMe |
| n-Pr | H | H | H | T | CH | CMe |
| c-Pr | H | H | H | T | CH | CMe |
| NO₂ | H | H | H | T | CH | CMe |
| NH₂ | H | H | H | T | CH | CMe |
| N(Me)H | H | H | H | T | CH | CMe |
| N(Me)₂ | H | H | H | T | CH | CMe |
| N(Me)n-Bu | H | H | H | T | CH | CMe |
| N(nPen)H | H | H | H | T | CH | CMe |
| NHCOPh | H | H | H | T | CH | CMe |
| J¹ | H | H | H | T | CH | CMe |
| NHC(=NH)NH₂ | H | H | H | T | CH | CMe |
| C(=NH)NH₂ | H | H | H | T | CH | CMe |
| CHO | H | H | H | T | CH | CMe |
| CN | H | H | H | T | CH | CMe |
| U | H | H | H | T | CH | CMe |
| COOMe | H | H | H | T | CH | CMe |
| CONH₂ | H | H | H | T | CH | CMe |
| CONHCOMe | H | H | H | T | CH | CMe |
| CH₂N(nPen)COPh | H | H | H | T | CH | CMe |
| Ph | H | H | H | T | CH | CMe |
| Bz | H | H | H | T | CH | CMe |
| CH₂CH₂Ph | H | H | H | T | CH | CMe |
| 2-thienyl | H | H | H | T | CH | CMe |
| 3-furyl | H | H | H | T | CH | CMe |
| Ph(4-J²) | H | H | H | T | CH | CMe |
| Ph(2-Cl, 5-J¹) | H | H | H | T | CH | CMe |
| T | H | H | H | T | CH | CMe |
| F | H | H | H | T | CH | CF |
| Cl | H | H | H | T | CH | CF |
| Br | H | H | H | T | CH | CF |
| I | H | H | H | T | CH | CF |
| Me | H | H | H | T | CH | CF |
| CF₃ | H | H | H | T | CH | CF |
| Et | H | H | H | T | CH | CF |
| n-Pr | H | H | H | T | CH | CF |
| c-Pr | H | H | H | T | CH | CF |
| NO₂ | H | H | H | T | CH | CF |
| NH₂ | H | H | H | T | CH | CF |
| N(Me)H | H | H | H | T | CH | CF |
| N(Me)₂ | H | H | H | T | CH | CF |
| N(Me)n-Bu | H | H | H | T | CH | CF |
| N(nPen)H | H | H | H | T | CH | CF |
| NHCOPh | H | H | H | T | CH | CF |
| J¹ | H | H | H | T | CH | CF |
| NHC(=NH)NH₂ | H | H | H | T | CH | CF |
| C(=NH)NH₂ | H | H | H | T | CH | CF |
| CHO | H | H | H | T | CH | CF |
| CN | H | H | H | T | CH | CF |
| U | H | H | H | T | CH | CF |
| COOMe | H | H | H | T | CH | CF |
| CONH₂ | H | H | H | T | CH | CF |
| CONHCOMe | H | H | H | T | CH | CF |
| CH₂N(nPen)COPh | H | H | H | T | CH | CF |
| Ph | H | H | H | T | CH | CF |
| Bz | H | H | H | T | CH | CF |
| CH₂CH₂Ph | H | H | H | T | CH | CF |
| 2-thienyl | H | H | H | T | CH | CF |
| 3-furyl | H | H | H | T | CH | CF |
| Ph(4-J²) | H | H | H | T | CH | CF |
| Ph(2-Cl, 5-J¹) | H | H | H | T | CH | CF |
| T | H | H | H | T | CH | CF |
| F | H | H | H | T | CH | CCl |
| Cl | H | H | H | T | CH | CCl |
| Br | H | H | H | T | CH | CCl |
| I | H | H | H | T | CH | CCl |
| Me | H | H | H | T | CH | CCl |
| CF₃ | H | H | H | T | CH | CCl |
| Et | H | H | H | T | CH | CCl |
| n-Pr | H | H | H | T | CH | CCl |
| c-Pr | H | H | H | T | CH | CCl |
| NO₂ | H | H | H | T | CH | CCl |
| NH₂ | H | H | H | T | CH | CCl |
| N(Me)H | H | H | H | T | CH | CCl |
| N(Me)₂ | H | H | H | T | CH | CCl |
| N(Me)n-Bu | H | H | H | T | CH | CCl |
| N(nPen)H | H | H | H | T | CH | CCl |
| NHCOPh | H | H | H | T | CH | CCl |
| J¹ | H | H | H | T | CH | CCl |
| NHC(=NH)NH₂ | H | H | H | T | CH | CCl |
| C(=NH)NH₂ | H | H | H | T | CH | CCl |
| CHO | H | H | H | T | CH | CCl |
| CN | H | H | H | T | CH | CCl |
| U | H | H | H | T | CH | CCl |
| COOMe | H | H | H | T | CH | CCl |
| CONH₂ | H | H | H | T | CH | CCl |
| CONHCOMe | H | H | H | T | CH | CCl |
| CH₂N(nPen)COPh | H | H | H | T | CH | CCl |
| Ph | H | H | H | T | CH | CCl |
| Bz | H | H | H | T | CH | CCl |
| CH₂CH₂Ph | H | H | H | T | CH | CCl |
| 2-thienyl | H | H | H | T | CH | CCl |
| 3-furyl | H | H | H | T | CH | CCl |
| Ph(4-J²) | H | H | H | T | CH | CCl |
| Ph(2-Cl, 5-J¹) | H | H | H | T | CH | CCl |
| T | H | H | H | T | CH | CCl |
| F | H | H | H | T | CH | CBr |
| Cl | H | H | H | T | CH | CBr |
| Br | H | H | H | T | CH | CBr |
| I | H | H | H | T | CH | CBr |
| Me | H | H | H | T | CH | CBr |
| CF₃ | H | H | H | T | CH | CBr |
| Et | H | H | H | T | CH | CBr |
| n-Pr | H | H | H | T | CH | CBr |

TABLE 2-continued

| R³ | R⁴ | R⁵ | R⁶ | R⁷ | Y | Z |
|---|---|---|---|---|---|---|
| c-Pr | H | H | H | T | CH | CBr |
| NO₂ | H | H | H | T | CH | CBr |
| NH₂ | H | H | H | T | CH | CBr |
| N(Me)H | H | H | H | T | CH | CBr |
| N(Me)₂ | H | H | H | T | CH | CBr |
| N(Me)n-Bu | H | H | H | T | CH | CBr |
| N(nPen)H | H | H | H | T | CH | CBr |
| NHCOPh | H | H | H | T | CH | CBr |
| J¹ | H | H | H | T | CH | CBr |
| NHC(=NH)NH₂ | H | H | H | T | CH | CBr |
| C(=NH)NH₂ | H | H | H | T | CH | CBr |
| CHO | H | H | H | T | CH | CBr |
| CN | H | H | H | T | CH | CBr |
| U | H | H | H | T | CH | CBr |
| COOMe | H | H | H | T | CH | CBr |
| CONH₂ | H | H | H | T | CH | CBr |
| CONHCOMe | H | H | H | T | CH | CBr |
| CH₂N(nPen)COPh | H | H | H | T | CH | CBr |
| Ph | H | H | H | T | CH | CBr |
| Bz | H | H | H | T | CH | CBr |
| CH₂CH₂Ph | H | H | H | T | CH | CBr |
| 2-thienyl | H | H | H | T | CH | CBr |
| 3-furyl | H | H | H | T | CH | CBr |
| Ph(4-J²) | H | H | H | T | CH | CBr |
| Ph(2-Cl, 5-J¹) | H | H | H | T | CH | CBr |
| T | H | H | H | T | CH | CBr |
| F | H | H | H | T | CH | COH |
| Cl | H | H | H | T | CH | COH |
| Br | H | H | H | T | CH | COH |
| I | H | H | H | T | CH | COH |
| Me | H | H | H | T | CH | COH |
| CF₃ | H | H | H | T | CH | COH |
| Et | H | H | H | T | CH | COH |
| n-Pr | H | H | H | T | CH | COH |
| c-Pr | H | H | H | T | CH | COH |
| NO₂ | H | H | H | T | CH | COH |
| NH₂ | H | H | H | T | CH | COH |
| N(Me)H | H | H | H | T | CH | COH |
| N(Me)₂ | H | H | H | T | CH | COH |
| N(Me)n-Bu | H | H | H | T | CH | COH |
| N(nPen)H | H | H | H | T | CH | COH |
| NHCOPh | H | H | H | T | CH | COH |
| J¹ | H | H | H | T | CH | COH |
| NHC(=NH)NH₂ | H | H | H | T | CH | COH |
| C(=NH)NH₂ | H | H | H | T | CH | COH |
| CHO | H | H | H | T | CH | COH |
| CN | H | H | H | T | CH | COH |
| U | H | H | H | T | CH | COH |
| COOMe | H | H | H | T | CH | COH |
| CONH₂ | H | H | H | T | CH | COH |
| CONHCOMe | H | H | H | T | CH | COH |
| CH₂N(nPen)COPh | H | H | H | T | CH | COH |
| Ph | H | H | H | T | CH | COH |
| Bz | H | H | H | T | CH | COH |
| CH₂CH₂Ph | H | H | H | T | CH | COH |
| 2-thienyl | H | H | H | T | CH | COH |
| 3-furyl | H | H | H | T | CH | COH |
| Ph(4-J²) | H | H | H | T | CH | COH |
| Ph(2-Cl, 5-J¹) | H | H | H | T | CH | COH |
| T | H | H | H | T | CH | COH |
| F | H | H | H | T | CH | N |
| Cl | H | H | H | T | CH | N |
| Br | H | H | H | T | CH | N |
| I | H | H | H | T | CH | N |
| Me | H | H | H | T | CH | N |
| CF₃ | H | H | H | T | CH | N |
| Et | H | H | H | T | CH | N |
| n-Pr | H | H | H | T | CH | N |
| c-Pr | H | H | H | T | CH | N |
| NO₂ | H | H | H | T | CH | N |
| NH₂ | H | H | H | T | CH | N |
| N(Me)H | H | H | H | T | CH | N |
| N(Me)₂ | H | H | H | T | CH | N |
| N(Me)n-Bu | H | H | H | T | CH | N |
| N(nPen)H | H | H | H | T | CH | N |
| NHCOPh | H | H | H | T | CH | N |
| J¹ | H | H | H | T | CH | N |
| NHC(=NH)NH₂ | H | H | H | T | CH | N |
| C(=NH)NH₂ | H | H | H | T | CH | N |
| CHO | H | H | H | T | CH | N |
| CN | H | H | H | T | CH | N |
| U | H | H | H | T | CH | N |
| COOMe | H | H | H | T | CH | N |
| CONH₂ | H | H | H | T | CH | N |
| CONHCOMe | H | H | H | T | CH | N |
| CH₂N(nPen)COPh | H | H | H | T | CH | N |
| Ph | H | H | H | T | CH | N |
| Bz | H | H | H | T | CH | N |
| CH₂CH₂Ph | H | H | H | T | CH | N |
| 2-thienyl | H | H | H | T | CH | N |
| 3-furyl | H | H | H | T | CH | N |
| Ph(4-J²) | H | H | H | T | CH | N |
| Ph(2-Cl, 5-J¹) | H | H | H | T | CH | N |
| T | H | H | H | T | CH | N |

TABLE 3

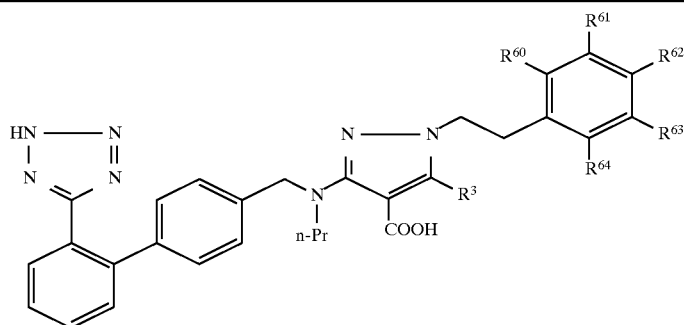

| R³ | R⁶⁰ | R⁶¹ | R⁶² | R⁶³ | R⁶⁴ |
|---|---|---|---|---|---|
| F | Me | H | H | H | H |
| Cl | Me | H | H | H | H |
| Br | Me | H | H | H | H |
| I | Me | H | H | H | H |
| Me | Me | H | H | H | H |
| CF₃ | Me | H | H | H | H |
| Et | Me | H | H | H | H |
| n-Pr | Me | H | H | H | H |
| c-Pr | Me | H | H | H | H |
| NO₂ | Me | H | H | H | H |
| NH₂ | Me | H | H | H | H |
| N(Me)n-Bu | Me | H | H | H | H |
| N(nPen)H | Me | H | H | H | H |
| NHCOPh | Me | H | H | H | H |
| J¹ | Me | H | H | H | H |
| U | Me | H | H | H | H |
| COOMe | Me | H | H | H | H |
| CONH₂ | Me | H | H | H | H |
| CONHCOMe | Me | H | H | H | H |
| CH₂N(nPen)COPh | Me | H | H | H | H |
| Ph | Me | H | H | H | H |
| Bz | Me | H | H | H | H |
| CH₂CH₂Ph | Me | H | H | H | H |
| 2-thienyl | Me | H | H | H | H |
| 3-furyl | Me | H | H | H | H |
| Ph(4-J²) | Me | H | H | H | H |
| Ph(2-Cl, 5-J¹) | Me | H | H | H | H |
| T | Me | H | H | H | H |
| F | H | Me | H | H | H |
| Cl | H | Me | H | H | H |
| Br | H | Me | H | H | H |
| I | H | Me | H | H | H |
| Me | H | Me | H | H | H |
| CF₃ | H | Me | H | H | H |
| Et | H | Me | H | H | H |
| n-Pr | H | Me | H | H | H |
| c-Pr | H | Me | H | H | H |
| NO₂ | H | Me | H | H | H |
| NH₂ | H | Me | H | H | H |
| N(Me)n-Bu | H | Me | H | H | H |
| N(nPen)H | H | Me | H | H | H |
| NHCOPh | H | Me | H | H | H |
| J¹ | H | Me | H | H | H |
| U | H | Me | H | H | H |
| COOMe | H | Me | H | H | H |
| CONH₂ | H | Me | H | H | H |
| CONHCOMe | H | Me | H | H | H |
| CH₂N(nPen)COPh | H | Me | H | H | H |
| Ph | H | Me | H | H | H |
| Bz | H | Me | H | H | H |
| CH₂CH₂Ph | H | Me | H | H | H |
| 2-thienyl | H | Me | H | H | H |
| 3-furyl | H | Me | H | H | H |
| Ph(4-J²) | H | Me | H | H | H |
| Ph(2-Cl, 5-J¹) | H | Me | H | H | H |
| T | H | Me | H | H | H |
| F | H | H | Me | H | H |
| Cl | H | H | Me | H | H |
| Br | H | H | Me | H | H |
| I | H | H | Me | H | H |

TABLE 3-continued

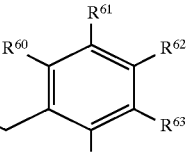

| R³ | R⁶⁰ | R⁶¹ | R⁶² | R⁶³ | R⁶⁴ |
|---|---|---|---|---|---|
| Me | H | H | Me | H | H |
| CF₃ | H | H | Me | H | H |
| Et | H | H | Me | H | H |
| n-Pr | H | H | Me | H | H |
| c-Pr | H | H | Me | H | H |
| NO₂ | H | H | Me | H | H |
| NH₂ | H | H | Me | H | H |
| N(nPen)H | H | H | Me | H | H |
| NHCOPh | H | H | Me | H | H |
| J¹ | H | H | Me | H | H |
| U | H | H | Me | H | H |
| COOMe | H | H | Me | H | H |
| CONH₂ | H | H | Me | H | H |
| CONHCOMe | H | H | Me | H | H |
| CH₂N(nPen)COPh | H | H | Me | H | H |
| Ph | H | H | Me | H | H |
| Bz | H | H | Me | H | H |
| CH₂CH₂Ph | H | H | Me | H | H |
| 2-thienyl | H | H | Me | H | H |
| 3-furyl | H | H | Me | H | H |
| Ph(4-J²) | H | H | Me | H | H |
| Ph(2-Cl, 5-J¹) | H | H | Me | H | H |
| T | H | H | Me | H | H |
| F | F | H | H | H | H |
| Cl | F | H | H | H | H |
| Br | F | H | H | H | H |
| I | F | H | H | H | H |
| Me | F | H | H | H | H |
| CF₃ | F | H | H | H | H |
| Et | F | H | H | H | H |
| n-Pr | F | H | H | H | H |
| c-Pr | F | H | H | H | H |
| NO₂ | F | H | H | H | H |
| NH₂ | F | H | H | H | H |
| N(Me)n-Bu | F | H | H | H | H |
| N(nPen)H | F | H | H | H | H |
| NHCOPh | F | H | H | H | H |
| J¹ | F | H | H | H | H |
| U | F | H | H | H | H |
| COOMe | F | H | H | H | H |
| CONH₂ | F | H | H | H | H |
| CONHCOMe | F | H | H | H | H |
| CH₂N(nPen)COPh | F | H | H | H | H |
| Ph | F | H | H | H | H |
| Bz | F | H | H | H | H |
| CH₂CH₂Ph | F | H | H | H | H |
| 2-thienyl | F | H | H | H | H |
| 3-furyl | F | H | H | H | H |
| Ph(4-J²) | F | H | H | H | H |
| Ph(2-Cl, 5-J¹) | F | H | H | H | H |
| T | F | H | H | H | H |
| F | H | F | H | H | H |
| Cl | H | F | H | H | H |
| Br | H | F | H | H | H |
| I | H | F | H | H | H |
| Me | H | F | H | H | H |
| CF₃ | H | F | H | H | H |
| Et | H | F | H | H | H |
| n-Pr | H | F | H | H | H |
| c-Pr | H | F | H | H | H |

TABLE 3-continued

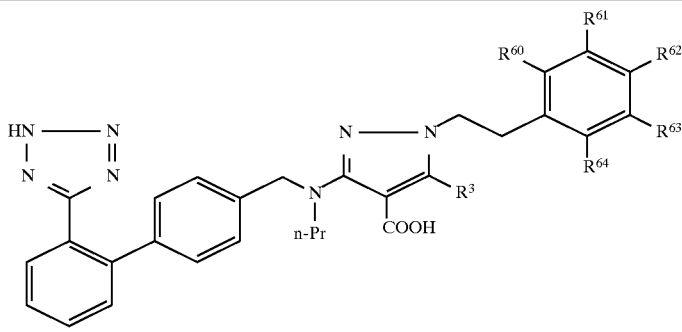

| $R^3$ | $R^{60}$ | $R^{61}$ | $R^{62}$ | $R^{63}$ | $R^{64}$ |
|---|---|---|---|---|---|
| $NO_2$ | H | F | H | H | H |
| N(Me)n-Bu | H | F | H | H | H |
| N(nPen)H | H | F | H | H | H |
| NHCOPh | H | F | H | H | H |
| $J^1$ | H | F | H | H | H |
| U | H | F | H | H | H |
| COOMe | H | F | H | H | H |
| $CONH_2$ | H | F | H | H | H |
| CONHCOMe | H | F | H | H | H |
| $CH_2N$(nPen)COPh | H | F | H | H | H |
| Ph | H | F | H | H | H |
| Bz | H | F | H | H | H |
| $CH_2CH_2Ph$ | H | F | H | H | H |
| 2-thienyl | H | F | H | H | H |
| 3-furyl | H | F | H | H | H |
| Ph(4-$J^2$) | H | F | H | H | H |
| Ph(2-Cl, 5-$J^1$) | H | F | H | H | H |
| T | H | F | H | H | H |
| F | H | H | F | H | H |
| Cl | H | H | F | H | H |
| Br | H | H | F | H | H |
| I | H | H | F | H | H |
| Me | H | H | F | H | H |
| $CF_3$ | H | H | F | H | H |
| Et | H | H | F | H | H |
| n-Pr | H | H | F | H | H |
| c-Pr | H | H | F | H | H |
| $NO_2$ | H | H | F | H | H |
| $NH_2$ | H | H | F | H | H |
| N(Me)n-Bu | H | H | F | H | H |
| N(nPen)H | H | H | F | H | H |
| NHCOPh | H | H | F | H | H |
| $J^1$ | H | H | F | H | H |
| U | H | H | F | H | H |
| COOMe | H | H | F | H | H |
| $CONH_2$ | H | H | F | H | H |
| CONHCOMe | H | H | F | H | H |
| $CH_2N$(nPen)COPh | H | H | F | H | H |
| Ph | H | H | F | H | H |
| Bz | H | H | F | H | H |
| $CH_2CH_2Ph$ | H | H | F | H | H |
| 2-thienyl | H | H | F | H | H |
| 3-furyl | H | H | F | H | H |
| Ph(4-$J^2$) | H | H | F | H | H |
| Ph(2-Cl, 5-$J^1$) | H | H | F | H | H |
| T | H | H | F | H | H |
| F | Cl | H | H | H | H |
| Cl | Cl | H | H | H | H |
| Br | Cl | H | H | H | H |
| I | Cl | H | H | H | H |
| Me | Cl | H | H | H | H |
| $CF_3$ | Cl | H | H | H | H |
| Et | Cl | H | H | H | H |
| n-Pr | Cl | H | H | H | H |
| c-Pr | Cl | H | H | H | H |
| $NO_2$ | Cl | H | H | H | H |
| $NH_2$ | Cl | H | H | H | H |
| N(Me)n-Bu | Cl | H | H | H | H |
| N(nPen)H | Cl | H | H | H | H |
| NHCOPh | Cl | H | H | H | H |

TABLE 3-continued

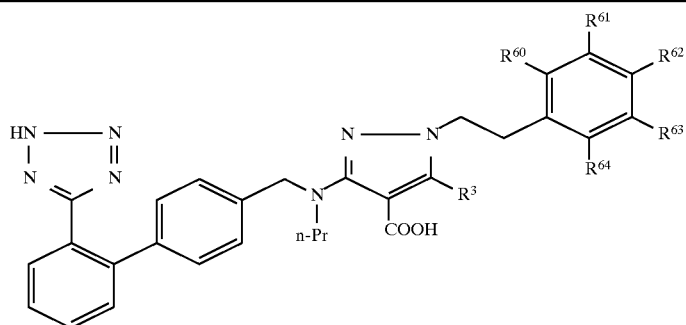

| R³ | R⁶⁰ | R⁶¹ | R⁶² | R⁶³ | R⁶⁴ |
|---|---|---|---|---|---|
| J¹ | Cl | H | H | H | H |
| U | Cl | H | H | H | H |
| COOMe | Cl | H | H | H | H |
| CONH₂ | Cl | H | H | H | H |
| CONHCOMe | Cl | H | H | H | H |
| CH₂N(nPen)COPh | Cl | H | H | H | H |
| Ph | Cl | H | H | H | H |
| Bz | Cl | H | H | H | H |
| CH₂CH₂Ph | Cl | H | H | H | H |
| 2-thienyl | Cl | H | H | H | H |
| 3-furyl | Cl | H | H | H | H |
| Ph(4-J²) | Cl | H | H | H | H |
| Ph(2-Cl, 5-J¹) | Cl | H | H | H | H |
| T | Cl | H | H | H | H |
| F | H | Cl | H | H | H |
| Cl | H | Cl | H | H | H |
| Br | H | Cl | H | H | H |
| I | H | Cl | H | H | H |
| Me | H | Cl | H | H | H |
| CF₃ | H | Cl | H | H | H |
| Et | H | Cl | H | H | H |
| n-Pr | H | Cl | H | H | H |
| c-Pr | H | Cl | H | H | H |
| NO₂ | H | Cl | H | H | H |
| NH₂ | H | Cl | H | H | H |
| N(Me)n-Bu | H | Cl | H | H | H |
| N(nPen)H | H | Cl | H | H | H |
| NHCOPh | H | Cl | H | H | H |
| J¹ | H | Cl | H | H | H |
| U | H | Cl | H | H | H |
| COOMe | H | Cl | H | H | H |
| CONH₂ | H | Cl | H | H | H |
| CONHCOMe | H | Cl | H | H | H |
| CH₂N(nPen)COPh | H | Cl | H | H | H |
| Ph | H | Cl | H | H | H |
| Bz | H | Cl | H | H | H |
| CH₂CH₂Ph | H | Cl | H | H | H |
| 2-thienyl | H | Cl | H | H | H |
| 3-furyl | H | Cl | H | H | H |
| Ph(4-J²) | H | Cl | H | H | H |
| Ph(2-Cl, 5-J¹) | H | Cl | H | H | H |
| T | H | Cl | H | H | H |
| F | H | H | Cl | H | H |
| Cl | H | H | Cl | H | H |
| Br | H | H | Cl | H | H |
| I | H | H | Cl | H | H |
| Me | H | H | Cl | H | H |
| CF₃ | H | H | Cl | H | H |
| Et | H | H | Cl | H | H |
| n-Pr | H | H | Cl | H | H |
| c-Pr | H | H | Cl | H | H |
| NO₂ | H | H | Cl | H | H |
| NH₂ | H | H | Cl | H | H |
| N(Me)n-Bu | H | H | Cl | H | H |
| N(nPen)H | H | H | Cl | H | H |
| NHCOPh | H | H | Cl | H | H |
| J¹ | H | H | Cl | H | H |
| U | H | H | Cl | H | H |
| COOMe | H | H | Cl | H | H |
| CONH₂ | H | H | Cl | H | H |

TABLE 3-continued

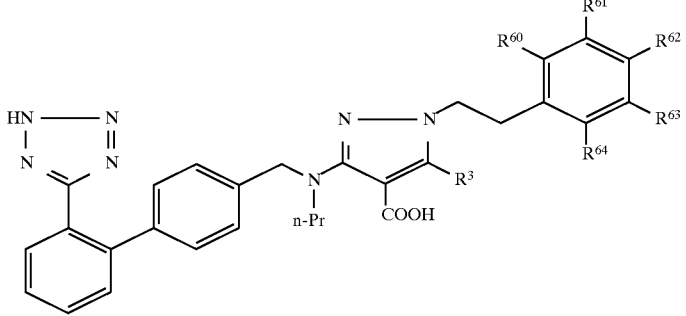

| R³ | R⁶⁰ | R⁶¹ | R⁶² | R⁶³ | R⁶⁴ |
|---|---|---|---|---|---|
| CONHCOMe | H | H | Cl | H | H |
| CH₂N(nPen)COPh | H | H | Cl | H | H |
| Ph | H | H | Cl | H | H |
| Bz | H | H | Cl | H | H |
| CH₂CH₂Ph | H | H | Cl | H | H |
| 2-thienyl | H | H | Cl | H | H |
| 3-furyl | H | H | Cl | H | H |
| Ph(4-J²) | H | H | Cl | H | H |
| Ph(2-Cl, 5-J¹) | H | H | Cl | H | H |
| T | H | H | Cl | H | H |
| F | Br | H | H | H | H |
| Cl | Br | H | H | H | H |
| Br | Br | H | H | H | H |
| I | Br | H | H | H | H |
| Me | Br | H | H | H | H |
| CF₃ | Br | H | H | H | H |
| Et | Br | H | H | H | H |
| n-Pr | Br | H | H | H | H |
| c-Pr | Br | H | H | H | H |
| NO₂ | Br | H | H | H | H |
| NH₂ | Br | H | H | H | H |
| N(Me)n-Bu | Br | H | H | H | H |
| N(nPen)H | Br | H | H | H | H |
| NHCOPh | Br | H | H | H | H |
| N(Me)CONHPh | Br | H | H | H | H |
| J¹ | Br | H | H | H | H |
| U | Br | H | H | H | H |
| COOMe | Br | H | H | H | H |
| CONH₂ | Br | H | H | H | H |
| CONHCOMe | Br | H | H | H | H |
| CH₂N(nPen)COPh | Br | H | H | H | H |
| Ph | Br | H | H | H | H |
| Bz | Br | H | H | H | H |
| CH₂CH₂Ph | Br | H | H | H | H |
| 2-thienyl | Br | H | H | H | H |
| 3-furyl | Br | H | H | H | H |
| Ph(4-J²) | Br | H | H | H | H |
| Ph(2-Cl, 5-J¹) | Br | H | H | H | H |
| T | Br | H | H | H | H |
| F | H | Br | H | H | H |
| Cl | H | Br | H | H | H |
| Br | H | Br | H | H | H |
| I | H | Br | H | H | H |
| Me | H | Br | H | H | H |
| CF₃ | H | Br | H | H | H |
| Et | H | Br | H | H | H |
| n-Pr | H | Br | H | H | H |
| c-Pr | H | Br | H | H | H |
| NO₂ | H | Br | H | H | H |
| NH₂ | H | Br | H | H | H |
| N(Me)n-Bu | H | Br | H | H | H |
| N(nPen)H | H | Br | H | H | H |
| NHCOPh | H | Br | H | H | H |
| J¹ | H | Br | H | H | H |
| U | H | Br | H | H | H |
| COOMe | H | Br | H | H | H |
| CONH₂ | H | Br | H | H | H |
| CONHCOMe | H | Br | H | H | H |
| CH₂N(nPen)COPh | H | Br | H | H | H |
| Ph | H | Br | H | H | H |

TABLE 3-continued

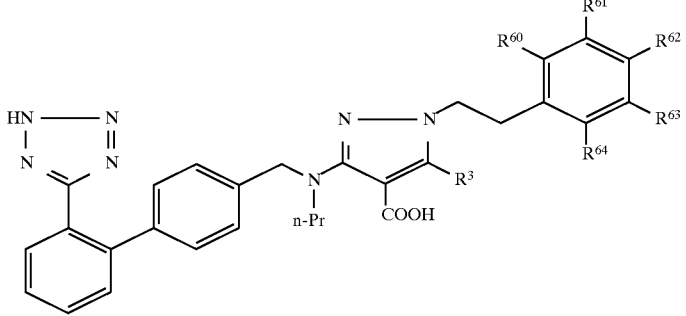

| R³ | R⁶⁰ | R⁶¹ | R⁶² | R⁶³ | R⁶⁴ |
|---|---|---|---|---|---|
| Bz | H | Br | H | H | H |
| CH₂CH₂Ph | H | Br | H | H | H |
| 2-thienyl | H | Br | H | H | H |
| 3-furyl | H | Br | H | H | H |
| Ph(4-J²) | H | Br | H | H | H |
| Ph(2-Cl, 5-J¹) | H | Br | H | H | H |
| T | H | Br | H | H | H |
| F | H | Br | H | H | H |
| Cl | H | Br | H | H | H |
| Br | H | Br | H | H | H |
| I | H | H | Br | H | H |
| Me | H | H | Br | H | H |
| CF₃ | H | H | Br | H | H |
| Et | H | H | Br | H | H |
| n-Pr | H | H | Br | H | H |
| c-Pr | H | H | Br | H | H |
| NO₂ | H | H | Br | H | H |
| N(Me)n-Bu | H | H | Br | H | H |
| N(nPen)H | H | H | Br | H | H |
| NHCOPh | H | H | Br | H | H |
| J¹ | H | H | Br | H | H |
| U | H | H | Br | H | H |
| COOMe | H | H | Br | H | H |
| CONH₂ | H | H | Br | H | H |
| CONHCOMe | H | H | Br | H | H |
| CH₂N(nPen)COPh | H | H | Br | H | H |
| Ph | H | H | Br | H | H |
| Bz | H | H | Br | H | H |
| CH₂CH₂Ph | H | H | Br | H | H |
| 2-thienyl | H | H | Br | H | H |
| 3-furyl | H | H | Br | H | H |
| Ph(4-J²) | H | H | Br | H | H |
| Ph(2-Cl, 5-J¹) | H | H | Br | H | H |
| T | H | H | Br | H | H |
| F | J² | H | H | H | H |
| Cl | J² | H | H | H | H |
| Br | J² | H | H | H | H |
| I | J² | H | H | H | H |
| Me | J² | H | H | H | H |
| CF₃ | J² | H | H | H | H |
| Et | J² | H | H | H | H |
| n-Pr | J² | H | H | H | H |
| c-Pr | J² | H | H | H | H |
| NO₂ | J² | H | H | H | H |
| NH₂ | J² | H | H | H | H |
| N(Me)n-Bu | J² | H | H | H | H |
| N(nPen)H | J² | H | H | H | H |
| NHCOPh | J² | H | H | H | H |
| J¹ | J² | H | H | H | H |
| U | J² | H | H | H | H |
| COOMe | J² | H | H | H | H |
| CONH₂ | J² | H | H | H | H |
| CONHCOMe | J² | H | H | H | H |
| CH₂N(nPen)COPh | J² | H | H | H | H |
| Ph | J² | H | H | H | H |
| Bz | J² | H | H | H | H |
| CH₂CH₂Ph | J² | H | H | H | H |
| 2-thienyl | J² | H | H | H | H |
| 3-furyl | J² | H | H | H | H |
| Ph(4-J²) | J² | H | H | H | H |

TABLE 3-continued

| R³ | R⁶⁰ | R⁶¹ | R⁶² | R⁶³ | R⁶⁴ |
|---|---|---|---|---|---|
| Ph(2-Cl, 5-J¹) | J² | H | H | H | H |
| T | J² | H | H | H | H |
| F | H | J² | H | H | H |
| Cl | H | J² | H | H | H |
| Br | H | J² | H | H | H |
| I | H | J² | H | H | H |
| Me | H | J² | H | H | H |
| CF₃ | H | J² | H | H | H |
| Et | H | J² | H | H | H |
| n-Pr | H | J² | H | H | H |
| c-Pr | H | J² | H | H | H |
| NO₂ | H | J² | H | H | H |
| NH₂ | H | J² | H | H | H |
| N(Me)n-Bu | H | J² | H | H | H |
| N(nPen)H | H | J² | H | H | H |
| NHCOPh | H | J² | H | H | H |
| J¹ | H | J² | H | H | H |
| U | H | J² | H | H | H |
| COOMe | H | J² | H | H | H |
| CONH₂ | H | J² | H | H | H |
| CONHCOMe | H | J² | H | H | H |
| CH₂N(nPen)COPh | H | J² | H | H | H |
| Ph | H | J² | H | H | H |
| Bz | H | J² | H | H | H |
| CH₂CH₂Ph | H | J² | H | H | H |
| 2-thienyl | H | J² | H | H | H |
| 3-furyl | H | J² | H | H | H |
| Ph(4-J²) | H | J² | H | H | H |
| Ph(2-Cl, 5-J¹) | H | J² | H | H | H |
| T | H | H | J² | H | H |
| F | H | H | J² | H | H |
| Cl | H | H | J² | H | H |
| Br | H | H | J² | H | H |
| I | H | H | J² | H | H |
| Me | H | H | J² | H | H |
| CF₃ | H | H | J² | H | H |
| Et | H | H | J² | H | H |
| n-Pr | H | H | J² | H | H |
| c-Pr | H | H | J² | H | H |
| NO₂ | H | H | J² | H | H |
| NH₂ | H | H | J² | H | H |
| N(Me)n-Bu | H | H | J² | H | H |
| N(nPen)H | H | H | J² | H | H |
| NHCOPh | H | H | J² | H | H |
| J¹ | H | H | J² | H | H |
| U | H | H | J² | H | H |
| COOMe | H | H | J² | H | H |
| CONH₂ | H | H | J² | H | H |
| CONHCOMe | H | H | J² | H | H |
| CH₂N(nPen)COPh | H | H | J² | H | H |
| Ph | H | H | J² | H | H |
| Bz | H | H | J² | H | H |
| CH₂CH₂Ph | H | H | J² | H | H |
| 2-thienyl | H | H | J² | H | H |
| 3-furyl | H | H | J² | H | H |
| Ph(4-J²) | H | H | J² | H | H |
| Ph(2-Cl, 5-J¹) | H | H | J² | H | H |
| T | H | H | J² | H | H |
| F | Cl | J¹ | H | H | H |
| Cl | Cl | J¹ | H | H | H |

TABLE 3-continued

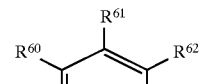

| $R^3$ | $R^{60}$ | $R^{61}$ | $R^{62}$ | $R^{63}$ | $R^{64}$ |
|---|---|---|---|---|---|
| Br | Cl | $J^1$ | H | H | H |
| I | Cl | $J^1$ | H | H | H |
| Me | Cl | $J^1$ | H | H | H |
| $CF_3$ | Cl | $J^1$ | H | H | H |
| Et | Cl | $J^1$ | H | H | H |
| n-Pr | Cl | $J^1$ | H | H | H |
| c-Pr | Cl | $J^1$ | H | H | H |
| $NO_2$ | Cl | $J^1$ | H | H | H |
| $NH_2$ | Cl | $J^1$ | H | H | H |
| $J^1$ | Cl | $J^1$ | H | H | H |
| U | Cl | $J^1$ | H | H | H |
| COOMe | Cl | $J^1$ | H | H | H |
| $CONH_2$ | Cl | $J^1$ | H | H | H |
| CONHCOMe | Cl | $J^1$ | H | H | H |
| $CH_2N(nPen)COPh$ | Cl | $J^1$ | H | H | H |
| Ph | Cl | $J^1$ | H | H | H |
| Bz | Cl | $J^1$ | H | H | H |
| $CH_2CH_2Ph$ | Cl | $J^1$ | H | H | H |
| 2-thienyl | Cl | $J^1$ | H | H | H |
| 3-furyl | Cl | $J^1$ | H | H | H |
| $Ph(4-J^2)$ | Cl | $J^1$ | H | H | H |
| $Ph(2-Cl, 5-J^1)$ | Cl | $J^1$ | H | H | H |
| T | Cl | $J^1$ | H | H | H |
| F | Cl | H | $J^1$ | H | H |
| Cl | Cl | H | $J^1$ | H | H |
| Br | Cl | H | $J^1$ | H | H |
| I | Cl | H | $J^1$ | H | H |
| Me | Cl | H | $J^1$ | H | H |
| $CF_3$ | Cl | H | $J^1$ | H | H |
| Et | Cl | H | $J^1$ | H | H |
| n-Pr | Cl | H | $J^1$ | H | H |
| c-Pr | Cl | H | $J^1$ | H | H |
| $NO_2$ | Cl | H | $J^1$ | H | H |
| $NH_2$ | Cl | H | $J^1$ | H | H |
| $J^1$ | Cl | H | $J^1$ | H | H |
| U | Cl | H | $J^1$ | H | H |
| COOMe | Cl | H | $J^1$ | H | H |
| $CONH_2$ | Cl | H | $J^1$ | H | H |
| CONHCOMe | Cl | H | $J^1$ | H | H |
| $CH_2N(nPen)COPh$ | Cl | H | $J^1$ | H | H |
| Ph | Cl | H | $J^1$ | H | H |
| Bz | Cl | H | $J^1$ | H | H |
| $CH_2CH_2Ph$ | Cl | H | $J^1$ | H | H |
| 2-thienyl | Cl | H | $J^1$ | H | H |
| 3-furyl | Cl | H | $J^1$ | H | H |
| $Ph(4-J^2)$ | Cl | H | $J^1$ | H | H |
| $Ph(2-Cl, 5-J^1)$ | Cl | H | $J^1$ | H | H |
| T | Cl | H | $J^1$ | H | H |
| F | Cl | H | H | $J^1$ | H |
| Cl | Cl | H | H | $J^1$ | H |
| Br | Cl | H | $J^1$ | H | H |
| I | Cl | H | H | $J^1$ | H |
| Me | Cl | H | H | $J^1$ | H |
| $CF_3$ | Cl | H | H | $J^1$ | H |
| Et | Cl | H | H | $J^1$ | H |
| n-Pr | Cl | H | H | $J^1$ | H |
| c-Pr | Cl | H | H | $J^1$ | H |
| $NO_2$ | Cl | H | H | $J^1$ | H |
| $NH_2$ | Cl | H | H | $J^1$ | H |
| N(Me)H | Cl | H | H | $J^1$ | H |

TABLE 3-continued

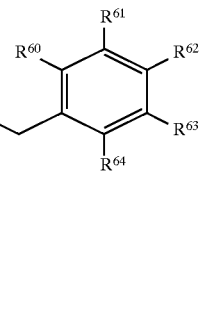

| R³ | R⁶⁰ | R⁶¹ | R⁶² | R⁶³ | R⁶⁴ |
|---|---|---|---|---|---|
| N(Me)₂ | Cl | H | H | J¹ | H |
| N(Me)n-Bu | Cl | H | H | J¹ | H |
| N(nPen)H | Cl | H | H | J¹ | H |
| NHCOPh | Cl | H | H | J¹ | H |
| N(Me)CO-c-Hex | Cl | H | H | J¹ | H |
| NHCONHMe | Cl | H | H | J¹ | H |
| N(Me)COHNPh | Cl | H | H | J¹ | H |
| NHCONH-c-Hex | Cl | H | H | J¹ | H |
| NHCOBz | Cl | H | H | J¹ | H |
| J¹ | Cl | H | H | J¹ | H |
| NBzCO-n-Bu | Cl | H | H | J¹ | H |
| NBzCOO-i-Bu | Cl | H | H | J¹ | H |
| NHCO-n-Bu | Cl | H | H | J¹ | H |
| NHCOO-i-Bu | Cl | H | H | J¹ | H |
| NHCOCF₃ | Cl | H | H | J¹ | H |
| NHSO₂CF₃ | Cl | H | H | J¹ | H |
| N(Me)Ph | Cl | H | H | J¹ | H |
| NHC(=NH)NH₂ | Cl | H | H | J¹ | H |
| C(=NH)NH₂ | Cl | H | H | J¹ | H |
| CHO | Cl | H | H | J¹ | H |
| CN | Cl | H | H | J¹ | H |
| U | Cl | H | H | J¹ | H |
| COOMe | Cl | H | H | J¹ | H |
| CONH₂ | Cl | H | H | J¹ | H |
| CONHCOMe | Cl | H | H | J¹ | H |
| CH₂NH₂ | Cl | H | H | J¹ | H |
| CH₂OH | Cl | H | H | J¹ | H |
| CH₂NHCOPh | Cl | H | H | J¹ | H |
| CH₂N(nPen)COPh | Cl | H | H | J¹ | H |
| CH₂NHCONHMe | Cl | H | H | J¹ | H |
| CH₂CONHPh | Cl | H | H | J¹ | H |
| CH₂COOH | Cl | H | H | J¹ | H |
| Ph | Cl | H | H | J¹ | H |
| Bz | Cl | H | H | J¹ | H |
| CH₂CH₂Ph | Cl | H | H | J¹ | H |
| 2-thienyl | Cl | H | H | J¹ | H |
| 3-furyl | Cl | H | H | J¹ | H |
| Ph(4-J²) | Cl | H | H | J¹ | H |
| Ph(2-Cl, 3-J¹) | Cl | H | H | J¹ | H |
| Ph(2-Cl, 4-J¹) | Cl | H | H | J¹ | H |
| Ph(2-Cl, 5-J¹) | Cl | H | H | J¹ | H |
| Ph(2-Cl, 6-J¹) | Cl | H | H | J¹ | H |
| CH₂CH₂Ph(2-Cl, 5-J¹) | Cl | H | H | J¹ | H |
| T | Cl | H | H | J¹ | H |
| F | Cl | H | H | H | J¹ |
| Cl | Cl | H | H | H | J¹ |
| Br | Cl | H | H | H | J¹ |
| I | Cl | H | H | H | J¹ |
| Me | Cl | H | H | H | J¹ |
| CF₃ | Cl | H | H | H | J¹ |
| Et | Cl | H | H | H | J¹ |
| N(Me)n-Bu | Cl | H | H | H | J¹ |
| N(nPen)H | Cl | H | H | H | J¹ |
| NHCOPh | Cl | H | H | H | J¹ |
| J¹ | Cl | H | H | H | J¹ |
| NHC(=NH)NH₂ | Cl | H | H | H | J¹ |
| C(=NH)NH₂ | Cl | H | H | H | J¹ |
| CHO | Cl | H | H | H | J¹ |
| CN | Cl | H | H | H | J¹ |
| U | Cl | H | H | H | J¹ |

TABLE 3-continued

| R³ | R⁶⁰ | R⁶¹ | R⁶² | R⁶³ | R⁶⁴ |
|---|---|---|---|---|---|
| COOMe | Cl | H | H | H | J¹ |
| CONH₂ | Cl | H | H | H | J¹ |
| CONHCOMe | Cl | H | H | H | J¹ |
| CH₂N(nPen)COPh | Cl | H | H | H | J¹ |
| Ph | Cl | H | H | H | J¹ |
| Bz | Cl | H | H | H | J¹ |
| CH₂CH₂Ph | Cl | H | H | H | J¹ |
| Ph(4-J²) | Cl | H | H | H | J¹ |
| Ph(2-Cl, 5-J¹) | Cl | H | H | H | J¹ |

TABLE 4

| R¹ | R³ | R⁶⁰ | R⁶¹ | R⁶² | R⁶³ | R⁶⁴ |
|---|---|---|---|---|---|---|
| n-Pr | F | H | H | H | H | H |
| n-Pr | Cl | H | H | H | H | H |
| n-Pr | Br | H | H | H | H | H |
| n-Pr | I | H | H | H | H | H |
| n-Pr | Me | H | H | H | H | H |
| n-Pr | CF₃ | H | H | H | H | H |
| n-Pr | Et | H | H | H | H | H |
| n-Pr | n-Pr | H | H | H | H | H |
| n-Pr | c-Pr | H | H | H | H | H |
| n-Pr | NO₂ | H | H | H | H | H |
| n-Pr | NH₂ | H | H | H | H | H |
| n-Pr | N(Me)n-Bu | H | H | H | H | H |
| n-Pr | N(nPen)H | H | H | H | H | H |
| n-Pr | NHCOPh | H | H | H | H | H |
| n-Pr | U | H | H | H | H | H |
| n-Pr | CONH₂ | H | H | H | H | H |
| n-Pr | CONHCOMe | H | H | H | H | H |
| n-Pr | CH₂N(nPen)COPh | H | H | H | H | H |
| n-Pr | Ph(2-Cl,5-J¹) | H | H | H | H | H |
| n-Pr | OH | H | H | H | H | H |
| n-Pr | T | H | H | H | H | H |
| Et | F | H | H | H | H | H |
| Et | Cl | H | H | H | H | H |
| Et | Br | H | H | H | H | H |
| Et | I | H | H | H | H | H |
| Et | Me | H | H | H | H | H |
| Et | CF₃ | H | H | H | H | H |
| Et | NO₂ | H | H | H | H | H |

TABLE 4-continued

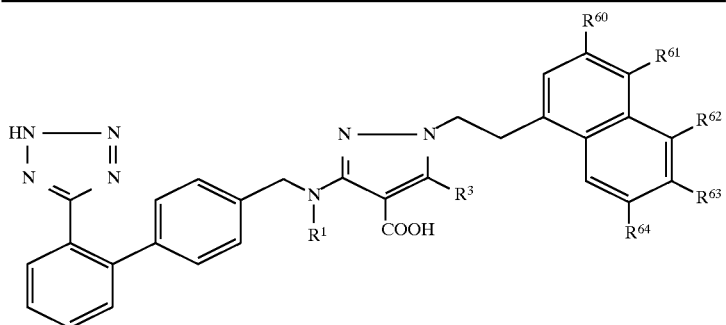

| R¹ | R³ | R⁶⁰ | R⁶¹ | R⁶² | R⁶³ | R⁶⁴ |
|---|---|---|---|---|---|---|
| Et | NH₂ | H | H | H | H | H |
| Et | NHCOPh | H | H | H | H | H |
| Et | OH | H | H | H | H | H |
| Et | T | H | H | H | H | H |
| n-Bu | F | H | H | H | H | H |
| n-Bu | Cl | H | H | H | H | H |
| n-Bu | Br | H | H | H | H | H |
| n-Bu | I | H | H | H | H | H |
| n-Bu | Me | H | H | H | H | H |
| n-Bu | CF₃ | H | H | H | H | H |
| n-Bu | NO₂ | H | H | H | H | H |
| n-Bu | NH₂ | H | H | H | H | H |
| n-Bu | N(Me)CO-c-Hex | H | H | H | H | H |
| n-Bu | NHCONH-c-Hex | H | H | H | H | H |
| n-Bu | OH | H | H | H | H | H |
| n-Bu | T | H | H | H | H | H |
| n-Pr | F | Me | H | H | H | H |
| n-Pr | Cl | Me | H | H | H | H |
| n-Pr | Br | Me | H | H | H | H |
| n-Pr | I | Me | H | H | H | H |
| n-Pr | Me | Me | H | H | H | H |
| n-Pr | CF₃ | Me | H | H | H | H |
| n-Pr | Et | Me | H | H | H | H |
| n-Pr | n-Pr | Me | H | H | H | H |
| n-Pr | c-Pr | Me | H | H | H | H |
| n-Pr | NO₂ | Me | H | H | H | H |
| n-Pr | NH₂ | Me | H | H | H | H |
| n-Pr | NHCOPh | Me | H | H | H | H |
| n-Pr | J¹ | Me | H | H | H | H |
| n-Pr | NHC(=NH)NH₂ | Me | H | H | H | H |
| n-Pr | C(=NH)NH₂ | Me | H | H | H | H |
| n-Pr | CHO | Me | H | H | H | H |
| n-Pr | CN | Me | H | H | H | H |
| n-Pr | U | Me | H | H | H | H |
| n-Pr | CONH₂ | Me | H | H | H | H |
| n-Pr | CH₂N(nPen)COPh | Me | H | H | H | H |
| n-Pr | Ph | Me | H | H | H | H |
| n-Pr | Bz | Me | H | H | H | H |
| n-Pr | CH₂CH₂Ph | Me | H | H | H | H |
| n-Pr | 2-thienyl | Me | H | H | H | H |
| n-Pr | 3-furyl | Me | H | H | H | H |
| n-Pr | Ph(4-J²) | Me | H | H | H | H |
| n-Pr | Ph(2-Cl,5-J¹) | Me | H | H | H | H |
| n-Pr | T | Me | H | H | H | H |
| n-Pr | F | H | Me | H | H | H |
| n-Pr | Cl | H | Me | H | H | H |
| n-Pr | Br | H | Me | H | H | H |
| n-Pr | I | H | Me | H | H | H |
| n-Pr | Me | H | Me | H | H | H |
| n-Pr | CF₃ | H | Me | H | H | H |
| n-Pr | NO₂ | H | Me | H | H | H |
| n-Pr | NH₂ | H | Me | H | H | H |
| n-Pr | NHCOPh | H | Me | H | H | H |
| n-Pr | J¹ | H | Me | H | H | H |
| n-Pr | NHC(=NH)NH₂ | H | Me | H | H | H |
| n-Pr | C(=NH)NH₂ | H | Me | H | H | H |
| n-Pr | CHO | H | Me | H | H | H |
| n-Pr | CN | H | Me | H | H | H |
| n-Pr | U | H | Me | H | H | H |
| n-Pr | CONH₂ | H | Me | H | H | H |

TABLE 4-continued

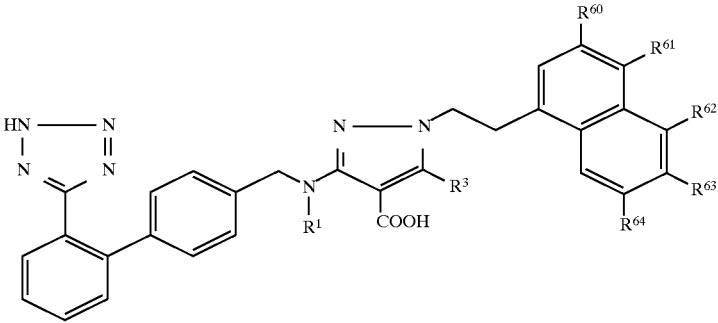

| R[1] | R[3] | R[60] | R[61] | R[62] | R[63] | R[64] |
|---|---|---|---|---|---|---|
| n-Pr | CH$_2$N(nPen)COPh | H | Me | H | H | H |
| n-Pr | Ph | H | Me | H | H | H |
| n-Pr | Bz | H | Me | H | H | H |
| n-Pr | CH$_2$CH$_2$Ph | H | Me | H | H | H |
| n-Pr | 2-thienyl | H | Me | H | H | H |
| n-Pr | 3-furyl | H | Me | H | H | H |
| n-Pr | Ph(4-J$^2$) | H | Me | H | H | H |
| n-Pr | Ph(2-Cl,5-J$^1$) | H | Me | H | H | H |
| n-Pr | T | H | Me | H | H | H |
| n-Pr | F | H | H | Me | H | H |
| n-Pr | Cl | H | H | Me | H | H |
| n-Pr | Br | H | H | Me | H | H |
| n-Pr | I | H | H | Me | H | H |
| n-Pr | Me | H | H | Me | H | H |
| n-Pr | CF$_3$ | H | H | Me | H | H |
| n-Pr | NO$_2$ | H | H | Me | H | H |
| n-Pr | NH$_2$ | H | H | Me | H | H |
| n-Pr | NHCOPh | H | H | Me | H | H |
| n-Pr | J$^1$ | H | H | Me | H | H |
| n-Pr | NHC(=NH)NH$_2$ | H | H | Me | H | H |
| n-Pr | C(=NH)NH$_2$ | H | H | Me | H | H |
| n-Pr | CHO | H | H | Me | H | H |
| n-Pr | CN | H | H | Me | H | H |
| n-Pr | U | H | H | Me | H | H |
| n-Pr | CONH$_2$ | H | H | Me | H | H |
| n-Pr | CH$_2$N(nPen)COPh | H | H | Me | H | H |
| n-Pr | Ph | H | H | Me | H | H |
| n-Pr | Bz | H | H | Me | H | H |
| n-Pr | CH$_2$CH$_2$Ph | H | H | Me | H | H |
| n-Pr | 2-thienyl | H | H | Me | H | H |
| n-Pr | 3-furyl | H | H | Me | H | H |
| n-Pr | Ph(4-J$^2$) | H | H | Me | H | H |
| n-Pr | Ph(2-Cl,5-J$^1$) | H | H | Me | H | H |
| n-Pr | T | H | H | Me | H | H |
| n-Pr | F | H | H | H | Me | H |
| n-Pr | Cl | H | H | H | Me | H |
| n-Pr | Br | H | H | H | Me | H |
| n-Pr | I | H | H | H | Me | H |
| n-Pr | Me | H | H | H | Me | H |
| n-Pr | CF$_3$ | H | H | H | Me | H |
| n-Pr | Et | H | H | H | Me | H |
| n-Pr | n-Pr | H | H | H | Me | H |
| n-Pr | c-Pr | H | H | H | Me | H |
| n-Pr | NO$_2$ | H | H | H | Me | H |
| n-Pr | NH$_2$ | H | H | H | Me | H |
| n-Pr | NHCOPh | H | H | H | Me | H |
| n-Pr | J$^1$ | H | H | H | Me | H |
| n-Pr | NHC(=NH)NH$_2$ | H | H | H | Me | H |
| n-Pr | C(=NH)NH$_2$ | H | H | H | Me | H |
| n-Pr | CHO | H | H | H | Me | H |
| n-Pr | CN | H | H | H | Me | H |
| n-Pr | U | H | H | H | Me | H |
| n-Pr | CONH$_2$ | H | H | H | Me | H |
| n-Pr | CH$_2$N(nPen)COPh | H | H | H | Me | H |
| n-Pr | Ph | H | H | H | Me | H |
| n-Pr | Bz | H | H | H | Me | H |
| n-Pr | CH$_2$CH$_2$Ph | H | H | H | Me | H |
| n-Pr | 2-thienyl | H | H | H | Me | H |
| n-Pr | 3-furyl | H | H | H | Me | H |
| n-Pr | Ph(4-J$^2$) | H | H | H | Me | H |

TABLE 4-continued

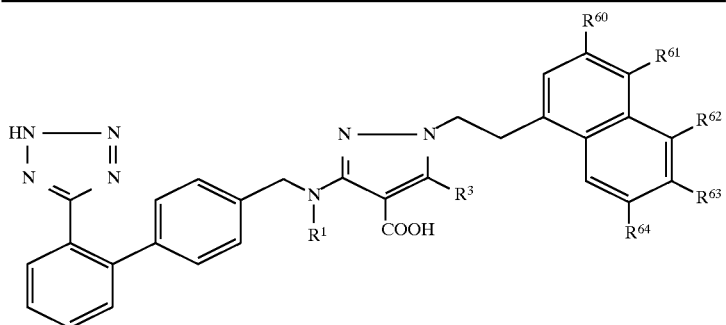

| R¹ | R³ | R⁶⁰ | R⁶¹ | R⁶² | R⁶³ | R⁶⁴ |
|---|---|---|---|---|---|---|
| n-Pr | Ph(2-Cl,5-J¹) | H | H | H | Me | H |
| n-Pr | T | H | H | H | Me | H |
| n-Pr | F | H | H | H | H | Me |
| n-Pr | Cl | H | H | H | H | Me |
| n-Pr | Br | H | H | H | H | Me |
| n-Pr | I | H | H | H | H | Me |
| n-Pr | Me | H | H | H | H | Me |
| n-Pr | CF₃ | H | H | H | H | Me |
| n-Pr | Et | H | H | H | H | Me |
| n-Pr | n-Pr | H | H | H | H | Me |
| n-Pr | c-Pr | H | H | H | H | Me |
| n-Pr | NO₂ | H | H | H | H | Me |
| n-Pr | NH₂ | H | H | H | H | Me |
| n-Pr | NHCOPh | H | H | H | H | Me |
| n-Pr | J¹ | H | H | H | H | Me |
| n-Pr | NHC(=NH)NH₂ | H | H | H | H | Me |
| n-Pr | C(=NH)NH₂ | H | H | H | H | Me |
| n-Pr | CHO | H | H | H | H | Me |
| n-Pr | CN | H | H | H | H | Me |
| n-Pr | U | H | H | H | H | Me |
| n-Pr | CONH₂ | H | H | H | H | Me |
| n-Pr | CH₂N(nPen)COPh | H | H | H | H | Me |
| n-Pr | Ph | H | H | H | H | Me |
| n-Pr | Bz | H | H | H | H | Me |
| n-Pr | CH₂CH₂Ph | H | H | H | H | Me |
| n-Pr | 2-thienyl | H | H | H | H | Me |
| n-Pr | 3-furyl | H | H | H | H | Me |
| n-Pr | Ph(4-J²) | H | H | H | H | Me |
| n-Pr | Ph(2-Cl,5-J¹) | H | H | H | H | Me |
| n-Pr | T | H | H | H | H | Me |
| n-Pr | F | F | H | H | H | H |
| n-Pr | Cl | F | H | H | H | H |
| n-Pr | Br | F | H | H | H | H |
| n-Pr | I | F | H | H | H | H |
| n-Pr | Me | F | H | H | H | H |
| n-Pr | CF₃ | F | H | H | H | H |
| n-Pr | F | H | Cl | H | H | H |
| n-Pr | Cl | H | Cl | H | H | H |
| n-Pr | Br | H | Cl | H | H | H |
| n-Pr | I | H | Cl | H | H | H |
| n-Pr | Me | H | Cl | H | H | H |
| n-Pr | CF₃ | H | Cl | H | H | H |
| n-Pr | F | H | H | Br | H | H |
| n-Pr | Cl | H | H | Br | H | H |
| n-Pr | Br | H | H | Br | H | H |
| n-Pr | I | H | H | Br | H | H |
| n-Pr | Me | H | H | Br | H | H |
| n-Pr | CF₃ | H | H | Br | H | H |
| n-Pr | F | H | H | H | J² | H |
| n-Pr | Cl | H | H | H | J² | H |
| n-Pr | Br | H | H | H | J² | H |
| n-Pr | I | H | H | H | J² | H |
| n-Pr | Me | H | H | H | J² | H |
| n-Pr | CF₃ | H | H | H | J² | H |
| n-Pr | Et | H | H | H | J² | H |
| n-Pr | n-Pr | H | H | H | J² | H |
| n-Pr | F | Cl | H | H | H | J¹ |
| n-Pr | Cl | Cl | H | H | H | J¹ |
| n-Pr | Br | Cl | H | H | H | J¹ |
| n-Pr | I | Cl | H | H | H | J¹ |

TABLE 4-continued

[Structure diagram: tetrazole-biphenyl-CH2-N(R1)-pyrazole(COOH, R3)-N-CH2CH2-naphthyl(R60,R61,R62,R63,R64)]

| R¹ | R³ | R⁶⁰ | R⁶¹ | R⁶² | R⁶³ | R⁶⁴ |
|---|---|---|---|---|---|---|
| n-Pr | Me | Cl | H | H | H | J¹ |
| n-Pr | CF₃ | Cl | H | H | H | J¹ |
| n-Pr | Et | Cl | H | H | H | J¹ |
| n-Pr | n-Pr | Cl | H | H | H | J¹ |

TABLE 5

[Structure diagram: tetrazole-biphenyl-CH2-N(R1)-pyrazole(COOH, R3)-N-CH2CH2-naphthyl(R60,R61,R62,R63,R64)]

| R¹ | R³ | R⁶⁰ | R⁶¹ | R⁶² | R⁶³ | R⁶⁴ |
|---|---|---|---|---|---|---|
| n-Pr | F | H | H | H | H | H |
| n-Pr | Cl | H | H | H | H | H |
| n-Pr | Br | H | H | H | H | H |
| n-Pr | I | H | H | H | H | H |
| n-Pr | Me | H | H | H | H | H |
| n-Pr | CF₃ | H | H | H | H | H |
| n-Pr | Et | H | H | H | H | H |
| n-Pr | n-Pr | H | H | H | H | H |
| n-Pr | c-Pr | H | H | H | H | H |
| n-Pr | NO₂ | H | H | H | H | H |
| n-Pr | NH₂ | H | H | H | H | H |
| n-Pr | N(Me)n-Bu | H | H | H | H | H |
| n-Pr | N(nPen)H | H | H | H | H | H |
| n-Pr | NHCOPh | H | H | H | H | H |
| n-Pr | U | H | H | H | H | H |
| n-Pr | CONH₂ | H | H | H | H | H |
| n-Pr | CONHCOMe | H | H | H | H | H |
| n-Pr | CH₂N(nPen)COPh | H | H | H | H | H |
| n-Pr | Ph(2-Cl,5-J¹) | H | H | H | H | H |
| n-Pr | OH | H | H | H | H | H |
| n-Pr | T | H | H | H | H | H |
| Et | F | H | H | H | H | H |
| Et | Cl | H | H | H | H | H |
| Et | Br | H | H | H | H | H |
| Et | I | H | H | H | H | H |
| Et | Me | H | H | H | H | H |
| Et | CF₃ | H | H | H | H | H |
| Et | NO₂ | H | H | H | H | H |
| Et | NH₂ | H | H | H | H | H |
| Et | NHCOPh | H | H | H | H | H |
| Et | OH | H | H | H | H | H |
| Et | T | H | H | H | H | H |
| n-Bu | F | H | H | H | H | H |

TABLE 5-continued

[Chemical structure showing a tetrazole-biphenyl-pyrazole-naphthalene compound with substituents R¹, R³, R⁶⁰, R⁶¹, R⁶², R⁶³, R⁶⁴ and COOH group]

| R¹ | R³ | R⁶⁰ | R⁶¹ | R⁶² | R⁶³ | R⁶⁴ |
|---|---|---|---|---|---|---|
| n-Bu | Cl | H | H | H | H | H |
| n-Bu | Br | H | H | H | H | H |
| n-Bu | I | H | H | H | H | H |
| n-Bu | Me | H | H | H | H | H |
| n-Bu | $CF_3$ | H | H | H | H | H |
| n-Bu | $NO_2$ | H | H | H | H | H |
| n-Bu | $NH_2$ | H | H | H | H | H |
| n-Bu | N(Me)CO-c-Hex | H | H | H | H | H |
| n-Bu | NHCONH-c-Hex | H | H | H | H | H |
| n-Bu | OH | H | H | H | H | H |
| n-Bu | T | H | H | H | H | H |
| n-Pr | F | Me | H | H | H | H |
| n-Pr | Cl | Me | H | H | H | H |
| n-Pr | Br | Me | H | H | H | H |
| n-Pr | I | Me | H | H | H | H |
| n-Pr | Me | Me | H | H | H | H |
| n-Pr | $CF_3$ | Me | H | H | H | H |
| n-Pr | Et | Me | H | H | H | H |
| n-Pr | n-Pr | Me | H | H | H | H |
| n-Pr | c-Pr | Me | H | H | H | H |
| n-Pr | $NO_2$ | Me | H | H | H | H |
| n-Pr | $NH_2$ | Me | H | H | H | H |
| n-Pr | NHCOPh | Me | H | H | H | H |
| n-Pr | $J^1$ | Me | H | H | H | H |
| n-Pr | $NHC(=NH)NH_2$ | Me | H | H | H | H |
| n-Pr | $C(=NH)NH_2$ | Me | H | H | H | H |
| n-Pr | CHO | Me | H | H | H | H |
| n-Pr | CN | Me | H | H | H | H |
| n-Pr | U | Me | H | H | H | H |
| n-Pr | $CONH_2$ | Me | H | H | H | H |
| n-Pr | $CH_2N(nPen)COPh$ | Me | H | H | H | H |
| n-Pr | Ph | Me | H | H | H | H |
| n-Pr | Bz | Me | H | H | H | H |
| n-Pr | $CH_2CH_2Ph$ | Me | H | H | H | H |
| n-Pr | 2-thienyl | Me | H | H | H | H |
| n-Pr | 3-furyl | Me | H | H | H | H |
| n-Pr | $Ph(4-J^2)$ | Me | H | H | H | H |
| n-Pr | $Ph(2-Cl,5-J^1)$ | Me | H | H | H | H |
| n-Pr | T | Me | H | H | H | H |
| n-Pr | F | H | Me | H | H | H |
| n-Pr | Cl | H | Me | H | H | H |
| n-Pr | Br | H | Me | H | H | H |
| n-Pr | I | H | Me | H | H | H |
| n-Pr | Me | H | Me | H | H | H |
| n-Pr | $CF_3$ | H | Me | H | H | H |
| n-Pr | $NO_2$ | H | Me | H | H | H |
| n-Pr | $NH_2$ | H | Me | H | H | H |
| n-Pr | NHCOPh | H | Me | H | H | H |
| n-Pr | $J^1$ | H | Me | H | H | H |
| n-Pr | $NHC(=NH)NH_2$ | H | Me | H | H | H |
| n-Pr | $C(=NH)NH_2$ | H | Me | H | H | H |
| n-Pr | CHO | H | Me | H | H | H |
| n-Pr | CN | H | Me | H | H | H |
| n-Pr | U | H | Me | H | H | H |
| n-Pr | $CONH_2$ | H | Me | H | H | H |
| n-Pr | $CH_2N(nPen)COPh$ | H | Me | H | H | H |
| n-Pr | Ph | H | Me | H | H | H |
| n-Pr | Bz | H | Me | H | H | H |
| n-Pr | $CH_2CH_2Ph$ | H | Me | H | H | H |
| n-Pr | 2-thienyl | H | Me | H | H | H |

TABLE 5-continued

| R¹ | R³ | R⁶⁰ | R⁶¹ | R⁶² | R⁶³ | R⁶⁴ |
|---|---|---|---|---|---|---|
| n-Pr | 3-furyl | H | Me | H | H | H |
| n-Pr | Ph(4-J²) | H | Me | H | H | H |
| n-Pr | Ph(2-Cl,5-J¹) | H | Me | H | H | H |
| n-Pr | T | H | Me | H | H | H |
| n-Pr | F | H | H | Me | H | H |
| n-Pr | Cl | H | H | Me | H | H |
| n-Pr | Br | H | H | Me | H | H |
| n-Pr | I | H | H | Me | H | H |
| n-Pr | Me | H | H | Me | H | H |
| n-Pr | CF₃ | H | H | Me | H | H |
| n-Pr | NO₂ | H | H | Me | H | H |
| n-Pr | NH₂ | H | H | Me | H | H |
| n-Pr | NHCOPh | H | H | Me | H | H |
| n-Pr | J¹ | H | H | Me | H | H |
| n-Pr | NHC(=NH)NH₂ | H | H | Me | H | H |
| n-Pr | C(=NH)NH₂ | H | H | Me | H | H |
| n-Pr | CHO | H | H | Me | H | H |
| n-Pr | CN | H | H | Me | H | H |
| n-Pr | U | H | H | Me | H | H |
| n-Pr | CONH₂ | H | H | Me | H | H |
| n-Pr | CH₂N(nPen)COPh | H | H | Me | H | H |
| n-Pr | Ph | H | H | Me | H | H |
| n-Pr | Bz | H | H | Me | H | H |
| n-Pr | CH₂CH₂Ph | H | H | Me | H | H |
| n-Pr | 2-thienyl | H | H | Me | H | H |
| n-Pr | 3-furyl | H | H | Me | H | H |
| n-Pr | Ph(4-J²) | H | H | Me | H | H |
| n-Pr | Ph(2-Cl,5-J¹) | H | H | Me | H | H |
| n-Pr | T | H | H | Me | H | H |
| n-Pr | F | H | H | H | Me | H |
| n-Pr | Cl | H | H | H | Me | H |
| n-Pr | Br | H | H | H | Me | H |
| n-Pr | I | H | H | H | Me | H |
| n-Pr | Me | H | H | Me | H | H |
| n-Pr | CF₃ | H | H | H | Me | H |
| n-Pr | Et | H | H | H | Me | H |
| n-Pr | n-Pr | H | H | H | Me | H |
| n-Pr | c-Pr | H | H | H | Me | H |
| n-Pr | NO₂ | H | H | H | Me | H |
| n-Pr | NH₂ | H | H | H | Me | H |
| n-Pr | NHCOPh | H | H | H | Me | H |
| n-Pr | J¹ | H | H | H | Me | H |
| n-Pr | NHC(=NH)NH₂ | H | H | H | Me | H |
| n-Pr | C(=NH)NH₂ | H | H | H | Me | H |
| n-Pr | CHO | H | H | H | Me | H |
| n-Pr | CN | H | H | H | Me | H |
| n-Pr | U | H | H | H | Me | H |
| n-Pr | CONH₂ | H | H | H | Me | H |
| n-Pr | CH₂N(nPen)COPh | H | H | H | Me | H |
| n-Pr | Ph | H | H | H | Me | H |
| n-Pr | Bz | H | H | H | Me | H |
| n-Pr | CH₂CH₂Ph | H | H | H | Me | H |
| n-Pr | 2-thienyl | H | H | H | Me | H |
| n-Pr | 3-furyl | H | H | H | Me | H |
| n-Pr | Ph(4-J²) | H | H | H | Me | H |
| n-Pr | Ph(2-Cl,5-J¹) | H | H | H | Me | H |
| n-Pr | T | H | H | H | Me | H |
| n-Pr | F | H | H | H | H | Me |
| n-Pr | Cl | H | H | H | H | Me |
| n-Pr | Br | H | H | H | H | Me |

TABLE 5-continued

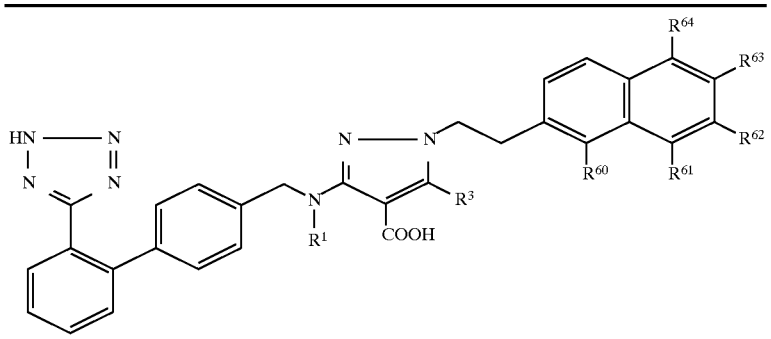

| $R^1$ | $R^3$ | $R^{60}$ | $R^{61}$ | $R^{62}$ | $R^{63}$ | $R^{64}$ |
|---|---|---|---|---|---|---|
| n-Pr | I | H | H | H | H | Me |
| n-Pr | Me | H | H | H | Me | H |
| n-Pr | $CF_3$ | H | H | H | H | Me |
| n-Pr | Et | H | H | H | H | Me |
| n-Pr | n-Pr | H | H | H | H | Me |
| n-Pr | c-Pr | H | H | H | H | Me |
| n-Pr | $NO_2$ | H | H | H | H | Me |
| n-Pr | $NH_2$ | H | H | H | H | Me |
| n-Pr | NHCOPh | H | H | H | H | Me |
| n-Pr | $J^1$ | H | H | H | H | Me |
| n-Pr | NHC(=NH)$NH_2$ | H | H | H | H | Me |
| n-Pr | C(=NH)$NH_2$ | H | H | H | H | Me |
| n-Pr | CHO | H | H | H | H | Me |
| n-Pr | CN | H | H | H | H | Me |
| n-Pr | U | H | H | H | H | Me |
| n-Pr | $CONH_2$ | H | H | H | H | Me |
| n-Pr | $CH_2$N(nPen)COPh | H | H | H | H | Me |
| n-Pr | Ph | H | H | H | H | Me |
| n-Pr | Bz | H | H | H | H | Me |
| n-Pr | $CH_2CH_2$Ph | H | H | H | H | Me |
| n-Pr | 2-thienyl | H | H | H | H | Me |
| n-Pr | 3-furyl | H | H | H | H | Me |
| n-Pr | Ph(4-$J^2$) | H | H | H | H | Me |
| n-Pr | Ph(2-Cl,5-$J^1$) | H | H | H | H | Me |
| n-Pr | T | H | H | H | H | Me |
| n-Pr | F | F | H | H | H | H |
| n-Pr | Cl | F | H | H | H | H |
| n-Pr | Br | F | H | H | H | H |
| n-Pr | I | F | H | H | H | H |
| n-Pr | Me | F | H | H | H | H |
| n-Pr | $CF_3$ | F | H | H | H | H |
| n-Pr | F | H | Cl | H | H | H |
| n-Pr | Cl | H | Cl | H | H | H |
| n-Pr | Br | H | Cl | H | H | H |
| n-Pr | I | H | Cl | H | H | H |
| n-Pr | Me | H | Cl | H | H | H |
| n-Pr | $CF_3$ | H | Cl | H | H | H |
| n-Pr | F | H | H | Br | H | H |
| n-Pr | Cl | H | H | Br | H | H |
| n-Pr | Br | H | H | Br | H | H |
| n-Pr | I | H | H | Br | H | H |
| n-Pr | Me | H | H | Br | H | H |
| n-Pr | $CF_3$ | H | H | Br | H | H |
| n-Pr | F | H | H | H | $J^2$ | H |
| n-Pr | Cl | H | H | H | $J^2$ | H |
| n-Pr | Br | H | H | H | $J^2$ | H |
| n-Pr | I | H | H | H | $J^2$ | H |
| n-Pr | Me | H | H | H | $J^2$ | H |
| n-Pr | $CF_3$ | H | H | H | $J^2$ | H |
| n-Pr | Et | H | H | H | $J^2$ | H |
| n-Pr | n-Pr | H | H | H | $J^2$ | H |
| n-Pr | F | Cl | H | H | H | $J^1$ |
| n-Pr | Cl | Cl | H | H | H | $J^1$ |
| n-Pr | Br | Cl | H | H | H | $J^1$ |
| n-Pr | I | Cl | H | H | H | $J^1$ |
| n-Pr | Me | Cl | H | H | H | $J^1$ |
| n-Pr | $CF_3$ | Cl | H | H | H | $J^1$ |
| n-Pr | Et | Cl | H | H | H | $J^1$ |
| n-Pr | n-Pr | Cl | H | H | H | $J^1$ |

REFERENTIAL EXAMPLE 1

(2-Phenylethyl)-3-amino-4-ethoxycarbonylpyrazole
Method A:
Step 1-A-1:
  Benzaldehyde (2-phenylethyl)hydrazone
  100 ml of aqueous 10% sodium hydroxide solution were added to an aqueous solution (50 ml) of 14.55 g of (2-phenylethyl)hydrazine sulfate, and 2.25 g of sodium hydroxide were added thereto and stirred at room temperature for one hour. The reaction solution was extracted with 250 ml of dichloromethane, dried over magnesium sulfate, concentrated under reduced pressure and dried. The resulting residue was dissolved in 100 ml of ethanol, and 5.55 g of benzaldehyde were added thereto and heated under reflux for 6 hours. This reaction solution was concentrated under reduced pressure and dried to obtain 11.38 g of a crude product of the intended compound as an yellow oil.
Step 1-A-2:
  Ethyl 3-[benzylidene(2-phenylethyl)hydrazino]-2-cyanoacrylate
  6.19 g of ethyl ethoxymethylenecyanoacetate were added to a toluene solution of 11.38 g of benzaldehyde(2-phenylethyl)-hydrazone and heated under reflux for 9 hours, and the solvent was distilled off under reduced pressure. The resulting residue was subjected to silica gel column chromatography (n-hexane—ethyl acetate=4:1→ethyl acetate) and then recrystallized from n-hexane—ethyl acetate to obtain 8.94 g of the intended compound as pale yellow crystals. m.p.: 128.9° to 132.9° C.
Step 1-A-3:
  1-(2-Phenylethyl)-3-amino-4-ethoxycarbonylpyrazole
  30 ml of ethanol and 4.6 ml of concentrated hydrochloric acid were added to 8.89 g of ethyl 3-[benzylidene(2-phenylethyl)hydrazino]-2-cyanoacrylate and heated under reflux for one hour. After cooled, the solvent was distilled off under reduced pressure. The resulting residue was dissolved in dichloromethane and washed with 20 ml of aqueous 10% sodium hydroxide solution. The aqueous phase was extracted with 100 ml of dichloromethane. The thus-obtained organic phases were combined, dried over magnesium sulfate and then concentrated under reduced pressure. The resulting residue was subjected to silica gel column chromatography (n-hexane—ethyl acetate=3:1→2:1→1:1) to obtain 5.61 g of the intended compound as colorless crystals. m.p.: 76.9° to 78.6° C.
Method B:
  250 ml of toluene and 0.1 ml of aqueous 12.5 M sodium hydroxide solution were added to a mixture of 15.69 g of ethyl 3-amino-4-pyrazolecarboxylate, 24.34 g of (2-bromoethyl)benzene, 2.54 g of Adogen 464 and 27.74 g of potassium carbonate, and heated under reflux for 2.5 hours. The reaction solution was washed with 200 ml of water and dried over magnesium sulfate, and the solvent was distilled off under reduced pressure. The resulting residue was subjected to silica gel column chromatography (n-hexane—ethyl acetate=2:1→1:1→1:2) to obtain 16.94 g of 1-(2-phenylethyl)-3-amino-4-ethoxycarbonylpyrazole as colorless crystals.

REFERENTIAL EXAMPLE 2

N-[1-(2-phenylethyl)-4-ethoxycarbonylpyrazol-3-yl]-N-[(2'-(N-triphenylmethyl-(1H-tetrazol-5-yl))biphenyl-4-yl) methyl]amine 2.1 ml of 1.5M lithium diisopropylamide/cyclohexane solution were added to THF solution (35 ml) containing 363 mg of 1-(2-phenylethyl)-3-amino-4-ethoxycarbonylpyrazole and 0.40 ml of 1,3-dimethyl-3,4,5,6-tetrahydro-2(1H)-pyrimidinone, while cooling with dry ice-acetone, and stirred at room temperature for 15 minutes. The mixture was again cooled with dry ice-acetone, and 10 ml of THF solution of 877 mg of 4-bromomethyl-2'-[N-triphenylmethyl-(1H-tetrazol-5-yl)]biphenyl were added thereto and stirred at room temperature for 5.5 hours. 10 ml of aqueous ammonium chloride solution was added to the reaction solution, THF was distilled off under reduced pressure, and the resultant was extracted with 50 ml of dichloromethane. The resulting extract was dried over magnesium sulfate and concentrated under reduced pressure. The residue thus obtained was subjected to silica gel column chromatography (n-hexane—ethyl acetate=3:1→2:1) to obtain 234 mg of the intended compound as a pale yellow, amorphous solid.

$^1$H NMR(CDCl$_3$, 60 MHz): δ1.22(t, J=7 Hz, 6H),
  3.18 (t, J=7 Hz, 2H), 3.8–4.1 (m, 6H),
  5.62 (t, J=6 Hz, 1H), 6.3–8.0 (m, 28H)

REFERENTIAL EXAMPLE 3

N-[1-(2-phenylethyl)-4-ethoxycarbonylpyrazol-3-yl]-N-[(2'-(N-triphenylmethyl-(1H-tetrazol-5-yl))biphenyl-4-yl) methyl]-n-propylamine 0.60 ml of 1.5M lithium diisopropylamide/cyclohexane solution were added to THF solution (20 ml) containing 223 mg of N-[1-(2-phenylethyl)-4-ethoxycarbonylpyrazol-3-yl)-N-[(2'-(N-triphenylmethyl-(1H-tetrazol-5-yl))biphenyl-4-yl)methyl]amine and 0.18 ml of 1,3-dimethyl-3,4,5,6-tetrahydro-2(1H)-pyrimidinone and stirred for 15 minutes, while cooling with dry ice-acetone. 0.15 ml of 1-iodopropane were added to the reaction solution and stirred overnight at room temperature. 10 ml of aqueous ammonia chloride solution were added thereto, THF was distilled off under reduced pressure, and the resultant was extracted with 50 ml of dichloromethane. The resulting extract was dried over magnesium sulfate and concentrated under reduced pressure. The thus-obtained residue was subjected to silica gel column chromatography (n-hexane—ethyl acetate=4:1→3:1) to obtain 91 mg of the intended compound as a pale yellow, amorphous solid.

$^1$H NMR(CDCl$_3$, 60 MHz): δ0.81 (t, J=7 Hz, 3H),
  1.1–1.8 (m, 2H),
  1.22 (t, J=7 Hz, 3H),
  2.8–3.3 (m, 4H),
  3.99 (t, J=7 Hz, 3H),
  4.15 (q, J=7 Hz, 2H),
  4.45 (s, 2H), 6.7–7.9 (m, 28H)

Best Mode for Carrying Out the Invention

SYNTHESIS EXAMPLE 1

N-(1-(2-phenylethyl)-4-ethoxycarbonyl-5-bromopyrazol-3-yl]-N-[(2'-(N-triphenylmethyl-(1H-tetrazol-5-yl))-biphenyl-4-yl)methyl]-n-propylamine 1.52 ml of 1.0M lithium bis(trimethylsilyl)amide/hexane solution were added to THF solution (20 ml) containing 395 mg of N-[1-(2-phenylethyl)-4-ethoxycarbonylpyrazol-3-yl]-N-[(2'-(N-triphenylmethyl-(1H-tetrazol-5-yl))biphenyl-4-yl)methyl]-n-propylamine and 0.18 ml of 1,3-dimethyl-3,4,5,6-tetrahydro-2(1H)-pyrimidinone, at room temperature, and then heated under reflux for 30 minutes. 0.60 ml of 1,2-dibromo-1,1,2,2-tetrafluoroethane was added thereto and heated under reflux for further 30 minutes. 10 ml of ammonium chloride were added to the reaction solution, THF was distilled off under reduced pressure, and the resultant was extracted with 150 ml of dichloromethane. The resulting extract was dried over magnesium sulfate and subjected to silica gel column chromatography (n-hexane—ethyl acetate=2:1) to obtain 363 mg of the intended compound as a pale red, amorphous solid.

$^1$H NMR(CDCl$_3$, 60 MHz): δ0.81(t, J=7 Hz, 3H),
1.2–1.8(m, 2H), 1.28(t, J=7 Hz, 3H),
2.8–3.2(m, 4H), 4.0–4.5(m, 4H),
4.32(s, 2H), 6.7–7.5(m, 27H),
7.7–7.9(m, 1H)
MS(FAB): 857(M+H)

SYNTHESIS EXAMPLE 2

N-[1-(2-phenylethyl)-4-ethoxycarbonyl-5-bromopyrazol-3-yl]-N-[(2'-(1H-tetrazol-5-yl)biphenyl-4-yl)methyl]-n-propylamine 356 mg of N-[1-(2-phenylethyl)-4-ethoxycarbonyl-5-bromopyrazol-3-yl]-N-[(2'-(N-triphenylmethyl-(1H-tetrazol-5-yl))biphenyl-4-yl)methyl]-n-propylamine were dissolved in 5 ml of ethanol and heated under reflux for 2 hours, and the solvent was distilled off under reduced pressure. The resulting residue was subjected to silica gel column chromatography (n-hexane—ethyl acetate=2:1→ethyl acetate) to obtain 224 mg of the intended compound as a pale yellow, amorphous solid.

$^1$H NMR(CDCl$_3$, 60 MHz): δ0.87(t, J=7 Hz, 3H),
1.1–1.7(m, 2H), 2.8–3.4(m, 4H),
4.31(s, 2H), 4.0–4.5(m, 4H),
6.8–7.5(m, 12H), 7.7–7.9(m, 1H)

SYNTHESIS EXAMPLE 3

N-[1-(2-phenylethyl)-4-carboxy-5-bromopyrazol-3-yl]-N-[(2'-(1H-tetrazol-5-yl)biphenyl-4-yl)methyl]-n-propylamine 5 ml of ethanol, 5 ml of water and 226 mg of potassium hydroxide were added to 206 mg of N-[1-(2-phenylethyl)-4-ethoxycarbonyl-5-bromopyrazol-3-yl]-N-[(2'-(1H-tetrazol-5-yl)-biphenyl-4-yl)methyl]-n-propylamine, and heated under reflux for 5 hours. Ethanol was distilled off under reduced pressure, and 10 ml of water were added to the reaction mixture, which was then made acidic with concentrated hydrochloric acid. The resultant was extracted with 50 ml of dichloromethane. After dried over magnesium sulfate, the extract was concentrated under reduced pressure and dried to obtain 185 mg of the intended compound as a pale yellow, amorphous solid.

$^1$H NMR(CDCl$_3$, 60 MHz): δ0.91(t, J=7 Hz, 3H),
1.1–1.8(m, 2H), 3.09(t, J=7 Hz, 4H),
4.07(s, 2H), 4.38(t, J=7 Hz, 2H),
6.90(s, 5H), 7.0–7.5(m, 12H),
7.7–7.9(m, 1H), 10.8–11.5(m, 2H)
MS(FAB): 586(M+H)

SYNTHESIS EXAMPLE 4

N-[1-(2-phenylethyl)-4-carboxy-5-bromopyrazol-3-yl]-N-[(2'-(1H-tetrazol-5-yl)biphenyl-4-yl)methyl]-n-propylamine dipotassium salt 102 mg of N-[1-(2-phenylethyl)-4-carboxy-5-bromopyrazol-3-yl]-N-[(2'-(1H-tetrazol-5-yl)biphenyl-4-yl)methyl]-n-propylamine were dissolved in 2 ml of methanol, and 3.5 ml of 0.1M potassium hydroxide/methanol solution were added thereto and stirred at room temperature for one hour. The resultant was concentrated under reduced pressure and dried to obtain 107 mg of the intended compound as an yellow, amorphous solid.
MS(FAB) : 662(M+H)

SYNTHESIS EXAMPLE 5

N-[1-(2-phenylethyl)-5-iodo-4-ethoxycarbonylpyrazol-3-yl]-N-[(2'-(N-triphenylmethyl-(1H-tetrazol-5-yl))-biphenyl-4-yl)methyl]-n-propylamine 0.18 ml of 1.6M n-butyl lithium/hexane solution were added to THF solution (10 ml) of 202 mg of N-[1-(2-phenylethyl)-5-bromo-4-ethoxycarbonylpyrazol-3-yl]-N-[(2'-(N-triphenylmethyl-(1H-tetrazol-5-yl))biphenyl-4-yl)methyl]-n-propylamine, while cooling with dry ice-acetone. After stirred for 2 hours, 667 mg of 1,2-diiodoethane were added thereto. After stirred for one hour, the mixture was then stirred at room temperature for further one hour. 10 ml of aqueous ammonium chloride solution were added to the reaction solution, THF was distilled off under reduced pressure, and the resultant was extracted with 50 ml of dichloromethane. After dried over magnesium sulfate, this was subjected to silica gel column chromatography (n-hexane—ethyl acetate=5:1) to obtain 84 mg of the intended compound as a pale red, amorphous solid.

$^1$H NMR(CDCl$_3$, 60 MHz): δ0.77(t, J=7 Hz, 3H),
1.31(t, J=7 Hz, 3H), 1.3–1.8(m, 2H),
2.8–3.2(m, 4H), 4.22(q, J=7 Hz, 2H),
4.28(t, J=7 Hz, 2H), 4.31(s, 2H),
6.8–7.5(m, 27H), 7.6–7.9(m, 1H)
MS(FAB): 904(M+H)

SYNTHESIS EXAMPLE 6

N-[1-(2-phenylethyl)-5-chloro-4-ethoxycarbonylpyrazol-3-yl]-N-[(2'-(N-triphenylmethyl-(1H-tetrazol-5-yl))-biphenyl-4-yl)methyl]-n-propylamine 0.24 ml of 1.6M n-butyl lithium/hexane solution were added to THF solution (10 ml) of 231 mg of N-[1-(2-phenylethyl)-5-bromo-4-ethoxycarbonylpyrazol-3-yl]-N-[(2'-(N-triphenylmethyl-(1H-tetrazol-5-yl))biphenyl-4-yl)methyl]-n-propylamine, while cooling with dry ice-acetone. After stirred for 30 minutes, 49 mg of N-chlorosuccinimide were added thereto and stirred for 30 minutes. 10 ml of aqueous ammonium chloride solution were added to the reaction solution, THF was distilled off under reduced pressure, and the resultant was extracted with 50 ml of dichloromethane. After dried over magnesium sulfate, the resultant was subjected to silica gel column chromatography (n-hexane—ethyl acetate=5:1) to obtain 159 mg of the intended compound as a pale yellow, amorphous solid.

$^1$H NMR(CDCl$_3$, 60 MHz): δ0.78(t, J=7 Hz, 3H),
1.27(t, J=7 Hz, 3H), 1.3–1.8(m, 2H),
2.99(t, J=7 Hz, 4H),
3.12(t, J=7 Hz, 4H),
4.23(q, J=7 Hz, 2H),
4.29(t, J=7 Hz, 2H), 4.36(s, 2H),
6.7–7.6(m, 27H), 7.8–8.0(m, 1H)
MS(FAB): 812(M+H)

SYNTHESIS EXAMPLE 7

N-[1-(2-phenylethyl)-5-(n-butylamino)-4-ethoxycarbonyl-pyrazol-3-yl]-N-[(2'-(N-triphenylmethyl-(1H-tetrazol-5-yl))biphenyl-4-yl)methyl]-n-propylamine 30 mg of reduced copper, 20 mg of copper(II) oxide, 83 mg of potassium carbonate and 5 ml of n-butylamine were added to 216 mg of N-[1-(2-phenylethyl)-5-bromo-4-ethoxycarbonylpyrazol-3-yl]-N-[(2'-(N-triphenylmethyl-(1H-tetrazol-5-yl))biphenyl-4-yl)methyl]-n-propylamine, and heated under reflux for 14 hours. The reaction solution was filtered through Celite, and the filtrate was concentrated under reduced pressure. The residue was subjected to silica gel column chromatography (n-hexane—ethyl acetate=7:1) to obtain 92 mg of the intended compound as a pale yellow, amorphous solid.

$^1$H NMR(CDCl$_3$, 60 MHz): δ0.75(t, J=7 Hz, 3H),
0.89(t, J=7 Hz, 3H),
1.21(t, J=7 Hz, 3H), 1.1–1.8(m, 6H),
2.99(t, J=7 Hz, 6H),
4.04(t, J=7 Hz, 2H),
4.17(q, J=7 Hz, 2H),
4.31(s, 2H), 5.91(t, J=7 Hz, 1H),
6.7–7.5(m, 27H), 7.6–7.9(m, 1H)

SYNTHESIS EXAMPLE 8

N-[1-(2-phenylethyl)-5-(2-methylphenyl)-4-ethoxycarbonylpyrazol-3-yl]-N-[(2'-(N-triphenylmethyl-(1H-tetrazol-5-yl))biphenyl-4-yl)methyl]-n-propylamine 0.23 ml of 1.6M n-butyl lithium/hexane solution were dropwise added to THF solution (5 ml) containing 208 mg of N-[1-(2-phenylethyl)-5-bromo-4-ethoxycarbonylpyrazol-3-yl]-N-[(2'-(N-triphenylmethyl-(1H-tetrazol-5-yl))biphenyl-4-yl)methyl]-n-propylamine and 0.04 ml of 1,3-dimethyl-3,4,5,6-tetrahydro-2(1H)-pyrimidinone and stirred for 10 minutes, while cooling with dry ice-acetone. 0.74 ml of 0.5M zinc chloride/THF solution were added thereto and stirred for 30 minutes at room temperature. Then, THF solution (5 ml) containing 83 mg of m-iodotoluene and 36 mg of tetrakis(triphenylphosphine) palladium(0) were added thereto and stirred for 28 hours at 60° C. 10 ml of ammonium chloride were added to the reaction solution, THF was distilled off under reduced pressure, and the resultant was extracted with 50 ml of dichloromethane. After dried over magnesium sulfate, the solvent was distilled off under reduced pressure. The resulting residue was subjected to silica gel column chromatography (n-hexane—ethyl acetate=5:1) to obtain 171 mg of the intended compound as a pale yellow, amorphous solid.

$^1$H NMR(CDCl$_3$, 60 MHz): δ0.82(t, J=7 Hz, 6H), 1.3–1.8 (m, 2H),
2.22(s, 3H), 2.96(t, J=7 Hz, 2H),
3.20(t, J=7 Hz, 2H), 3.7–4.1(m, 4H),
4.44(s, 2H), 6.3–7.5(m, 31H),
7.7–7.9(m, 1H)
MS(FAB): 868(M+H)

SYNTHESIS EXAMPLES 9 TO 21

In the same manner as in Synthesis Example 8, the following compounds were synthesized.

| No.* | R$^3$ | $^1$H NMR, MS |
|---|---|---|
| 9 | 2-methylphenyl (CH$_3$) | MS(FAB): 868(M+H) |
| 10 | 4-methylphenyl (CH$_3$) | $^1$H NMR(CDCl$_3$, 60MHz): δ 0.82(t, J=7Hz, 3H), 0.85(t, J=7Hz, 3H), 1.3–1.9(m, 2H), 2.22(s, 3H), 2.95(t, J=7Hz, 2H), 3.18(t, J=7Hz, 2H), 3.87 (t, J=7Hz, 2H), 3.90(q, J=7Hz, 2H), 4.42(s, 2H), 6.5–7.4(m, 31H), 7.6–7.9 (m, 1H)<br>MS(FAB): 868(M+H) |
| 11 | phenyl | $^1$H NMR(CDCl$_3$, 60MHz): δ 0.80(t, J=7Hz, 3H), 0.84(t, J=7Hz, 3H), 1.3–1.9(m, 2H), 2.97(t, J=7Hz, 2H), 3.87(t, J=7Hz, 2H), 3.88(q, J=7Hz, 2H), 4.45(s, 2H), 6.5–7.5(m, 32H), 7.7–8.0(m, 1H)<br>MS(FAB): 854(M+H) |
| 12 | 2-methoxyphenyl (CH$_3$O) | $^1$H NMR(CDCl$_3$, 60MHz): δ 0.81(t, J=7H, 6H), 1.2–1.8(m, 2H), 2.7–3.4(m, 4H), 366(s, 3H), 3.89(q, J=7Hz, 2H), 3.90(t, J=7Hz, 2H), 4.46(s, 2H), 6.4–7.5(m, 31H), 7.6–7.9(m, 1H)<br>MS(FAB): 884(M+H) |

-continued

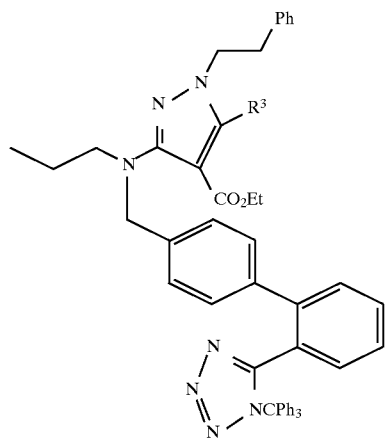

| No.* | R³ | ¹H NMR, MS |
|---|---|---|
| 13 | 3-methoxyphenyl | ¹H NMR(CDCl₃, 60MHz): δ 0.83(t, J=7Hz, 6H), 1.3–1.9(m, 2H), 2.97 (t, J=7Hz, 2H), 3.21(t, J=7Hz, 2H), 3.67(s, 3H), 3.90(q, J=7Hz, 2H), 3.90 (t, J=7Hz, 2H), 4.45(s, 2H), 6.2–7.5(m, 31H), 7.6–7.9(m, 1H) MS(FAB): 884(M+H) |
| 14 | 4-methoxyphenyl | ¹H NMR(CDCl₃, 60MHz): δ 0.72(t, J=7Hz, 3H), 0.88(t, J=7Hz, 3H), 1.3– 1.9(m, 2H), 2.95(t, J=7Hz, 2H), 3.21(t, J=7Hz, 2H), 3.78(s, 3H), 3.88 (t, J=7Hz, 2H), 3.93(q, J=7Hz, 2H), 4.44(s, 2H), 6.6–7.5(m, 31H), 7.6–8.0 (m, 1H) MS(FAB): 884(M+H) |
| 15 | 2-chlorophenyl | ¹H NMR(CDCl₃, 60MHz): δ 0.77(t, J=7Hz, 3H), 0.82(t, J=7Hz, 3H), 1.3– 1.9(m, 2H), 2.8–3.4(m, 4H), 3.87(q, J=7Hz, 2H), 4.06(t, J=7Hz, 2H), 4.46(s, 2H), 6.1–8.0(m, 32H) |
| 16 | 3-chlorophenyl | ¹H NMR(CDCl₃, 60MHz): δ 0.80(t, J=7Hz, 3H), 0.81(t, J=7Hz, 3H), 1.3– 1.9(m, 2H), 2.94(t, J=7Hz, 2H), 3.20(t, J=7Hz, 2H), 3.83(t, J=7Hz, 2H), 3.87(q, J=7Hz, 2H), 4.43(s, 2H), 6.4–7.5(m, 31H), 7.6–7.9(m, 1H) |
| 17 | 6-bromopyridin-2-yl | ¹H NMR(CDCl₃, 60MHz): δ 0.80(t, J=7Hz, 3H), 0.90(t, J=7Hz, 3H), 1.3– 1.8(m, 2H), 2.8–3.4(m, 4H), 3.93(q, J=7Hz, 2H), 4.02(t, J=7Hz, 2H), 4.39(s, 2H), 6.4–7.5(m, 30H), 7.7–7.9(m, 1H) MS(FAB): 933(M+H) |
| 18 | 2-thienyl | ¹H NMR(CDCl₃, 60MHz): δ 0.81(t, J=7Hz, 3H), 0.92(t, J=7Hz, 3H), 1.3– 1.8(m, 2H), 2.99(t, J=7Hz, 2H), 3.19(t, J=7Hz, 2H), 3.98(q, J=7Hz, 2H), 3.99(t, J=7Hz, 2H), 4.46(s, 2H), 6.3–7.5(m, 30H), 7.6–8.0(m, 1H) MS(FAB): 869(M+H) |
| 19 | benzyl | ¹H NMR(CDCl₃, 60MHz): δ 0.80(t, J=7Hz, 3H), 1.15(t, J=7Hz, 3H), 1.3– 1.8(m, 2H), 2.82(t, J=7Hz, 2H), 3.12(t, J=7Hz, 2H), 3.95(s, 2H), 3.95 (t, J=7Hz, 2H), 4.15(q, J=7Hz, 2H), 4.38(s, 2H), 6.6–7.4(m, 32H), 7.5–7.9 (m, 1H) |
| 20 | allyl | ¹H NMR(CDCl₃, 60MHz): δ 0.77(t, J=7Hz, 3H), 2.24(t, J=7Hz, 3H), 1.2– 1.8(m, 2H), 2.98(t, J=7Hz, 2H), 3.10(t, J=7Hz, 2H), 3.34(d, J=6Hz, 2H), 4.02(t, J=7Hz, 2H), 4.18(q, J=7Hz, 2H), 4.34(s, 2H), 4.6–5.1(m, 2H), 5.3–5.8(m, 1H), 6.8–7.5(m, 27H), 7.6–7.9(m, 1H) MS(FAB): 818(M+H) |

-continued

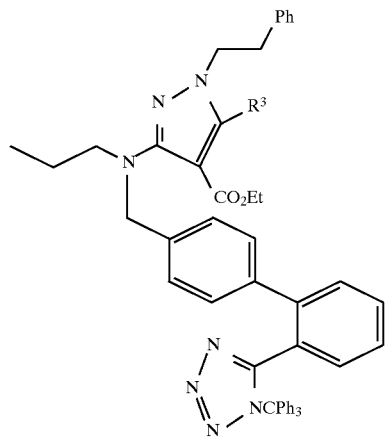

| No.* | R³ | ¹H NMR, MS |
|---|---|---|
| 21 | (acetylphenyl group) | ¹H NMR(CDCl₃, 60MHz): δ 0.67(t, J=7Hz, 3H), 0.80(t, J=7Hz, 3H), 1.1–1.8(m, 2H), 3.10(t, J=7Hz, 2H), 3.69(q, J=7Hz, 2H), 4.10(t, J=7Hz, 4H), 4.50(s, 2H), 6.8–7.5(m, 33H)<br>MS(FAB): 882(M+H) |

*Synthesis Example No.

SYNTHESIS EXAMPLES 22 TO 37

The he following compounds were synthesized by deprotecting the corresponding compounds in the same manner as in Synthesis Example 2.

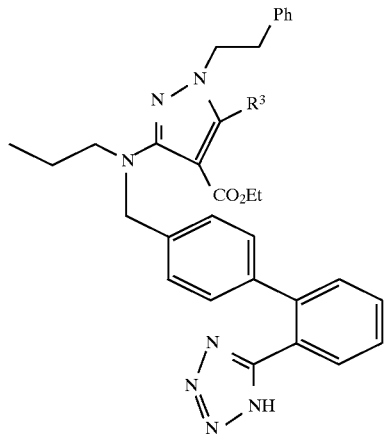

| No.* | R³ | ¹H NMR, MS |
|---|---|---|
| 22 | Cl | ¹H NMR(CDCl₃, 60MHz): δ 0.82(t, J=7Hz, 3H), 1.27(t, J=7Hz, 3H), 1.3–1.8(m, 2H), 2.99(t, J=7Hz, 2H), 3.12(t, J=7Hz, 2H), 4.18(t, J=7Hz, 2H), 4.19(q, J=7Hz, 2H), 4.36(s, 2H), 6.7–7.6(m, 12H), 7.8–8.1(m, 1H)<br>MS(EI): 288(9%), 334(17%), 526(7%), 596(M⁺, 1%) |
| 23 | I | ¹H NMR(CDCl₃, 60MHz): δ 0.83(t, J=7Hz, 3H), 1.32(t, J=7Hz, 3H), 1.3–1.8(m, 2H), 2.98(t, J=7Hz, 2H), 3.12(t, J=7Hz, 2H), 4.21(q, J=7Hz, 2H), 4.28(t, J=7Hz, 2H), 4.37(s, 2H), 6.7–7.6(m, 12H), 7.8–8.0(m, 1H)<br>MS(EI): 380(48%), 426(66%), 618(77%), 661(M⁺, 8%) |

-continued

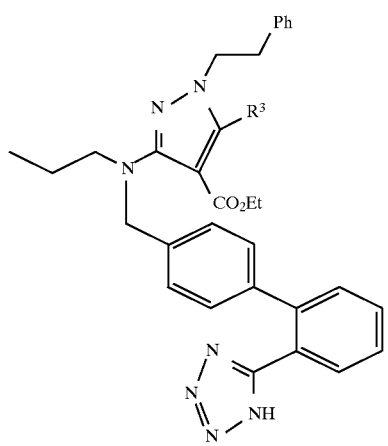

| No.* | R³ | ¹H NMR, MS |
|---|---|---|
| 24 | CH₃ (2-methylphenyl) | ¹H NMR(CDCl₃, 60MHz): δ 0.71(t, J=7Hz, 3H), 0.89(t, J=7Hz, 3H), 1.3–1.8(m, 2H), 1.91(s, 3H), 2.93(t, J=7Hz, 2H), 3.25(t, J=7Hz, 2H), 3.77 (t, J=7Hz, 2H), 3.95(q, J=7Hz, 2H), 4.51(s, 2H), 6.75(d, J=8Hz, 12H), 7.20 (s, 9H), 7.49(d, J=8Hz, 4H)<br>MS(ET): 344(16%), 391(37%), 508(4%), 625(M⁺, 0.4%) |
| 25 | CH₃ (3-methylphenyl) | ¹H NMR(CDCl₃, 60MHz): δ 0.77(t, J=7Hz, 3H), 0.88(t, J=7Hz, 3H), 1.3–1.9(m, 2H), 2.24(s, 3H), 2.94(t, J=7Hz, 2H), 3.24(t, J=7Hz, 2H), 3.83 (q, J=7Hz, 2H), 3.86(t, J=7Hz, 2H), 4.45(s, 2H), 6.3–7.5(m, 16H), 7.7–8.0 (m, 1H), 9.2–9.7(m, 1H)<br>MS(FAB): 626(M+H) |
| 26 | CH₃ (4-methylphenyl) | ¹H NMR(CDCl₃, 60MHz): δ 0.80(t, J=7Hz, 3H), 0.85(t, J=7Hz, 3H), 1.3–1.9(m, 2H), 2.30(s, 3H), 2.89(t, J=7Hz, 2H), 3.17(t, J=7Hz, 2H), 3.83 (q, J=7Hz, 2H), 3.86(t, J=7Hz, 2H), 4.41(s, 2H), 6.4–7.6(m, 16H), 7.8–8.0 (m, 1H)<br>MS(EI): 344(4%), 391(5%), 582(3%), 625(M⁺, 1%) |
| 27 | phenyl | ¹H NMR(CDCl₃, 60MHz): δ 0.76(t, J=7Hz, 3H), 0.88(t, J=7Hz, 3H), 1.3–1.9(m, 2H), 2.91(t, J=7Hz, 2H), 3.22(t, J=7Hz, 2H), 3.82(q, J=7Hz, 2H), 3.87(t, J=7Hz, 2H), 4.47(s, 2H), 6.5–7.6(m, 17H), 7.8–8.1(m, 1H) |
| 28 | CH₃O (2-methoxyphenyl) | ¹H NMR(CDCl₃, 60MHz): δ 0.75(t, J=7Hz, 3H), 0.84(t, J=7Hz, 3H), 1.2–1.8(m, 2H), 2.7–3.3(m, 4H), 3.65(s, 3H), 3.82(q, J=7Hz, 2H), 4.04(t, J=7Hz, 2H), 4.42(s, 2H), 6.4–7.6(m, 17H), 7.8–8.1(m, 1H)<br>MS(EI): 360(24%), 407(100%), 598(4%), 642(M⁺+H, 3%) |
| 29 | OCH₃ (3-methoxyphenyl) | MS(EI): 361(7%), 407(24%), 598(2%), 641(M⁺, 1%) |
| 30 | OCH₃ (4-methoxyphenyl) | ¹H NMR(CDCl₃, 60MHz): δ 0.86(t, J=7Hz, 3H), 0.88(t, J=7Hz, 3H), 1.2–1.8(m, 2H), 2.91(t, J=7Hz, 2H), 3.22(t, J=7Hz, 2H), 3.27(s, 3H), 3.86 (q, J=7Hz, 2H), 3.88(t, J=7Hz, 2H), 4.46(s, 2H), 6.4–7.5(m, 16H), 7.8–8.0 (m, 1H)<br>MS(EI): 360(3%), 407(10%), 598(0.7%), 641(M⁺, 0.5%) |
| 31 | Cl (2-chlorophenyl) | ¹H NMR(CDCl₃, 60MHz): δ 0.74(t, J=7Hz, 3H), 0.87(t, J=7Hz, 3H), 1.3–1.9(m, 2H), 2.99(t, J=7Hz, 2H), 3.25(t, J=7Hz, 2H), 3.83(q, J=7Hz, 2H), 4.06(t, J=7Hz, 2H), 4.49(s, 2H), 6.2–7.6(m, 16H), 7.8–8.1(m, 1H) |

-continued

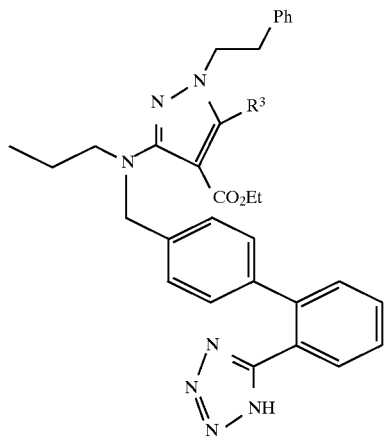

| No.* | R³ | ¹H NMR, MS |
|---|---|---|
| 32 | 3-chlorophenyl (CH₂-) | ¹H NMR(CDCl₃, 60MHz): δ 0.79(t, J=7Hz, 3H), 0.91(t, J=7Hz, 3H), 1.3–1.9(m, 2H), 2.93(t, J=7Hz, 2H), 3.25(t, J=7Hz, 2H), 3.84(q, J=7Hz, 2H), 3.87(t, J=7Hz, 2H), 4.48(s, 2H), 6.4–6.7(m, 4H), 6.8–7.5(m, 12H), 7.7–8.0(m, 1H)<br>MS(FAB): 646(M+H) |
| 33 | 6-bromopyridin-2-yl (CH₂-) | ¹H NMR(CDCl₃, 60MHz): δ 0.89(t, J=7Hz, 6H), 1.3–1.9(m, 2H), 2.98 (t, J=7Hz, 2H), 3.22(t, J=7Hz, 2H), 3.89(q, J=7Hz, 2H), 4.00(t, J=7Hz, 2H), 4.45(s, 2H), 6.4–7.6(m, 15H), 7.8–8.1(m, 1H)<br>MS(EI): 411(5%), 456(10%), 647(1%), 690(M⁺, 0.2%) |
| 34 | thiophen-2-yl (CH₂-) | ¹H NMR(CDCl₃, 60MHz): δ 0.87(t, J=7Hz, 3H), 0.90(t, J=7Hz, 3H), 1.3–1.9(m, 2H), 2.97(t, J=7Hz, 2H), 3.21(t, J=7Hz, 2H), 3.91(q, J=7Hz, 2H), 3.97(t, J=7Hz, 2H), 4.47(s, 2H), 6.3–7.6(m, 15H), 7.8–8.1(m, 1H), 8.3–8.8(m, 1H)<br>MS(EI): 336(34%), 383(37%), 531(14%), 574(14%), 617(M⁺, 0.8%) |
| 35 | PhCH₂CH₂- | ¹H NMR(CDCl₃, 60MHz): δ 0.83(t, J=7Hz, 3H), 1.13(t, J=7Hz, 3H), 1.3–1.8(m, 2H), 2.78(t, J=7Hz, 2H), 3.14(t, J=7Hz, 2H), 3.95(s, 2H), 3.95 (t, J=7Hz, 2H), 4.11(q, J=7Hz, 2H), 4.36(s, 2H), 6.7–7.6(m, 17H), 7.8–8.1 (m, 1H), 9.9–10.6(m, 1H)<br>MS(EI): 316(8%), 344(13%), 390(12%), 582(5%), 625(M⁺, 3%) |
| 36 | CH₂=CHCH₂CH₂- | ¹H NMR(CDCl₃, 60MHz): δ 0.72(t, J=7Hz, 3H), 1.24(t, J=7Hz, 3H), 1.2–1.8(m, 2H), 2.8–3.5(m, 6H), 4.01(t, J=7Hz, 2H), 4.17(q, J=7Hz, 2H), 4.35(s, 2H), 4.6–5.1(m, 2), 5.3–5.9(m, 1H), 6.8–7.6(m, 12H), 7.8–8.1(m, 1H), 9.1–9.6(m, 1H) |
| 37 | PhC(O)CH₂- | ¹H NMR(CDCl₃, 60MHz): δ 0.65(t, J=7Hz, 3H), 0.89(J=7Hz, 3H), 1.3–1.9(m, 2H), 3.12(t, J=7Hz, 2H), 3.65(q, J=7Hz, 2H), 4.09(t, J=7Hz, 4H), 4.51(s, 2H), 6.8–7.5(m, 18H), 7.8–8.1(m, 1H)<br>MS(FAB): 640(M+H) |
| 38 | —NH—ⁿPr | ¹H NMR(CDCl₃, 60MHz): δ 0.6–1.1(m, 6H), 1.2–1.8(m, 6H), 1.26(t, J=7Hz, 3H), 2.7–3.2(m, 6H), 3.97(t, J=7Hz, 2H), 4.16(q, J=7Hz, 4H), 4.23 (s, 2H), 6.7–7.5(m, 12H), 7.7–8.0(m, 1H)<br>MS(EI): 325(5%), 372(2%), 517(4%), 563(0.8%), 606(M⁺, 1%) |

*Synthesis Example No.

SYNTHESIS EXAMPLES 39 TO 55

The following compounds were synthesized by hydrolyzing the corresponding esters in the same manner as in Synthesis Example 3.

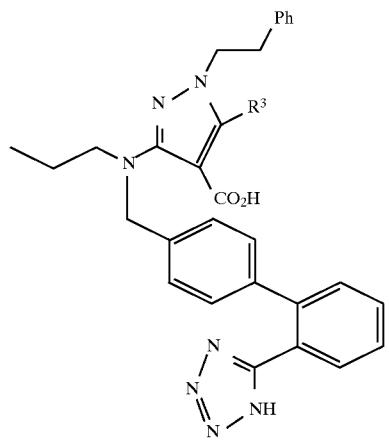

| No.* | R³ | ¹H NMR, MS |
|---|---|---|
| 39 | Cl | ¹H NMR(CDCl₃, 60MHz): δ 0.88(t, J=7Hz, 3H), 1.3–1.8(m, 2H), 3.08 (t, J=7Hz, 4H), 4.08(s, 2H), 4.33(t, J=7Hz, 2H), 6.9–7.6(m, 12H), 7.7–8.0 (m, 1H), 9.4–10.3(m, 2H) MS(EI): 426(0.9%), 454(0.8%), 468(1%), 497(M⁺−CO₂, 2%) |
| 40 | I | ¹H NMR(CDCl₃, 60MHz): δ 0.80(t, J=7Hz, 3H), 1.3–1.7(m, 2H), 3.13 (t, J=7Hz, 4H), 4.10(s, 2H), 4.45(t, J=7Hz, 2H), 6.9–7.6(m, 12H), 7.7–8.1 (m, 1H), 9.5–10.2(m, 2H) MS(FAB): 598(M+H) |
| 41 | 2-CH₃-phenyl | ¹H NMR(CDCl₃, 60MHz): δ 0.98(t, J=7Hz, 3H), 1.3–2.0(m, 2H), 1.75 (s, 3H), 2.9–3.5(m, 4H), 3.94(t, J=7Hz, 2H), 4.18(s, 2H), 6.4–7.6(m, 16H), 7.8–8.0(m, 1H), 9.4–10.1(m, 2H) MS(EI): 105(100%), 318(2%), 509(2%), 553(M⁺−CO₂, 7%) |
| 42 | 3-CH₃-phenyl | ¹H NMR(CDCl₃, 60MHz): δ 0.95(t, J=7Hz, 3H), 1.3–1.8(m, 2H), 2.19 (s, 3H), 2.05(t, J=7Hz, 2H), 2.16(t, J=7Hz, 2H), 4.15(t, J=7Hz, 2H), 4.17 (s, 2H), 6.4–7.6(m, 16H), 7.7–8.0(m, 1H), 11.4–12.1(m, 2H) |
| 43 | 4-CH₃-phenyl | ¹H NMR(CDCl₃, 60MHz): δ 0.94(t, J=7Hz, 3H), 1.3–1.8(m, 2H), 2.31 (s, 3H), 3.04(t, J=7Hz, 2H), 3.25(t, J=7Hz, 2H), 4.15(t, J=7Hz, 2H), 4.20 (s, 2H), 6.6–7.6(m, 16H), 7.8–8.1(m, 1H), 11.0–11.5(m, 2H) MS(EI): 105(43%), 510(0.7%), 524(0.9%), 553(M⁺−CO₂, 7%) |
| 44 | phenyl | ¹H NMR(CDCl₃, 60MHz): δ 0.95(t, J=7Hz, 3H), 1.3–1.9(m, 2H), 2.9–3.5(m, 4H), 4.15(t, J=7Hz, 2H), 4.16(s, 2H), 6.7–7.7(m, 17H), 7.8–8.1(m, 1H), 9.3–9.9(m, 2H) |
| 45 | 2-CH₃O-phenyl | ¹H NMR(CDCl₃, 60MHz): δ 0.93(t, J=7Hz, 3H), 1.3–1.9(m, 2H), 2.8–3.4(m, 4H), 3.57(s, 3H), 4.07(t, J=7Hz, 2H), 4.14(s, 2H), 6.65(d, J=8Hz, 4H), 7.10(s, 9H), 7.49(d, J=8Hz, 4H), 11.2–11.7(m, 2H) MS(FAB): 614(M+H) |
| 46 | 3-OCH₃-phenyl | ¹H NMR(CDCl₃, 60MHz): δ 0.92(t, J=7Hz, 3H), 1.3–1.8(m, 2H), 3.03 (t, J=7Hz, 2H), 3.17(t, J=7Hz, 2H), 3.61(s, 3H), 4.16(s, 2H), 4.16(t, J=7Hz, 2H), 6.3–8.0(m, 17H), 11.3–11.8(m, 2H) MS(EI): 105(61%), 421(4%), 525(0.3%), 569(M⁺−CO₂, 0.2%) |
| 47 | 4-OCH₃-phenyl | ¹H NMR(CDCl₃, 60MHz): δ 0.96(t, J=7Hz, 3H), 1.3–1.8(m, 2H), 3.06 (t, J=7Hz, 2H), 3.23(t, J=7Hz, 2H), 3.76(s, 3H), 4.18(s, 2H), 4.19(t, J=7Hz, 2H), 6.6–7.6(m, 16H), 7.7–8.0(m, 1H), 10.8–11.6(m, 2H) |

-continued

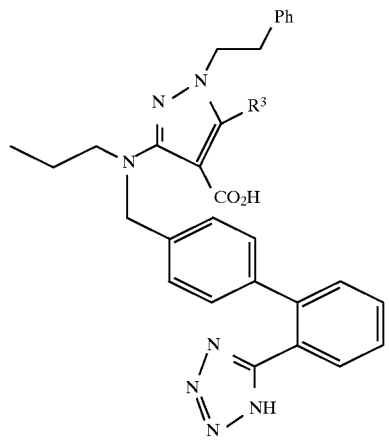

| No.* | R³ | ¹H NMR, MS |
|---|---|---|
| 48 | 2-chlorophenyl | MS(EI): 105(100%), 338(0.7%), 544(1%), 573($M^+$-$CO_2$, 4%) |
| 49 | 3-chlorophenyl | ¹H NMR(CDCl₃, 60MHz): δ 0.94(t, J=7Hz, 3H), 1.2–1.9(m, 2H), 2.8–3.4(m, 4H), 3.10(t, J=7Hz, 2H), 3.18(s, 2H), 6.5–7.5(m, 16H), 7.7–8.0(m, 1H), 11.0–11.6(m, 2H)<br>MS(FAB): 618(M+H) |
| 50 | 6-bromo-2-pyridyl | ¹H NMR(CDCl₃, 60MHz): δ 0.92(t, J=7Hz, 3H), 1.2–1.9(m, 2H), 3.05 (t, J=7Hz, 2H), 3.18(t, J=7Hz, 2H), 4.13(s, 2H), 4.50(t, J=7Hz, 2H), 6.6–7.5(m, 15H), 7.7–7.9(m, 1H), 9.3–10.0(m, 2H) |
| 51 | 2-thienyl | ¹H NMR(CDCl₃, 60MHz): δ 0.90(t, J=7Hz, 3H), 1.3–1.8(m, 2H), 3.05 (t, J=7Hz, 2H), 3.16(t, J=7Hz, 2H), 4.14(s, 2H), 4.25(t, J=7Hz, 2H), 6.6–7.6(m, 15H), 7.7–8.0(m, 1H), 10.8–11.5(m, 2H)<br>MS(FAB): 590(M+H) |
| 52 | benzyl | ¹H NMR(CDCl₃, 60MHz): δ 0.91(t, J=7Hz, 3H), 1.2–1.8(m, 2H), 2.83 (t, J=7Hz, 2H), 3.15(t, J=7Hz, 2H), 4.04(t, J=7Hz, 2H), 4.10(s, 2H), 6.8–7.5(m, 17H), 7.7–8.0(m, 1H), 11.0–11.6(m, 2H)<br>MS(FAB): 598(M+H) |
| 53 | allyl | ¹H NMR(CDCl₃, 60MHz): δ 0.90(t, J=7Hz, 3H), 1.3–1.9(m, 2H), 3.08 (t, J=7Hz, 2H), 3.11(t, J=7Hz, 2H), 3.42(d, J=6Hz, 2H), 4.08(s, 2H), 4.18 (t, J=7Hz, 2H), 4.5–5.1(m, 2H), 5.3–6.0(m, 1H), 6.8–7.6(m, 12H), 7.7–8.0(m, 1H), 10.1–10.7(m, 2H)<br>MS(FAB): 548(M+H) |
| 54 | benzoylmethyl | ¹H NMR(CDCl₃, 60MHz): δ 0.90(t, J=7Hz, 3H), 1.10(t, J=7Hz, 3H), 1.2–1.9(m, 2H), 3.05(t, J=7Hz, 2H), 4.1–4.4(m, 4H), 4.20(s, 2H), 6.9–7.5 (m, 18H)<br>MS(FAB): 612(M+H) |
| 55 | —NH—ⁿPr | ¹H NMR(CDCl₃+10%CD₃OD, 60MHz): δ 0.90(t, J=7Hz, 3H), 1.0–1.7 (m, 6H), 2.92(t, J=7Hz, 2H), 3.07(t, J=7Hz, 2H), 4.09(t, J=7Hz, 2H), 4.23 (s, 2H), 6.7–7.9(m, 13H)<br>MS(EI): 105(84%), 299(0.8%), 534($M^+$-$CO_2$, 9%) |

*Synthesis Example No.

SYNTHESIS EXAMPLES 56 TO 71

The following compounds were synthesized by converting corresponding compounds into their potassium salts in the same manner as in Synthesis Example 4.

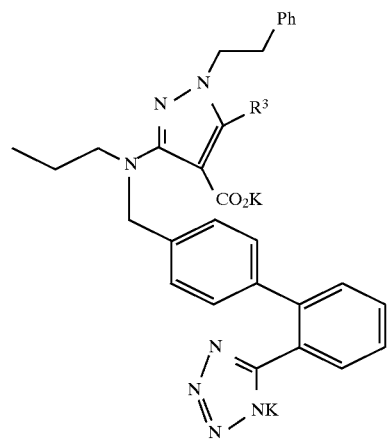

| No.* | R³ | FAB-MS |
|---|---|---|
| 56 | Cl | MS(FAB): 618(M+H) |
| 57 | I | MS(FAB): 710(M+H) |
| 58 | 2-CH₃-C₆H₄ | MS(FAB): 630(M−CO₂+H) |
| 59 | 3-CH₃-C₆H₄ | MS(FAB): 674(M+H) |
| 60 | 4-CH₃-C₆H₄ | MS(FAB): 674(M+H) |
| 61 | C₆H₅ | MS(FAB): 616(M−CO₂+H) |
| 62 | 2-CH₃O-C₆H₄ | MS(FAB): 690(M+H) |
| 63 | 3-CH₃O-C₆H₄ | MS(FAB): 690(M+H) |
| 64 | 4-CH₃O-C₆H₄ | MS(FAB): 690(M+H) |

| No.* | R³ | FAB-MS |
|---|---|---|
| 65 | 2-Cl-C₆H₄ | MS(FAB): 650(M−CO₂+H) |
| 66 | 3-Cl-C₆H₄ | MS(FAB): 694(M+H) |
| 67 | 2-Br-pyridyl | MS(FAB): 739(M+H) |
| 68 | 2-thienyl | MS(FAB): 666(M+H) |
| 69 | -CH₂CH₂-C₆H₅ | MS(FAB): 674(M+H) |
| 70 | -CH₂CH=CH₂ (propenyl) | MS(FAB): 624(M+H) |
| 71 | -C(O)-C₆H₅ (acetylphenyl) | MS(FAB): 688(M+H) |
| 72 | —NH—ⁿPr | MS(FAB): 611(M−CO₂+H) |

*Synthesis Example No.

EXPERIMENTAL EXAMPLE 1

Test for Antagonistic Effect against Angiotensin:

A rabbit was sacrificed while anesthetized with pentobarbital, and immediately its thoracic aorta was removed. This was cut into a ring specimen, kept at 37° C. and hung in a nutrient liquid (Krebs-Henseleit solution) aerated with a mixed gas comprising 95% oxygen and 5% carbon dioxide, whereupon its isometric contraction was measured. The specimen was equilibrated for one hour, with replacement of the nutrient liquid every 20 minutes, and thereafter angiotensin II (AngII: $10^{-8}$M) was applied thereto to cause its contraction. To evaluate the effect of the compounds of the present invention, the compound to be tested ($10^{-7}$M or $10^{-8}$M) was applied as pre-treatment to the specimen in 20 minutes before the fourth application of AngII thereto, the percentage of inhibiting the contraction caused by AngII was obtained on the basis of the third contraction caused by AngII of being 100%. The percentage was corrected, using dimethylsulfoxide (DMSO).

TABLE 6

| Compound of the Invention (as the number of Synthesis Example) | Percentage of Inhibition of Contraction (%) | |
|---|---|---|
| | $1 \times 10^{-7}$ M | $1 \times 10^{-8}$ M |
| 4 | 85 | 40 |
| 56 | 84 | 51 |
| 61 | 77 | 34 |
| 64 | 92 | 29 |
| 67 | 35 | 13 |
| 68 | 35 | 18 |
| 71 | 36 | 14 |
| 72 | 15 | 7 |

EXPERIMENTAL EXAMPLE 2

Test for Hypotensive Effect

The compounds of the present invention to be tested were dissolved in a physiological saline solution and was orally administered to a spontaneous hypertensive male rat (10-week age). The blood pressure of the rat was measured, via a pressure transducer through the catheter that had previously been introduced into its aorta from its femoral artery. The variation in the blood pressure was observed from before the application of the compound to 20 hours after the application thereof.

The following table shows the dose of the compound administered, the largest percentage of the depression of the blood pressure and the time after the administration at which the largest percentage was obtained.

TABLE 7

| Compound of the Invention (as the number of Synthesis Example) | Dose (mg/kg) | Largest Percentage of Blood Pressure Depression | Time (hr) |
|---|---|---|---|
| 4 | 30 | 29.6 | 10 |

EXPERIMENTAL EXAMPLE 3

Test for Inhibition of Binding to Angiotensin II ($AT_2$) Receptor:

The effect of the compounds of the present invention for inhibiting the binding activity of Angiotensin II (AngII) to the bovine brain receptor were tested, according to the method by J. P. Bennett, Jr. et al. [J. Biol. Chem., 251, 7423–7430 (1976)].

$10^{-6}$M of the compound of the present invention to be tested was added to an aqueous solution containing a predetermined amount of a bovine brain specimen and 0.1 nM of $^{125}$I-AngII and incubated at 37° C. for 30 minutes. The resulting solution was separated through a glass fiber filter to terminate the reaction. The radioactivity bonded to the filter was quantified by a γ-counter.

TABLE 8

| Compound of the Invention (as the number of Synthesis Example) | Percentage of Inhibition (%) |
|---|---|
| 4 | 55.1 |

[Formulation Examples]
FORMULATION EXAMPLE 1:
Tablets:

| | |
|---|---|
| Compound (produced in Synthesis Example 4) | 10 g |
| Lactose | 260 g |
| Crystal cellulose powder | 600 g |
| Corn Starch | 350 g |
| Hydroxypropyl cellulose | 100 g |
| CMC-Ca | 150 g |
| Magnesium stearate | 30 g |
| Total | 1,500 g |

The above-mentioned components were mixed by a usual method and then tabletted to produce 10,000 sugar-coated tablets each containing one mg of the active ingredient.

FORMULATION EXAMPLE 2

Capsules:

| | |
|---|---|
| Compound (produced in Synthesis Example 4) | 10 g |
| Lactose | 440 g |
| Crystal cellulose powder | 1,000 g |
| Magnesium stearate | 50 g |
| Total | 1,500 g |

The above-mentioned components were mixed by a usual method and then packed in gelatin capsules to obtain 10,000 capsules each containing one mg of the active ingredient.

FORMULATION EXAMPLE 3

Soft Capsules:

| | |
|---|---|
| Compound (produced in Synthesis Example 4) | 10 g |
| PEG400 | 479 g |
| Saturated fatty acid triglyceride | 1,500 g |
| Peppermint Oil | 1 g |
| Polysorbate 80 | 10 g |
| Total | 2,000 g |

The above-mentioned components were mixed and encapsulated into No. 3 soft gelatin capsules by a usual method to obtain 10,000 soft capsules each containing one mg of the active ingredient, by an ordinary method.

FORMULATION EXAMPLE 4

Ointment:

| | |
|---|---|
| Compound (produced in Synthesis Example 4) | 1.0 g |
| Liquid paraffin | 10.0 g |
| Cetanol | 20.0 g |
| White vaseline | 68.4 g |
| Ethylparaben | 0.1 g |

-continued

| | |
|---|---|
| 1-Menthol | 0.5 g |
| Total | 100.0 g |

The above-mentioned components were mixed by a usual method to obtain 1% ointment.

FORMULATION EXAMPLE 5
Suppositories:

| | |
|---|---|
| Compound (produced in Synthesis Example 4) | 1 g |
| Witepsol H15* | 478 g |
| Witepsol W35* | 520 g |
| Polysorbate 80 | 1 g |
| Total | 1,000 g |

*Trade name for triglyceride compound

The above-mentioned components were melt-mixed by a usual method and poured into suppository containers, followed by cooling for solidification to obtain 1,000 suppositories of one g each containing one mg of the active ingredient.

Industrial Applicability

The compounds of the present invention have an antagonistic effect against angiotensin II and are useful for prevention and remedy of hypertension, congestive cardiac insufficiency, chronic renal insufficiency, aldosteronism, hyper-intraocular pressure, etc.

We claim:

1. Pyrazole compounds of the following general formula (1), and their tautomers and salts:

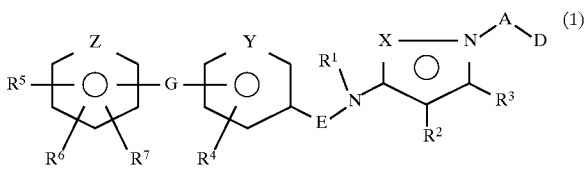

wherein $R^1$ represents a hydrogen atom, a $C_1$–$C_{10}$ alkyl group (said alkyl group is unsubstituted or substituted by one or more substituents selected from a halogen atom, a hydroxyl group and a $C_1$–$C_{10}$ alkoxy group), a $C_2$–$C_{10}$ alkenyl group (said alkenyl group is unsubstituted or substituted by one or more substituents selected from a halogen atom, a hydroxyl group and a $C_1$–$C_{10}$ alkoxy group), a $C_2$–$C_{10}$ alkynyl group (said alkynyl group is unsubstituted or substituted by one or more substituents selected from a halogen atom, a hydroxyl group and a $C_1$–$C_{10}$ alkoxy group), a $C_3$–$C_{10}$ cycloalkyl group (said cycloalkyl group is unsubstituted or substituted by one or more substituents selected from a halogen atom, a hydroxyl group and a $C_1$–$C_{10}$ alkoxy group), a $C_3$–$C_{10}$ cycloalkenyl group (said cycloalkenyl group is unsubstituted or substituted by one or more substituents selected from a halogen atom, a hydroxyl group and a $C_1$–$C_{10}$ alkoxy group) or a $C_6$–$C_{10}$ aromatic group (said aromatic group is unsubstituted or substituted by one or more substituents selected from a $C_1$–$C_{10}$ alkyl group, a halogen atom, a hydroxyl group and a $C_1$–$C_{10}$ alkoxy group);

$R^2$ represents $COX^1R^{12}$, wherein $R^{12}$ represents a hydrogen atom or a $C_1$–$C_{10}$ alkyl group and $X^1$ represents an oxygen atom or a sulfur atom;

$R^3$ represents a $C_1$–$C_{10}$ acyl group;

$R^4$, $R^5$ and $R^6$ each independently represents a hydrogen atom, a halogen atom, a hydroxyl group or a $C_1$–$C_{10}$ alkyl group;

$R^7$ represents a 5-tetrazolyl group,

X represents a nitrogen atom,

Y and Z each independently represent $CR^{40}$, wherein $R^{40}$ represents a hydrogen atom, a halogen atom or a $C_1$–$C_{10}$ alkyl group;

A represents $(CR^{41}R^{41'})m^7$, wherein $m^7$ represents 0, 1, 2 or 3, and $R^{41}$ and $R^{41'}$ each independently represents a hydrogen atom or a $C_1$–$C_{10}$ alkyl group;

D represents a $C_6$–$C_{10}$ aromatic group, wherein said aromatic group is unsubstituted or mono-substituted to penta-substituted by a halogen atom or a $C_1$–$C_{10}$ alkyl group;

E represents $CR^{52}R^{53}$, wherein $R^{52}$ and $R^{53}$ each independently represents a hydrogen atom or a $C_1$–$C_{10}$ alkyl group; and G represents a covalent bond.

2. Pyrazole compounds and their tautomers and salts as claimed in claim 1, wherein $R^1$ represents a $C_1$–$C_{10}$ alkyl group (said alkyl group is unsubstituted or substituted by one or more substituents selected from a halogen atom, a hydroxyl group and a $C_1$–$C_{10}$ alkoxy group), a $C_2$–$C_{10}$ alkenyl group (said alkenyl group is unsubstituted or substituted by one or more substituents selected from a halogen atom, a hydroxyl group and a $C_1$–$C_{10}$ alkoxy group) or a $C_3$–$C_{10}$ cycloalkyl group (said cycloalkyl group is unsubstituted or substituted by one or more substituents selected from a halogen atom, a hydroxyl group and a $C_1$–$C_{10}$ alkoxy group).

3. Pyrazole compounds and their tautomers and salts as claimed in claim 2, wherein $R^2$ represents $COX^1R^{12}$, wherein $R^{12}$ represents a hydrogen atom or a straight chain or branched $C_1$–$C_{10}$ alkyl group (said akyl group is unsubstituted or substituted by one or more substituents selected from a halogen atom, a hydroxyl group and a $C_1$–$C_{10}$ alkoxy group), and $X^1$ represents an oxygen atom;

$R^4$, $R^5$ and $R^6$ are hydrogen atoms; and

E represents $CH_2$.

4. A liquid compound for treatment of one or more of hypertension, congestive cardiac insufficiency, and chronic renal insufficiency, said compound containing at least one of pyrazole compounds and their tautomers and salts as claimed in claim 1, and at least one compound selected from the group consisting of solvents, surfactants, suspending agents and preservatives.

5. Pyrazole compounds and their tautomers and salts as claimed in claim 3, wherein $R^1$ represents a $C_1$–$C_{10}$ alkyl group; and Y and Z each represent CH.

6. Pyrazole compounds and their tautomers and salts as claimed in claim 5, wherein D represents a phenyl group (said phenyl group is unsubstituted or substituted by one or more substituents selected from a halogen atom and a $C_1$–$C_{10}$ alkyl group).

7. Pyrazole compounds and their tautomers and salts as claimed in claim 6, wherein $R^2$ represents a carboxyl group.

8. A composition for treating one or more of hypertension, congestive cardiac insufficiency, and chronic renal insufficiency, said composition containing at least one of pyrazole compounds and their tautomers and salts as claimed in claim 1, and at least one compound selected from the group consisting of excipients, binders, disintegrators, lubricants and smoothers.

* * * * *